United States Patent [19]

Osborne

[11] Patent Number: 4,485,110
[45] Date of Patent: Nov. 27, 1984

[54] β-LACTAM COMPOUNDS, AND USE
[75] Inventor: Neal F. Osborne, Rusper, England
[73] Assignee: Beecham Group Limited, England
[21] Appl. No.: 257,481
[22] Filed: Apr. 23, 1981
[30] Foreign Application Priority Data
  Apr. 24, 1980 [GB] United Kingdom ............... 8013563
[51] Int. Cl.³ ................ C07D 499/00; A61K 31/425
[52] U.S. Cl. .......................... 424/270; 260/245.2 R;
        260/245.2 T; 260/239 A; 424/271
[58] Field of Search ............... 260/245.2 T, 245.2 R;
        424/270

[56]         References Cited
       U.S. PATENT DOCUMENTS
  4,272,437  6/1981  Menard et al. ............ 260/245.2 R
  4,282,150  8/1981  Menard et al. ...................... 424/270
  4,301,074 11/1981  Christensen et al. ....... 260/245.2 R FOREIGN PATENT DOCUMENTS
  2013674  8/1979  United Kingdom .

OTHER PUBLICATIONS
H. O. House, Modern Synthetic Reactions, 2nd edition, 1972, pp. 595–596.

Primary Examiner—Nicholas S. Rizzo
Attorney, Agent, or Firm—Jacobs & Jacobs

[57]               ABSTRACT

A class of 6-alkylidene penem compounds of formula (II) have antibacterial and β-lactamase inhibitory properties:

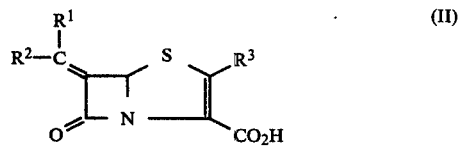

where $R^1$ and $R^2$ represent hydrogen or optionally substituted hydrocarbon or heterocyclic, and $R^3$ represents hydrogen or an organic group.

72 Claims, No Drawings

β-LACTAM COMPOUNDS, AND USE

This invention relates to β-lactam compounds and in particular to a class of 6-alkylidene penems which have antibacterial and β-lactamase inhibitory properties. The compounds are therefore useful in the treatment of antibacterial infections, either alone or in combination with other antibiotics.

British Patent Application No. 2,013,674 and European published Application No. 2210 both disclose 6-substituted 2-penem compounds of the general formula (I):

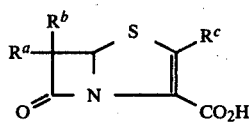

wherein $R^a$, $R^b$ and $R^c$ represent hydrogen or certain organic radicals. It has now been found that it is possible to prepare 6-alkylidene derivatives of 2-penems, which possess antibacterial activity. The compounds also inhibit β-lactamases and have a synergistic effect in combination with other β-lactam antibiotics. 6-Alkylidene 2-penems are neither disclosed nor suggested in British Patent Application No. 2,013,674 or European Application No. 2210.

Accordingly, the present invention provides a compound of formula (II):

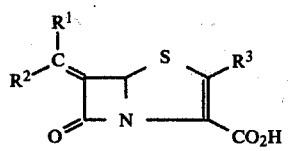

or a pharmaceutically acceptable salt or in vivo hydrolysable ester thereof, wherein $R^1$ and $R^2$ are the same or different and each represents hydrogen, or a hydrocarbon or heterocyclic group optionally substituted with a functional group; and $R^3$ represents hydrogen or an organic group.

Suitably $R^1$ and $R^2$ are independently hydrogen or a $C_{1-10}$ hydrocarbon group, especially $C_{1-6}$ alkyl or phenyl. Preferably one of $R^1$ and $R^2$ is hydrogen. Preferably one of $R^1$ and $R^2$ is methyl, ethyl or phenyl.

Suitably $R^3$ represents hydrogen or an organic group linked through a sulphur or carbon atom. For example $R^3$ may represent hydrogen or a group of formula $R^a$ or $SR^a$ where $R^a$ is an optional substituted $C_{1-10}$ hydrocarbon or heterocyclic group. Preferably, $R^3$ represents hydrogen, optionally substituted $C_{1-10}$ alkyl or optionally substituted $C_{1-10}$ alkylthio, wherein the substituent is hydroxy, $C_{1-6}$ alkoxy, $C_{1-6}$ alkanoyloxy, halogen, mercapto, $C_{1-6}$ alkylthio, heterocyclicthio, amino, mono- or dialkylamino, alkanoylamino, carboxy, or $C_{1-16}$ alkoxycarbonyl.

Pharmaceutically acceptable in vivo hydrolysable esters are those esters which hydrolyse in the human body to produce the parent acid or its salt. Such esters may be identified by administration to a test animal such as a rat or a mouse by intravenous administration and thereafter examining the test animal's body fluids for the presence of the compound of the formula (II) or its salt.

Suitable ester groups of this type include those of part formulae (a), (b) and (c):

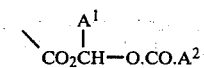

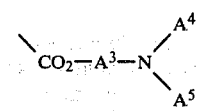

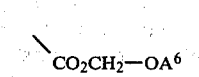

wherein $A^1$ is hydrogen, methyl, or phenyl, $A^2$ is $C_{1-6}$ alkyl, $C_{1-6}$ alkoxy or phenyl; or $A^1$ and $A^2$ together form a 1,2-phenylene group optionally substituted by one or two methoxy groups; $A^3$ represent $C_{1-6}$ alkylene optionally substituted with a methyl or ethyl group—$A^4$ and $A^5$ independently represent $C_{1-6}$ alkyl; $A^6$ represents $C_{1-6}$ alkyl. Examples of suitable in vivo hydrolysable ester groups include acetoxymethyol, pivaloyloxymethyl, α-acetoxyethyl, α-acetoxybenzyl, α-pivaloyloxyethyl, ethoxycarbonyloxymethyl, α-ethoxycarbonyloxyethyl, dimethylaminomethyl, diethylaminomethyl, diethylaminoethyl, phthalidyl and dimethoxyphthalidyl groups.

Suitable pharmaceutically acceptable salts of the 3-carboxylic acid group of the compound of formula (II) include metal salts, eg aluminum, alkali metal salts such as sodium or potassium, alkaline earth metal salts such as calcium or magnesium, and ammonium or substituted ammonium salts, for example those with lower alkylamines such as triethylamine, hydroxy-lower alkylamines such as 2-hydroxyethylamine, bis-(2-hydroxyethyl)-amine or tri-(2-hydroxyethyl)-amine, cycloalkylamines such as bicyclohexylamine, or with procaine, dibenzylamine, N,N-dibenzylethylenediamine, 1-ephenamine, N-ethylpiperidine, N-benzyl-β-phenethylamine, dehydroabetiylamine, N,N'-bisdehydroabietylethylenediamine, or bases of the pyridine type such as pyridine, collidine or quinoline, or other amines which have been used to form salts with known penicillins.

In formula (II), suitable $C_{1-6}$ alkyl groups for $R^1$ and $R^2$ include methyl, ethyl, n- and iso-propyl, n-, iso, sec- and tert-butyl.

Preferably one of $R^1$ and $R^2$ is hydrogen and the other is methyl.

Suitable groups for $R^3$ include hydrogen, or methyl, ethyl, propyl, methylthio, ethylthio, methylsulphinyl, ethylsulphinyl, hydroxymethyl, methoxymethyl, ethoxymethyl, acetoxymethyl, 1-, or 2-acetoxyethyl, aminomethyl, 2-aminoethyl, acetamidomethyl, 2-acetamidoethyl, carboxymethyl, hydroxymethylthio, 2-hydroxyethylthio, methoxymethylthio, 2-methoxyethylthio, acetoxymethylthio, aminomethylthio, 2-aminoethylthio, acetamidomethylthio, 2-acetamidoethylthio, carboxymethylthio, or pyridylthio.

Particular groups for $R^3$ are hydrogen aminomethyl, aminoethyl, methylthio, ethylthio, 2-aminoethylthio, 2-hydroxyethylthio, methyl, ethyl, acetamidoethyl, pyridylthio, and ethylsulphinyl.

Specific compounds of this invention include the following and their pharmaceutically acceptable salts:
6-(Z)-ethylidene-2-ethylthiopenem-3-carboxylic acid;
6-(E)-ethylidene-2-ethylthiopenem-3-carboxylic acid;

6-(Z)-ethylidenepenem-3-carboxylic acid;
6-(Z)-ethylidene-2-n-propylpenem-3-carboxylic acid;
2-(2-acetamidoethylthio)-6-ethylidenepenem-3-carboxylic acid;
6-(Z)-ethylidene-2-methylpenem-3-carboxylic acid;
6-ethylidene-2-(2-pyridylthio)penem-3-carboxylic acid;
2-(2-aminoethylthio)-6-ethylidenepenem-3-carboxylic acid;
6-ethylidene-2-ethylsulphinylpenem-3-carboxylic acid;
6-(Z)-benzylidene-2-ethylthiopenem-3-carboxylic acid;
2-ethylthio-6-isopropylidenepenem-3-carboxylic acid.

The compounds of formula (II) may exist in two optically active forms and it is to be understood that both such forms as well as racemic mixtures thereof are embraced by the present invention. It is believed that the more active form is that of structure (IIa):

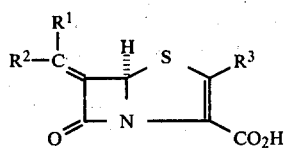
(IIa)

The compounds of this invention may be prepared by dehydration of a compound of formula (III):

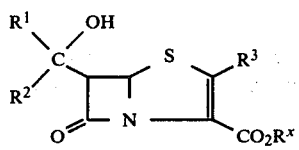
(III)

wherein $R^1$, $R^2$ and $R^3$ are as defined with respect to formula (II) above and $R^x$ represents hydrogen, or a carboxyl-blocking group, and thereafter if necessary carrying out one or more of the following steps:
(i) removal of any carboxyl blocking group $R^x$;
(ii) converting the product to a pharmaceutically acceptable salt or in vivo hydrolysable ester group.

Suitable carboxyl-blocking derivatives for the group —$CO_2R^x$ in formula (III) include salts, ester, and anhydride derivatives of the carboxylic acid. The derivative is one which may readily be cleaved at a later stage of the reaction. The salts need not be pharmaceutically acceptable. Suitable salts include inorganic salts, for example metal salts such as silver or mercuric salt, or alkali metal salts such as the lithium or sodium salt, tertiary amine salts, such as those with tri-lower-alkylamines, N-ethylpiperidine, dimethylpiperazine. A preferred salt is with triethylamine.

Suitable ester-forming carboxyl-blocking groups are those which may be removed under conventional conditions. Such groups for $R^x$ include benzyl, p-methoxybenzyl, 2,4,6-trimethylbenzyl, 3,5-di-t-butyl-4-hydroxybenzyl, benzoylmethyl, p-nitrobenzyl, 4-pyridylmethyl, 2,2,2-trichloroethyl, 2,2,2-tribromoethyl, t-butyl, t-amyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, p-toluenesulphonylethyl, methoxymethyl, a silyl, stannyl or phosphorus-containing group, an oxime radical of formula —N=CHR° where R° is aryl or heterocyclic, or an in vivo hydrolysable ester radical such as defined above.

The carboxyl group may be regenerated from any of the above esters by usual methods appropriate to the particular $R^x$ group, for example, acid- and base-catalysed hydrolysis, or by enzymically-catalysed hydrolysis, or by hydrogenation. The hydrolysis must of course be carried out under conditions to which the groups on the rest of the molecule are stable.

When it is desired to produce a compound of formula (II) in the form of a free acid or salt by the process of this invention, a compound of formula (III) is generally employed wherein $R^x$ is a carboxyl-blocking group. For the preparation of a compound of formula (II) in the form of a pharmaceutically acceptable ester, it is convenient to employ a compound of formula (III) wherein $R^x$ represents the desired ester group.

The dehydration process of this invention may be carried out by treating a compound of formula (III) with a compound of formula (IV):

wherein $R^4$ and $R^5$ are independently aryl, or $C_{1-6}$ alkyl optionally substituted with aryl; and a compound of formula (V):

(V)

wherein a, b and c are independently 0 or 1, and $R^6$, $R^7$ and $R^8$ are independently aryl or $C_{1-6}$ alkyl optionally substituted with aryl.

In the compounds of the formula (IV) $R^4$ and $R^5$ are preferably selected from methyl, ethyl, propyl, butyl, phenyl and benzyl, the ethyl and t-butyl groups being preferred. Thus a preferred compound of formula (IV) is diethyl azodicarboxylate.

It is often convenient that $R^4$ and $R^5$ represent the same group.

Preferred compounds of the formula (V) include triarylphosphines and trialkylphosphites. Preferred groups $R^6$, $R^7$ and $R^8$ include methyl, ethyl, n-propyl, n-butyl, benzyl, phenyl and methoxyphenyl. Conveniently, $R^6$, $R^7$ and $R^8$ represent the same group. A particularly preferred compound of the formula (V) is triphenylphosphine.

Generally, approximately two equivalents of the compounds of the formulae (IV) and (V) are used per mole of compound (III).

The elimination reaction is generally carried out at a non-extreme temperature, such as −20° to +100° C. We have found it convenient to begin the reaction at a depressed temperature, such as 0° C., and then to allow the temperature to rise to about room temperature.

The reaction is performed in an inert aprotic organic solvent. Suitable solvents include tetrahydrofuran, dioxane, ethyl acetate, benzene and the like.

Alternatively, the dehydration process of this invention may be carried out by converting compound (III) into a compound of formula (VI):

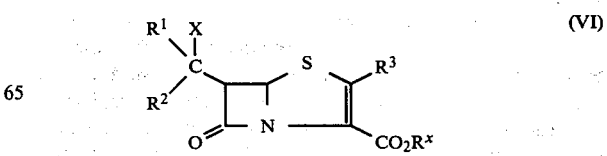
(VI)

and eliminating the elements of a compound of formula H-X therefrom, wherein $R^1$, $R^2$, $R^3$ and $R^x$ are as defined with respect to formula (III) above, and X is a leaving group.

Suitable groups for the leaving group X include halogen; a group of formula $-O-SO_2-(O)_n-R^9$ or $-O-CO-(O)_n-R^9$ wherein n is zero or 1 and $R^9$ is aryl or $C_{1-6}$ alkyl optionally substituted with aryl; and a group of formula $-OPO(OR^{10})_2$ wherein $R^{10}$ is $C_{1-6}$ alkyl or aryl.

Preferred groups of formula $-OCO(O)_nR^9$ are those wherein n is zero and $R^9$ is $C_{1-6}$ alkyl, in particular acetoxy.

The compounds of formula (VI) may be prepared from the compounds of formula (III) by replacing the hydroxy group by a group X. Alternatively the group X can be introduced into the molecule at an earlier stage in the synthesis of the penem nucleus. In particular the groups $-OSO_2(O)_nR^9$ and $-OCO(O)_nR^9$ can be introduced at the beginning of, or at any stage during, the synthesis of the penem. In each case, the group X is introduced by replacing a hydroxyl group. One particular novel intermediate useful for this purpose is the compound of formula (VII):

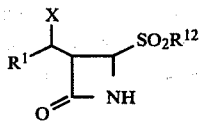

(VII)

wherein $R^1$ is as defined with respect to formula (II) above, and $R^{12}$ represents methyl or benzyl.

The elimination of the elements of a compound of the formula H-X is most conveniently brought about by treatment of a compound of the formula (VI) with a base in an aprotic medium. The base employed will be a base of low nucleophilicity so that in general primary and secondary amines will not be suitable. Suitable bases include powdered inorganic bases such as alkali metal carbonates, bicarbonates or hydroxides, for example powdered potassium carbonate, or hydrides or 1,8-diazabicyclo [5.4.0]undec-7-ene. Suitable solvents for use in this reaction include dimethylformamide, hexamethylphosphoramide, dichloromethane, tetrahydrofuran and the like.

The elimination may be effected at a non-extreme temperature such as $-20°$ to $+70°$ C., for example $+10°$ to $+25°$ C. The reaction may be conveniently effected at ambient temperature.

The compounds of this invention may also be prepared by a process which comprises reacting a sulphoxide of formula (VIII):

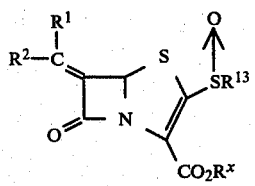

(VIII)

wherein $R^1$, $R^2$ and $R^x$ are as defined above and $R^{13}$ represents an organic radical different to the group $R^3$; with a thiol of formula (IX) or a reactive derivative thereof:

$$R^3-SH \quad (IX)$$

and thereafter if necessary carrying out one or more of the following steps:
(i) removal of any carboxyl blocking group $R^x$;
(ii) converting the product to a pharmaceutically acceptable salt or in vivo hydrolysable ester group.

The process may be carried out in any inert solvent such as N,N-dimethylformamide (DMF), tetrahydrofuran (THF), dioxane, hexamethylphosphoramide (HMPA) or glyme. The solvent DMF is preferred. A low temperature is preferred, suitably below $0°$ C., preferably below $-20°$ C. especially from about $-30°$ C. to about $-70°$ C.

When the thiol compound of formula (IX) itself is employed, the reaction is generally carried out in the presence of a base, although this is not essential. Examples of suitable bases include sodium hydride, potassium hydride, sodium amide, potassium amide, sodium hydroxide, potassium hydroxide, sodium ethoxide, sodium methoxide, potassium butoxide, triethylamine, and tripropylamine. Advantageously, the base is used in an amount of at least 0.9 equivalent, preferably 1.0 to 1.2 equivalents, per mole of the thiol compound.

Instead of using the base in the reaction, a reactive derivative of the thiol compound of formula (IX) may be used. Preferably the reactive derivative is a salt of the thiol (IX), in particular a salt with an alkali metal, preferably sodium or potassium.

The amount of the thiol compound of formula (IX) or its reactive derivative is not critical. Generally, however, it is used in an amount of at least 1.0 mole, preferably 1.1 to 1.5 moles, per mole of the compound of formula (VIII).

Compounds of formula (VIII) may be prepared by S-oxidation of a compound of formula (X):

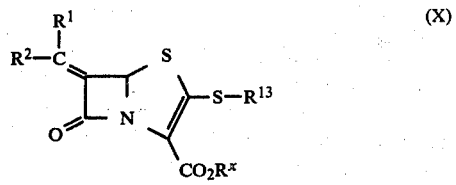

(X)

wherein $R^1$, $R^2$, $R^4$ and $R^x$ are as defined with respect to formula (V) above; with a mild oxidising agent.

Suitable mild oxidising agents include perbenzoic acid, hydrogen peroxide, selenium dioxide or sodium metaperiodate. Substituted perbenzoic acids such as m-chloroperbenzoic acid are most preferred.

The present invention also provides a pharmaceutical composition which comprises a compound of the formula (II) as hereinbefore defined or a pharmaceutically acceptable salt or in vivo hydrolysable ester thereof and a pharmaceutically acceptable carrier.

If the compound of the invention present in such a composition is in the form of a salt then suitable salts include pharmaceutically acceptable alkali metal or alkaline earth metal salts, or a salt with a pharmaceutically acceptable nitrogenous base. Particularly suitable salts include the sodium salt and the potassium salt.

The compositions may be formulated for administration by any route, for example oral, topical or parenteral, although an oral administration is preferred. The compositions may be in the form of tablets, capsules, powders, granules, lozenges, or liquid preparations, such as oral or sterile parenteral solutions or suspensions.

Tablets and capsules for oral administration may be in unit dose presentation form, and may contain conventional excipients such as binding, for example syrup, acacia, gelatin, sorbitol, tragacanth, or polyvinyl-pyrrolidone; fillers, for example lactose, sugar, maizestarch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, glycose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired convention flavouring or colouring agents.

Suppositories will contain conventional suppository bases, eg cocao-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle.

Unit-dose forms according to this invention will normally contain from 50 to 500 mg of a compound of this invention, for example about 62.5, 100, 125, 150, 200, 250 or 300 mg. Such compositions may be administered up to 6 times a day or more conveniently 2, 3 or 4 times a day so that the total daily dose for a 70 kg adult is about 200 to 2000 mg, for example about 400, 600, 750, 1000 or 1500 mg.

The compositions of this invention may be used to treat infections of the respiratory tract, urinary tract of soft tissues in humans, mastitis in cattle or the like.

The present invention also provides synergistic pharmaceutical compositions which comprise a pharmaceutical composition as hereinbefore described which also contains a penicillin or a cephalosporin.

Suitable penicillins for inclusion in the compositions of this invention include benzyl penicillin, phenoxymethylpenicillin, ampicillin, amoxycillin, ticarcillin, suncillin, sulbenicillin, azlocillin, mezlocillin, apalcillin, piperacillin or pro-drugs of these compounds.

Particularly suitable penicillins for inclusion in orally adminstrable compositions of this invention include ampicillin and its orally adminstrable pro-drugs, amoxycillin and its orally administrable pro-drugs and orally administrable pro-drugs of carbenicillin. Thus particularly suitable penicillins include ampicillin anhydrate, ampicillin trihydrate, sodium ampicillin, talampicillin hydrochloride, pivampicillin hydrochloride, bacampicillin hydrochloride; amoxycillin trihydrate, sodium amoxycillin; and the sodium salts of the phenyl and 5-indanyl α-esters of carbenicillin.

A preferred penicillin for inclusion in the orally administerable compositions of this invention is amoxycillin trihydrate. A further preferred penicillin for inclusion in the orally administrable compositions of this invention is ampicillin trihydrate.

Particularly suitable penicillins for inclusion in injectably administrable compositions of this invention include injectable salts such as the sodium salt of ampicillin, amoxycillin, carbenicillin and ticarcillin.

A preferred penicillin for inclusion in the injectably administrable compositions of this invention is sodium amoxycillin. A further preferred penicillin for inclusion in the injectably administrable compositions of this invention is sodium ampicillin.

Particularly suitable cephalosporins for inclusion in the compositions of this invention include cephaloridine, cephalexin, cephradine, cefazolin and cephalothin.

A particularly suitable cephalosporin for inclusion in the orally administrable compositions of this invention is cephalexin.

Particularly suitable cephalosporins for inclusion in the injectably administrable compositions of this invention include cephaloridine, cefazolin and cephradine, generally as their pharmaceutically acceptable salt such as the sodium salt.

The weight ratio between compound of this invention and penicillin or cephalosporin is generally from 10:1 to 1:10, or more usually from 5:1 to 1:5 and normally from 3:1 to 1:3.

The penicillin or cephalosporin is generally utilised in its conventionally administered amount.

The following Examples illustrate this invention.

PREPARATION 1(a)

(4RS)-3,3-Dibromo-1(1-methoxycarbonyl-2-methylprop-1-enyl)-4-methylthioazetidin-2-one

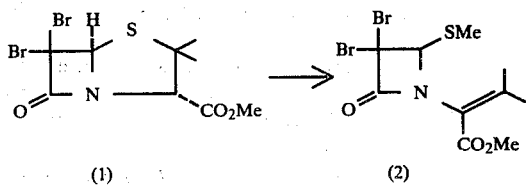

A mixture of methyl 6,6-dibromopenicillanate (J. P. Clayton, *J. Chem. Soc.* (C), 1969, 2123) (42.0 g), methyl iodide (42 ml) and finely powdered sodium hydroxide (5.4 g) in dry tetrahydrofuran (400 ml) was stirred at room temperature for 2.5 hours. The mixture was filtered and the filtrate concentrated. The resulting solution was diluted with ethyl acetate (1 liter) and washed with brine (3×100 ml). The dried (MgSO$_4$) organic layer was evaporated and the residue chromatographed on silica gel eluting with ethyl acetate/petroleum ether mixtures to give the secopenicillanate (2) (25.8 g) as an oil, $v_{max}$. (CHCl$_3$) 1785, 1725; δ ppm (CDCl$_3$) 2.00 (3H, s), 2.23 (3H, s) 2.32 (3H, s), 3.82 (3H, s), 5.52 (1H, s).

PREPARATION 1(b)

(3ξ, 4RS)-3-Bromo-3[1-(ξ)-hydroxyethyl]-1(1-methoxycarbonyl-2-methylprop-1-enyl)-4-methylthioazetidin-2-one

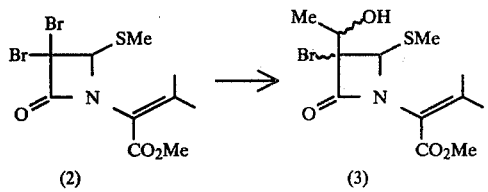

(a) Using methyl magnesium bromide

A solution of methyl magnesium bromide (2M in diethyl ether, 14.2 ml) was added, dropwise over five minutes, to a stirred solution of the dibromosecopenicillanate (2) (10.0 g) indry tetrahydrofuran (200 ml) at −76° C. After stirring at −76° C. for a further twenty minutes a solution of acetaldehyde (3 ml) in dry tetrahydrofuran (10 ml) was added dropwise over five minutes. The mixture was stirred at −76° C. for a further ten minutes, treated with a saturated solution of ammonium chloride (10 ml), and allowed to attain room temperature. The mixture was diluted with ethyl acetate and the organic phase separated. The organic layer was washed with brine, dried (MgSO₄), and evaporated to give a crude gum. Chromatography of the crude product on silica gel eluting with ethyl acetate/petroleum ether mixtures gave the bromohydrin (3) (7.28 g), a 9:1 mixture of isomers, as a viscous oil, $\nu_{max}$. (CHCl₃) 3600–3100, 1765, 1725 cm⁻¹; δ(CDCl₃) 1.43 (3H, d, J 6½ Hz), 2.04 (3H, s), 2.13 (3H, s), 2.28 (3H, s), 2.53 br (1H, d, J approx. 4 Hz, exch. D₂O), 3.78 (3H, s), 4.05–4.40 (1H, m, collapsing to 4.21 q. J 6½ Hz on exch. D₂O), 5.25 (0.9H, s), 5.32 (0.1H, s).

(b) Using n-butyl lithium

The above experiment was repeated using n-butyl lithium (one equivalent) in place of methyl magnesium bromide to give, after chromatography, the bromohydrin (3) in 36% yield.

PREPARATION 1(c)

(3RS, 4RS) and (3RS, 4RS)-3[1-(ξ)-Hydroxyethyl]-1(1-methoxycarbonyl-2-methylprop-1-enyl)-4-methylthioazetidin-2-one

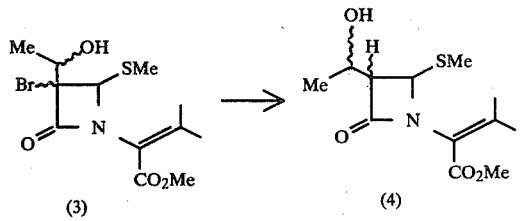

The bromohydrin (3) (7.04 g) was stirred with zinc-silver couple (prepared from 2.60 g zinc dust according to the method of R. D. Clark and C. H. Heathcock, J. Org. Chem., 1973, 3659) in methanol (100 ml) containing glacial acetic acid (0.57 ml) at room temperature for ten minutes (the mixture was initially cooled with an ice-water bath in order to moderate a slightly exothermic reaction). The mixture was filtered through Kieselguhr, the residue being washed with a little methanol. The combined filtrates were evaporated to low volume and diluted with ethyl acetate. The solution was washed successively with N. hydrochloric acid, brine, dilute sodium bicarbonate solution, and brine. The dried (MgSO₄) organic layer was evaporated and the residual gum, chromatographed on silica gel eluting with ethyl acetate/petroleum ether mixtures to give a 3:1 mixture of the cis- and trans-hydroxyethylazetidinones (4) (4.64 g) as a gum, $\nu_{max}$. (CHCl₃) 3600–3200, 1750, 1720 cm⁻¹; δ ppm (CDCl₃) 1.32 and 1.42 (3H, each d, J 6 Hz), 1.98 and 2.00 (3H, each s), 2.10, 2.17 and 2.24 (6H, each s), 2.35–2.90 (1H, broad signal, exch. D₂O), 3.14 (¼H, dd, J 2 and 5 Hz), 3.41 (¾H, dd, J 5 and 9Hz), 7.75 (3H, s), 4.00–4.40 (1H, m, simplifies on exch. D₂O), 4.90 (¼H, d, J 2 Hz), 5.04 (¾H, d, J 5 Hz).

PREPARATION 1(d)

3(1-t-Butyldiphenylsilyloxyethyl)-1(1-methoxycarbonyl-2-methylprop-1-enyl)-4-methylthioazetidin-2-one

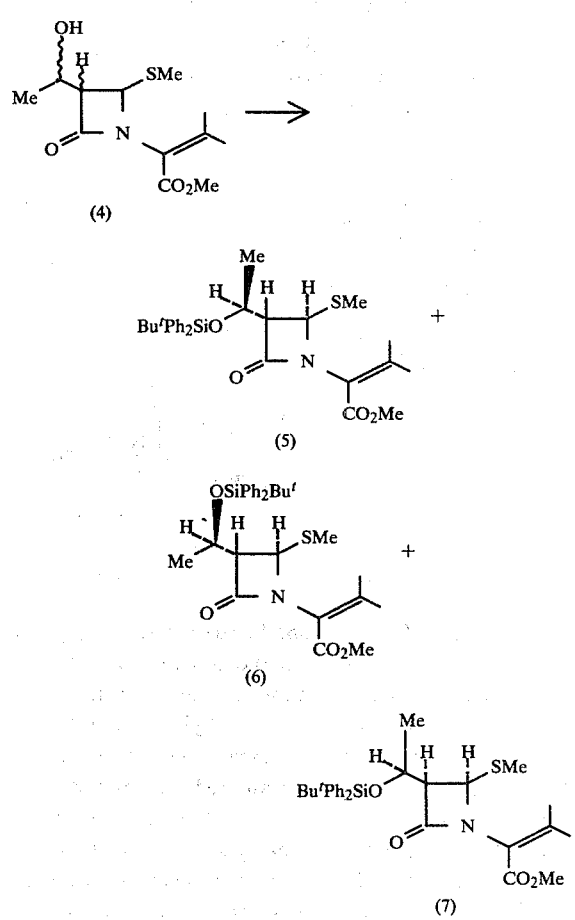

The mixture of cis and trans-hydroxyethylazetidinones(4) (2.00 g) was dissolved in dry dimethylformamide (20 ml) and treated with imidazole (1.10 g) and t-butyldiphenylsilyl chloride (2.21 g). The mixture was kept at room temperature for eighteen hours, diluted with ethyl acetate, and washed successively with N. hydrochloric acid, brine, saturated sodium bicarbonate solution, and brine. The dried (MgSO₄) organic layer was evaporated and the residue chromatographed on silica gel eluting with ethyl acetate/petroleum ether mixtures to give two fractions. The less polar fraction, the (3RS, 4SR)-3 [1-(RS)-t-butyldiphenylsilyloxyethyl]azetidinone (5), contaminated with approximately 15% of the (3RS, 4SR)-3[1-(SR)-t-butyldiphenylsilyloxyethyl]azetidinone (6) was obtained as a gum (1.15 g), $\nu_{max}$. (CHCl$_3$) 1750, 1725 cm$^{-1}$; δ ppm (CDCl$_3$) 1.0–1.3 (12H, m), 1.94 (3H, s), 2.05 and 2.08 (3H, each s), 2.19 (3H, s), 3.10 (dd, J 3 and 6 Hz) and 3.25 (dd, J 3 and 5 Hz) together 1H, 3.63 (0.15H, s), 3.69 (0.85H, s), 4.15–4.50 (1H, m), 5.11 (1H, d, J 3 Hz), 7.2–7.8 (10H, m). The more polar fraction, the (3RS, 4RS)-3[1-(SR)-t-butyldiphenylsilyloxyethyl]azetidnone (7) (2.20 g), was obtained as a gum, $\nu_{max}$. (CHCl$_3$) 1750, 1720 cm$^{-1}$; δ ppm (CDCl$_3$) 1.05 (9H, s), 1.24 (3H, d, J 6 Hz), 2.00 (6H, s), 2.20 (3H, s), 3.58 (1H, dd, J 6 and 6 Hz), 3.73 (3H, s), 4.36 (1H, dq, J 6 and 6 Hz), 4.98 (1H, d, J 6 Hz), 7.2–7.9 (10H, m). (Found, M$^+$—Bu$^t$ 454.1479. C$_{24}$H$_{28}$NO$_4$SSi requires 454.1508).

PREPARATION 1(e)

(3RS, 4RS)-3[1-(SR)-t-Butyldiphenylsilyloxyethyl]-4-methylsulphonylazetidin-2-one

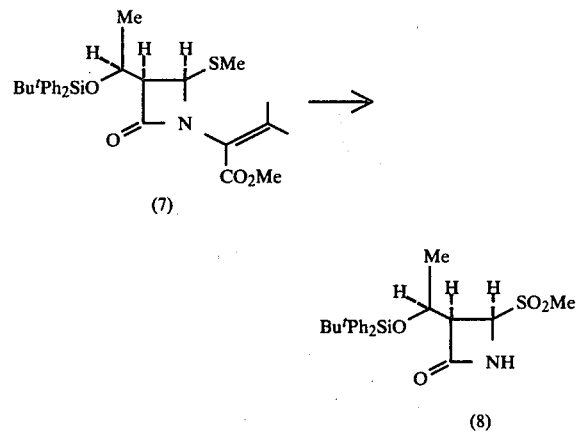

A solution of m-chloroperbenzoic and (1.60 g) in ethyl acetate (10 ml) was added dropwise over ten minutes to a stirred, ice-bath cooled, solution of the (3RS, 4RS) azetidinone (7) (2.16 g) in ethyl acetate (50 ml). The mixture kept at room temperature for two and a half hours and washed with saturated sodium bicarbonate solution (2×15 ml) and brine (3×15 ml). The dried (MgSO$_4$) organic layer was diluted to 100 ml with ethyl acetate, cooled to −20° C., and ozonised oxygen passed for thirty minutes. The excess ozone was removed by passage of argon and the mixture treated with methanol (50 ml). The mixture was kept at room temperature for forty hours and evaporated to give a crude gum which was chromatographed on silica gel eluting with ethyl acetate/petroleum ether mixtures to give the sulphone (8) (1.57 g) as a waxy solid, $\nu_{max}$. (CHCl$_3$) 3400, 1790 cm$^{-1}$; δ ppm (CDCl$_3$) 1.01 (9H, s), 1.23 (3H, d, J 6 Hz), 2.91 (3H, s), 3.77 (1H, dd, J 5 and 8 Hz), 4.67 (1H, d, J 5 Hz), 4.87 (1H, dq, J 6 and 8 Hz), 6.88 br (1H, s), 7.3–7.8 (10H, m). (Found: M$^+$—Bu$^t$ 374.0897. C$_{18}$H$_{20}$NO$_4$SSi requires 374.0882).

PREPARATION 1(f)

(3RS, 4SR)-3[1-(SR)-t-Butyldiphenylsilyloxyethyl]-4-ethylthiothiocarbonylthioazetidin-2-one

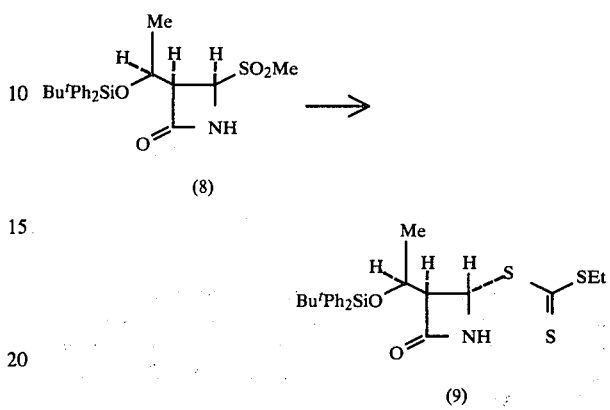

A mixture of the sulphone (8) (1.49 g) in methylene chloride (25 ml) and potassium ethyl trithiocarbonate (670 mg) in water (5 ml) was stirred vigorously at room temperature. After four hours the organic phase was separated and the aqueous layer extracted with methylene chloride (5 ml). The combined organic layers were washed with brine (3×5 ml), dried (MgSO$_4$) and evaporated. Chromatography of the residue on silica gel eluting with ethyl acetate/petroleum ether mixtures gave the trithiocarbonate (9) (1.29 g) as a yellow solid, m.p. 110°–111° C. (needles ex ethyl acetate/petroleum ether), $\lambda_{max}$. (EtOH) 301 nm. ($\epsilon_m$14,800); $\nu_{max}$. (CHCl$_3$) 3410, 1770 cm$^{-1}$; δ ppm (CDCl$_3$) 1.02–1.12 (12H, s+partially obscured d), 1.38 (3H, t, J 7 Hz), 3.19 (1H, dd, J 2 and 4½ Hz), 3.35 (2H, q, J 7 Hz), 4.1–4.5 (1H, m), 5.63 (1H, d, J 2 Hz), 6.59 br (1H, s), 7.3–7.8 (10H, m). (Found: C, 59.3; H, 6.5; N, 2.9; S, 19.4. C$_{24}$H$_{31}$NO$_2$S$_3$Si requires C, 58.9; H, 6.3; N, 2.9; S, 19.6%.)

PREPARATION 1(g)

(3RS, 4SR)-3[1-(SR)-t-Butyldiphenylsilyloxyethyl]-4-ethylthiothiocarbonylthio-1(1-hydroxy-1-p-nitrobenzyloxycarbonylmethyl)azetidin-2-one

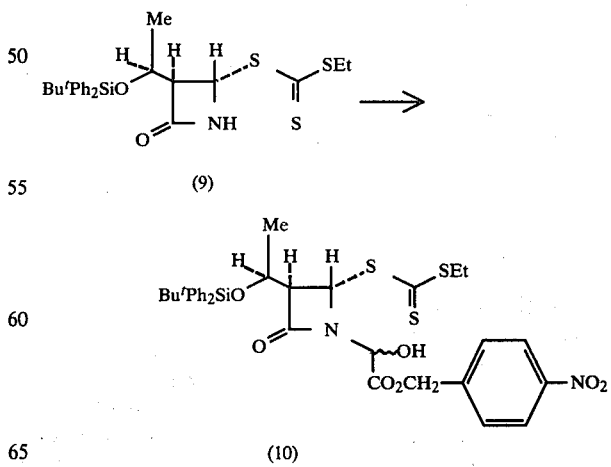

The trithiocarbonate (9) (1.25 g) and p-nitrobenzyl glyoxylate monohydrate (1.16 g) were refluxed in benzene (50 ml) under argon for thirty hours with provision for removal of water. The mixture was evaporated and the residual gum chromatographed on silica gel eluting with ethyl acetate/petroleum ether to give the hydroxy-ester (10) (1.51 g), a mixture of stereoisomers, as a gum, $\nu_{max}$. (CHCl$_3$) 3500 br, 3400 br, 1775, 1750 (slight shoulder) cm$^{-1}$; δ ppm (CDCl$_3$) 1.02 (9H, s), 1.35 (3H, t, J 7 Hz), 3.24–3.49 (3H, m), 3.6–3.9 br (1H, m, exch. D$_2$O), 4.2–4.5 (1H, m), 5.15–5.46 (2⅔H, m), 5.5–5.7 br (⅓H, m, collapses to 5.58, s, on exch. D$_2$O), 6.30 and 6.35 (1H, each d, J 2½ Hz), 7.2–7.8 (12H, m), 8.18 and 8.21 (2H, each d, J 8 Hz).

PREPARATION 1(h)

(3RS, 4SR)-3[1-(SR)-t-Butyldiphenylsilyloxyethyl]-1-(1-chloro-1-p-nitrobenzyloxycarbonylmethyl)-4-ethylthio-thiocarbonylthioazetidin-2-one

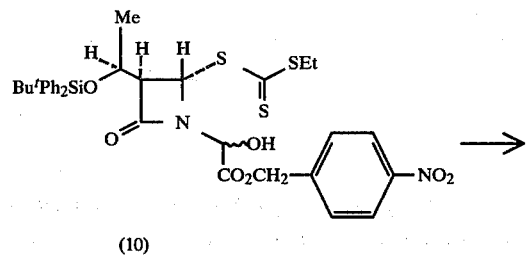

(10)

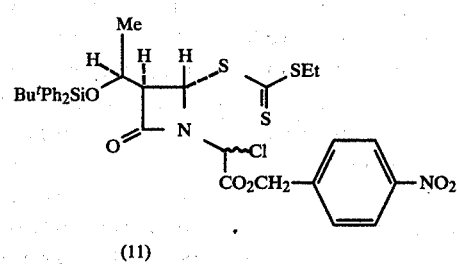

(11)

A solution of thionyl chloride (384 mg) in dry tetrahydrofuran (5 ml) was added dropwise over five minutes to a stirred mixture of the hydroxy-ester (10) (1.50 g) and 2,6-ludidine (345 mg) in dry tetrahydrofuran (30 ml) at −10° C. The mixture was stirred at −10° C. for ten minutes, filtered, and evaporated. The residual gum was re-evaporated from dry toluene (2×5 ml) to give the chloro-ester (11) (1.55 g) as a gum, $\nu_{max}$. (CHCl$_3$) 1785 cm$^{-1}$.

PREPARATION 1(i)

(3RS, 4SR)-3[1-(SR)-t-Butyldiphenylsilyloxyethyl]-4-ethyl-thiothiocarbonylthio-1(1-p-nitrobenzyloxycarbonyl-1-triphenylphosphoranylidenemethyl)azetidin-2-one

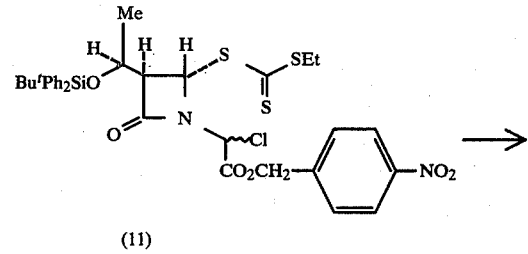

(11)

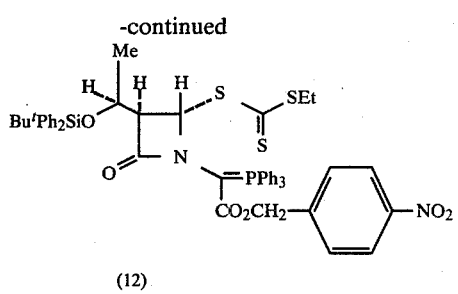

(12)

A mixture containing the chloro-ester (11) (1.55 g), triphenylphosphine (1.13 g), and 2,6-lutidine (278 mg) in dry dioxan (30 ml) was stirred at 60° C. under dry argon for seventy-two hours. The mixture was cooled, filtered, and the filtrate concentrated. The mixture was diluted with ethyl acetate (50 ml) and washed with N. hydrochloric acid, brine, saturated sodium bicarbonate solution, and brine. The dried (MgSO$_4$) organic layer was evaporated and the residue chromatographed on silica gel eluting with ethyl acetate/petroleum ether mixtures to give the phosphorane (12) (1.17 g) as an amorphous solid, $\nu_{max}$. (CHCl$_3$) 1745, 1610 cm$^{-1}$.

PREPARATION 1(j)

(5RS, 6SR, 8RS) and (5RS, 6RS, 8SR)-p-Nitrobenzyl 6(1-t-Butyldiphenylsilyloxyethyl)-2-ethylthiopenem-3-carboxylate

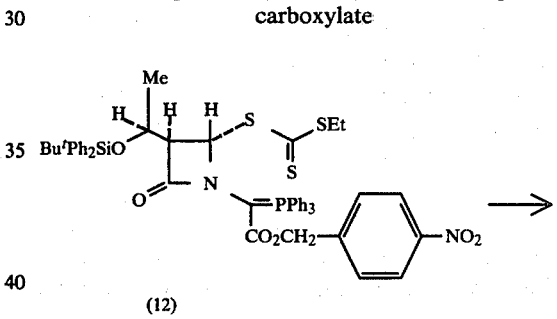

(12)

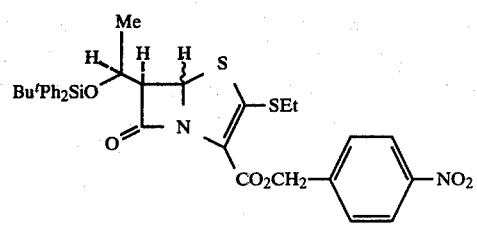

(13)

A solution of the phosphorane (12) (1.03 g) in xylene (1000 ml) was refluxed under argon for seven hours. The mixture was evaporated and the residue chromatographed on silica gel eluting with ethyl acetate/petroleum ether mixtures to give the penem ester (13) (440 mg), a 4:1 mixture of (5RS, 6SR, 8RS) and (5RS, 6RS, 8SR) isomers, as an amorphous solid, $\nu_{max}$. (CHCl$_3$) 1790 and 1690 cm$^{-1}$; δ ppm (CDCl$_3$) 0.99 and 1.01 (9H, each s), 1.13 (d, J 6 Hz), 1.30 (t, J 7 Hz) and 1.35 (t, J 7 Hz) together 6H, 2.65–3.15 (2H, m), 3.55–3.95 (1H, m), 3.95–4.50 (1H, m), 5.15 and 5.43 (2H, ABq, J 14 Hz), 5.49 (0.8H, d, J 1½ Hz), 5.65 (0.2H, d, J 4 Hz), 7.2–7.8 (12H, m), 8.14 and 8.16 (2H, each d, J 9 Hz). Unchanged phosphorane (12) (161 mg) was also isolated in this experiment.

PREPARATION 1(k)

(5RS, 6SR, 8RS) and (5RS, 6RS, 8SR)-p-Nitrobenzyl 2-Ethylthio-6(1-hydroxyethyl)penem-3-carboxylate

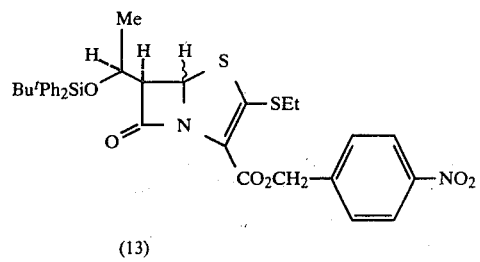

(13)

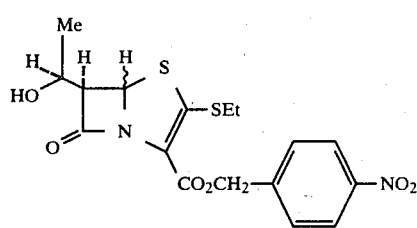

(14) + (15)

Tetra-n-butylammonium fluoride (2.44 ml of a solution containing 0.5 mMole n-Bu$_4$NF.3H$_2$O/ml tetrahydrofuran, dried over Molecular Sieves Type 4A for twenty-four hours) was added over five minutes to an ice-bath cooled solution of the penem silyl ethers (13) (395 mg) in dry tetrahydrofuran (20 ml). The mixture was kept at ice-bath temperature for thirty minutes and then allowed to attain room temperature during a further thirty minutes. The mixture was diluted with ethyl acetate (50 ml) and washed with 5% citric acid (5 ml) and brine (3×10 ml). The dried (MgSO$_4$) organic layer was evaporated and the residue chromatographed on silica gel eluting with ethyl acetate/petroleum ether mixtures to give the hydroxyethyl penem (105 mg), a mixture of cis and trans-isomers, as a solid. Crystallisation of the mixture from ethyl acetate/petroleum ether gave the pure (5RS, 6SR, 8RS) penem (14) (68 mg) as fine needles, m.p. 131°–134° C., $\nu_{max}$. (EtOH) 262 ($\epsilon_m$ 15,100) and 339 n.m. (9.800); $\nu_{max}$. (CHCl$_3$) 3600–3200, 1790, 1730 and 1690 cm$^{-1}$; δ ppm (CDCl$_3$) 1.35 (d, J 6 Hz) and 1.36 (t, J 7 Hz) together 6H, 2.0 appox. (1H, brs), 2.80–3.15 (2H, m), 3.71 (1H, dd, J 1.6 and 6.6 Hz), 4.0–4.4 (1H, m), 5.18 and 5.46 (2H, ABq, J 14 Hz), 5.64 (1H, d, J 1.6 Hz), 7.60 (2H, d, J 8 Hz), 8.19 (2H, d, J 8 Hz), signals at 1.24 (t, J 7 Hz), 2.01 (s), and 4.09 (q, J 7 Hz) indicated the presence of approximately 0.5 mole of ethyl acetate of crystallisation; (Found: M$^+$, 410.0593. C$_{17}$H$_{18}$N$_2$O$_6$S$_2$ requires M, 410.0606). Evaporation of the mother liquors gave the (5RS,6RS,8SR)penem (15) (35 mg) contaminated with approximately 20% of the trans-isomer (14) as an amorphous solid, δ ppm (CDCl$_3$) (inter alia) 3.84 (0.8H, dd, J 3.9 and 10.1 Hz), 5.73 (0.8H, d, J 3.9 Hz).

EXAMPLE 1(a)

(5RS)-p-Nitrobenzyl(Z)-6-Ethylidene-2-ethylthiopenem-3-carboxylate

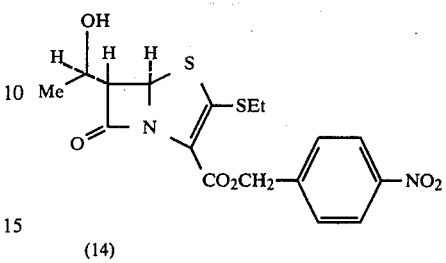

(14)

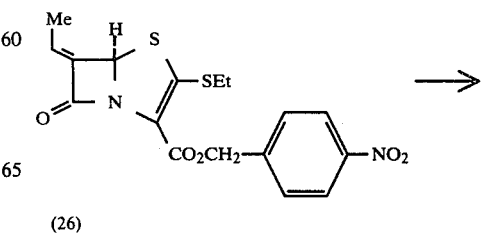

(26)

The trans-penem ester (14) (82 mg) was dissolved in dry methylene chloride (5 ml), cooled in an ice-bath, and treated with triphenylphosphine (52 mg) and diethyl azodicarboxylate (35 mg). The mixture was allowed to attain room temperature during fifteen minutes. The mixture was re-cooled in an ice-bath and treated with triphenylphosphine (52 mg) and diethyl azidocarboxylate (35 mg). The mixture was again allowed to attain room temperature during fifteen minutes and evaporated. The crude product was chromatographed on silica gel eluting with chloroform to give the (Z)-ethylidenepenem ester (26) (44 mg) as a solid, m.p. 169°–171° C. (fine yellow needles ex ethyl acetate/petrol), $\lambda_{max}$. (EtOH) 260 ($\epsilon_m$ 14,520) and 322 n.m. (7,980); $\nu_{max}$. (CHCl$_3$) 1785, 1700, br. cm$^{-1}$; δ ppm (CDCl$_3$) 1.36 (3H, t, J 7 Hz), 1.82 (3H, d, J 7 Hz), 2.75–3.15 (2H, m), 5.19 and 5.49 (2H, ABq, J 14 Hz), 6.16 (1H, s), 6.44 (1H, q, J 7 Hz, showing further fine coupling J <1 Hz), 7.63 (2H, d, J 8 Hz), 8.19 (2H, d, J 8 Hz). (Found: M$^+$, 392.0503. C$_{17}$H$_{16}$N$_2$O$_5$S$_2$ requires M, 392.0500).

EXAMPLE 1(b)

(5RS)-Sodium(Z)-6-Ethylidene-2-ethylthiopenem-3-carboxylate (26)

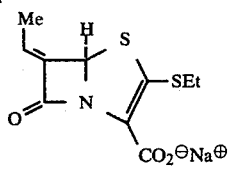

(27)

The (Z)-ethylidenepenem ester (26) (33 mg) was dissolved in a mixture of dioxan (8 ml) and water (2 ml) and hydrogenated over 5% palladium/charcoal catalyst (48 mg) at S.T.P. for one hour. Further catalyst (33 mg) was added and the hydrogenation continued for a further one and a half hours. A 1% sodium hydrogencarbonate solution (0.71 ml) was added and the mixture filtered through Kieselguhr, the residual catalyst being washed with a little 50% aqueous dioxan. The combined filtrates were evaporated and the residue chromatographed on Biogel P2 eluting with water. The appropriate fractions were evaporated and the residue re-evaporated from ethanol (2 ml) and dry toluene (2×2 ml) to give, after trituration with dry ether, the Z-ethylidenepenem sodium salt (27) (10 mg) as an amorphous solid, $\lambda_{max}$. (H$_2$O) 305 n.m. ($\epsilon_m$ 3280); δ ppm (D$_2$O) 1.19 (3H, t, J 7 Hz), 1.71 (3H, d, J 7 Hz), 2.4–3.1 (2H, m), 6.19 (1H, s), 6.44 (1H, q, J 7 Hz).

PREPARATION 2(a)

(3RS, 4SR)-3[1-(RS)-t-Butyldiphenylsilyloxyethyl]-4-methylsulphonylazetidin-2-one

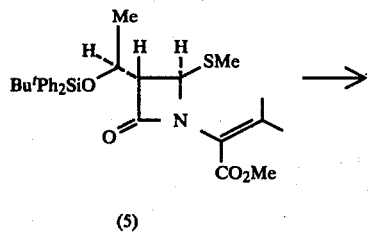

(5)

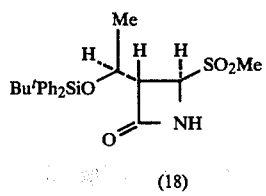

(18)

A solution of m-chloroperbenzoic acid (930 mg) in ethyl acetate (5 ml) was added dropwise over five minutes to a stirred, ice-bath cooled, solution of the impure azetidinone (5) (1.25 g) in ethyl acetate (25 ml). The mixture was kept at room temperature for one hour and washed with saturated sodium hydrogencarbonate solution (2×5 ml) and brine (3.×5 ml). The dried (MgSO$_4$) organic layer was treated with ozonised oxygen and methanol as in Preparation 1(e), to give, after chromatography, the sulphone (18) (894 mg) contaminated with 15% of the (3RS, 4SR)-3[1-(SR)-t-butyldiphenylsilyloxyethyl] isomer as a gum, $\nu_{max}$. (CHCl$_3$) 3420, 3270 br, 1790 cm$^{-1}$; δ ppm (CDCl$_3$) 1.01 and 1.05 (9H, each s), 1.27 (3H, d, J 6.1 Hz), 2.70 (0.85H, s), 2.91 (0.15H, s), 3.50–3.65 (1H, m), 4.15–4.50 (m) and 4.43 (d, J 2.0 Hz), together 1.85 H, 4.82 (0.15H, d, J 2 Hz), 6.92 (1H, broad s), 7.3–7.8 (10H, m).

PREPARATION 2(b)

(3RS, 4SR)-3[1-(RS)-t-Butyldiphenylsilyloxyethyl]-4-ethyl-thiothiocarbonylthioazetidin-2-one

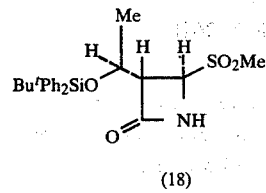

(18)

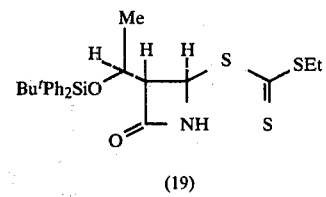

(19)

A mixture of the impure sulphone (18) (890 mg) in methylene chloride (15 ml) and potassium ethyl trithiocarbonate (400 mg) in water (3 ml) was stirred vigorously at room temperature. After eighteen hours the mixture was worked up as in Preparation 1(f) to give the trithiocarbonate (19)(450 mg) as a yellow gum, $\lambda_{max}$. (EtOH) 303 n.m. ($\epsilon_m$ 13,700); $\nu_{max}$. (CHCl$_3$) 3420, 1775 cm$^{-1}$; δ ppm (CDCl$_3$) 1.05 (9H, s), 1.23 (d, J 6 Hz) and 1.34 (t, J 7 Hz) together 6H, 3.15–3.45 (3H, m), 4.22 (1H, dq, J 3 and 6 Hz), 5.62 (1H, d, J 2 Hz), 6.59 (1H, brs), 7.3–7.8 (10H, m). (Found: M$^+$—Bu$^t$, 432.0580. C$_{20}$H$_{22}$NO$_2$S$_3$Si requires 432.0579). The starting sulphone (18) (252 mg) was also isolated in this experiment.

Treatment of the recovered sulphone (18) with fresh potassium ethyl trithiocarbonate gave the trithiocarbonate (19) (126 mg).

PREPARATION 2(c)

(3RS, 4SR)-3[1-(RS)-t-Butyldiphenylsilyloxyethyl]-4-ethyl-thiothiocarbonylthio-1(1-hydroxy-1-p-nitrobenzyloxycarbonyltmethyl)azetidin-2-one

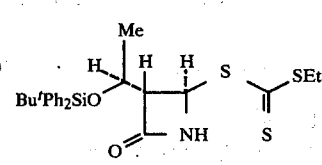

(19)

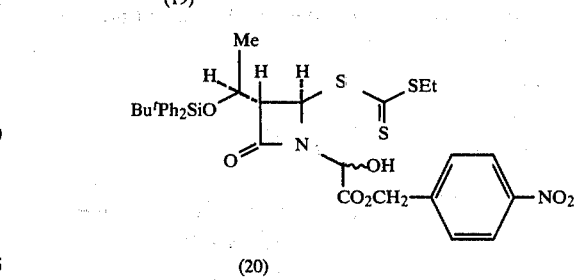

(20)

The trithiocarbonate (19) (570 mg) was treated with p-nitrobenzyl glyoxylate monohydrate (530 mg) as in Example 7 to give the hydroxy-ester (20) (676 mg), a mixture of stereoisomers, as an amorphous solid, $\nu_{max}$. (CHCl$_3$) 3520 br, 1780, 1760 slight shoulder cm$^{-1}$; δ ppm (CDCl$_3$) 1.0-1.5 (15H, m), 3.2-3.5 (3H, m), 3.75 (⅔H, d, J 9 Hz), 3.91 (⅓H, d, J 9 Hz), 4.1-4.5 (1H, m), 5.18-5.50 (⅔H, m), 5.56 (⅓H, d, J 9 Hz), 6.15-6.25 (1H, m), 7.2-7.8 (12H, m), 8.21 (2H, d, J 8 Hz).

PREPARATION 2(d)

(3RS, 4SR)-3[1-(RS)-t-Butyldiphenylsilyloxyethyl]-1-(1-chloro-1-p-nitrobenzyloxycarbonylmethyl)-4-ethylthio-thiocarbonylthioazetidin-2-one

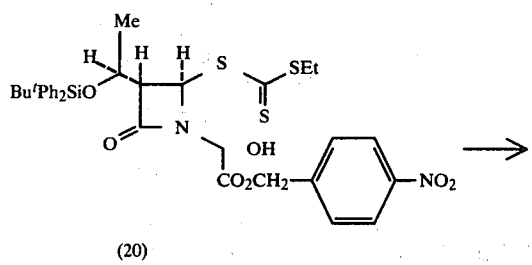

(20)

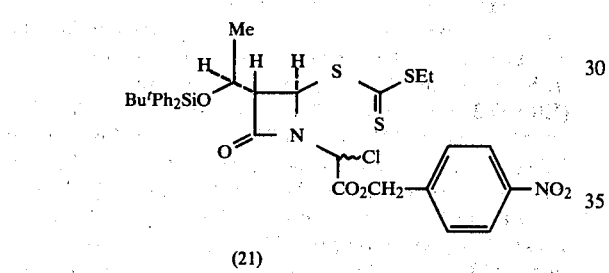

(21)

A solution of thionyl chloride (169 mg) in dry tetrahydrofuran (2 ml) was added, dropwise over three minutes, to a stirred mixture of the hydroxyester (20) (660 mg) and 2,6-lutidine (152 mg) in dry tetrahydrofuran (10 ml) at −10° C. The mixture was stirred at −10° C. for ten minutes, filtered, and evaporated. The residual gum was re-evaporated from dry toluene (2×2 ml) to give the chloro-ester (21) (679 mg) as a gum, $\nu_{max}$. (CHCl$_3$) 1790 cm$^{-1}$.

PREPARATION 2(e)

(3RS, 4SR)-3[1-(RS)-t-Butyldiphenylsilyloxyethyl]-4-ethyl-thiocarbonylthio-1-(1-p-nitrobenzyloxycarbonyl-1-triphenylphosphoranylidenemethyl)azetidin-2-one

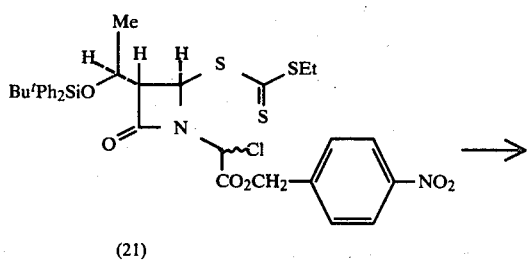

(21)

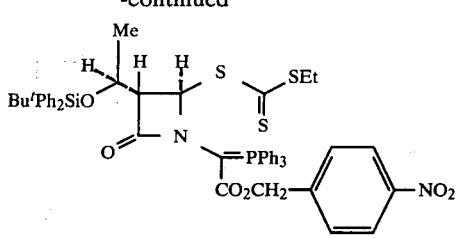

(22)

A mixture containing the chloro-ester (21) (679 mg), triphenylphosphine (1.02 g), and 2,6-lutidine (125 mg) in dry dioxan (15 ml) was stirred at 60° C. under dry argon for forty-eight hours. The mixture was worked up as in Preparation 1(i) to give the phosphorane (22) (640 mg) as an amorphous solid, $\nu_{max}$. (CHCl$_3$) 1750, 1620 cm$^{-1}$.

PREPARATION 2(f)

(5RS, 6SR, 8SR)-p-Nitrobenzyl 6(1-t-Butyldiphenylsilyloxyethyl)-2-ethylthiopenem-3-carboxylate

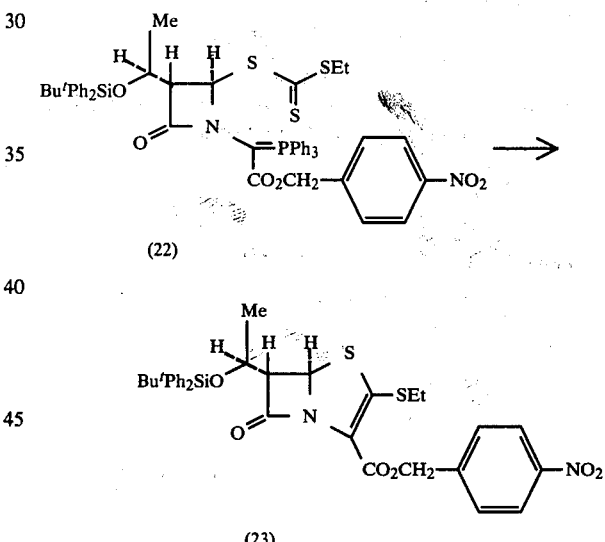

A solution of the phosphorane (22) (640 mg) in xylene (640 ml) was refluxed under argon for nine hours. The mixture was evaporated and the residue chromatographed on silica gel eluting with ethyl acetate/petroleum ether mixtures to give the penem ester (23) (229 mg) as a gum, $\lambda_{max}$. (EtOH) 261 ($\epsilon_m$ 13,800) and 339 n.m. (9, 600); $\nu_{max}$. (CHCl$_3$) 1790, 1690 cm$^{-1}$; δ ppm (CDCl$_3$) 1.00 (9H, s), 1.24 (3H, d, J 6 Hz), 1.34 (3H, t, J 7 Hz), 2.80-3.15 (2H, m), 3.71 (1H, dd, J 3.3 and 1.5 Hz), 4.00-4.40 (1H, m), 5.19 and 5.42 (2H, ABq, J 13 Hz), 5.53 (1H, d, J 1.5 Hz), 7.1-7.8 (12H, m), 8.14 (2H, d, J 8 Hz) (Found: M$^+$, 648.1776. C$_{33}$H$_{36}$N$_2$O$_6$S$_2$Si requires 648.1781).

PREPARATION 2(g)

(5RS, 6SR, 8SR)-p-Nitrobenzyl 2-Ethylthio-6(1-hydroxyethyl)penem-3-carboxylate

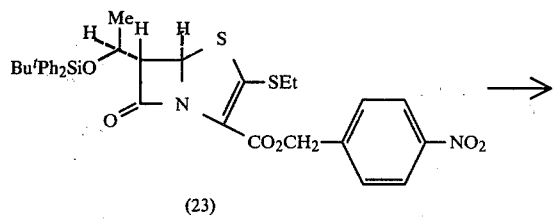

(23)

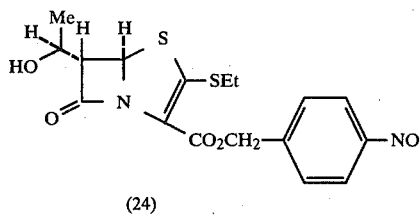

(24)

Tetra-n-butylammonium fluoride (1.39 ml of a solution containing 0.5 mMole n-Bu$_4$NF.3H$_2$O/ml tetrahydrofuran, dried over Molecular Sieves Type 4A for twenty-four hours) was added over five minutes to an ice-bath cooled solution of the penem silyl ether (23) (225 mg) in dry tetrahydrofuran (10 ml). The mixture was kept at ice-bath temperature for thirty minutes and then allowed to attain room temperature during a further thirty minutes. Work-up of the mixture as in Preparation 1(k) gave the trans-penem ester (24) (52 mg) as a solid, m.p. 170°–1° C. (yellow needles ex ethyl acetate/petroleum ether), $\lambda_{max}$. (EtOH) 261 ($\epsilon_m$ 15,700) and 340 nm (10,000); $\nu_{max}$. (CHCl$_3$) 1790, 1690 cm$^{-1}$; δ ppm (CDCl$_3$) 1.28–1.46 (6H, m), approx. 1.6 (1H, broad signal), 2.84–3.14 (2H, m), 3.85 (1H, dd, J 1.5 and 4.5 Hz) 3.95–4.45 (1H, m), 5.19 and 5.50 (2H, ABq, J 14 Hz), 5.63 (1H, d, J 1.5 Hz), 7.62 (2H, d, J 8.8 Hz), 8.21 (2H, d, J 8.8 Hz). (Found: M+, 410.0615. C$_{17}$H$_{18}$N$_2$O$_6$S$_2$ requires M, 410.0606).

EXAMPLE 2(a)

(5RS)-p-Nitrobenzyl (E)-6-Ethylidene-2-ethylthiopenem-3-carboxylate

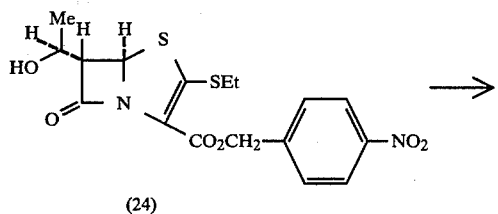

(24)

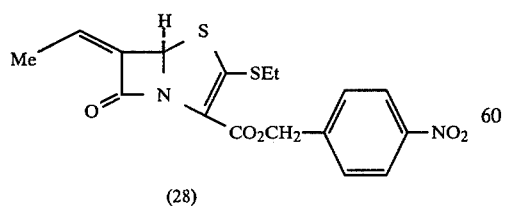

(28)

The trans-penem ester (100 mg) was dissolved in dry methylene chloride (10 ml), cooled in an ice-bath, and treated with triphenylphosphine (2×64 mg) and diethyl azodicarboxylate (2×42 mg) as in Example 1(a). The mixture was evaporated and chromatographed on silica gel eluting with ethyl acetate/petroleum ether mixtures to give the (E)-ethylidenepenem ester (28) (48 mg) as a solid, $\lambda_{max}$. (EtOH) 260 ($\epsilon_m$ 14,050) and 322 (7,640); $\nu_{max}$. (CHCl$_3$) 1780, 1690 cm$^{-1}$; δ ppm (CDCl$_3$) 1.35 (3H, t, J 7 Hz), 2.10 (3H, d, J 7 Hz), 2.8–3.1 (2H, m), 5.20 and 5.50 (2H, ABq, J 14 Hz), 5.98 (1H, q, J 7 Hz), 6.12 (1H, s), 7.64 (2H, d, J 8 Hz), 8.21 (2H, d, J 8 Hz). (Found: M+, 392.0463. C$_{17}$H$_{16}$N$_2$O$_5$S$_2$ requires M, 392.0500).

EXAMPLE 2(b)

(5RS)-Sodium (E)-6-Ethylidene-2-ethylthiopenem-3-carboxylate

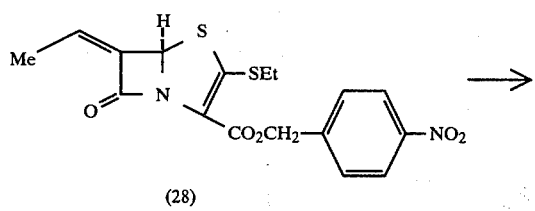

(28)

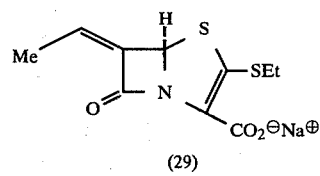

(29)

The (E)-ethylidenepenem ester (28) (45 mg) was dissolved in a mixture of dioxan (8 ml) and water (2 ml) and hydrogenated over 5% palladium/charcoal catalyst (68 mg) at S.T.P. for one hour. Further catalyst (45 mg) was added and the hydrogenation continued for a further two and a half hours. A 1% sodium hydrogencarbonate solution (0.96 ml) was added and the mixture worked up as in Example 1(b) to give the (E)-ethylidenepenem sodium salt (29) (14 mg) as an amorphous solid, $\lambda_{max}$. (H$_2$O) 212 ($\epsilon_m$ 8,410) and 306 n.m. (3, 180).

EXAMPLE 3(a)

(5RS, 6SR, 8RS)-p-Nitrobenzyl 2-Ethylthio-6-(1-methylsulphonyloxyethyl)penem-3-carboxylate

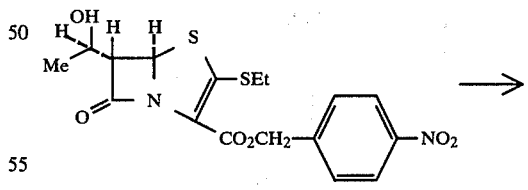

(14)

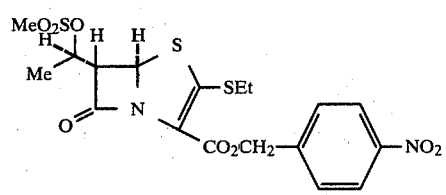

(30)

The trans-penem ester (14) (100 mg) was dissolved in dry methylene chloride (4 ml), cooled in an ice-bath, and treated with triethylamine (37 mg) and methanesulphonyl chloride (42 mg). The mixture was stirred for fifteen minutes and washed with brine. The dried (MgSO₄) organic layer was evaporated and the residue crystallised from ethyl acetate/petroleum ether to give the mesylate (30) (56 mg) as rods, m.p. 114°–116° C., $\nu_{max}$ (CHCl₃) 1795, 1695 cm⁻¹; δ ppm (CDCl₃) 1.37 (3H, t, J 7 Hz) 1.58 (3H, d, J 6½ Hz), 2.8–3.2 (m) and 3.01 (s) together 5H, 3.92 (1H, dd, J 1½ and 7½ Hz), 5.19 and 5.44 (ABq, J 13 Hz), partially obscuring a m, together 3H, 5.77 (1H, d, J 1½ Hz), 7.59 (2H, d, J 8½ Hz), 8.20 (2H, d, J 8½ Hz). (Found: M⁺, 488.0373. C₁₈H₂₀N₂O₈S₃ requires M, 488.0379).

EXAMPLE 3(b)

(5RS)-p-Nitrobenzyl (Z)-6-Ethylidene-2-ethylthiopenem-3-carboxylate

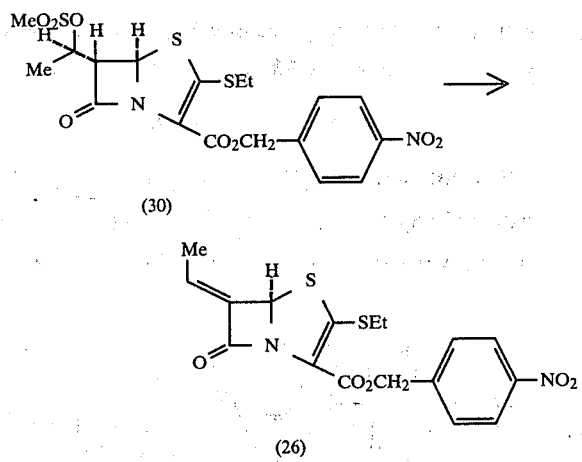

The mesylate (30) (2 mg) was dissolved in chloroform (0.2 ml) and treated with 1,5-diazabicyclo[4.3.0]non-5-ene (0.5 mg). The mixture was kept at room temperature for ten minutes and chromatographed to give the (Z)-ethylidene penem (26) (I.R. and U.V. data were in agreement with that described in Example 1(a).

PREPARATION 4(a)

(Z)-2-Carboethoxyvinylisothiuronium Chloride

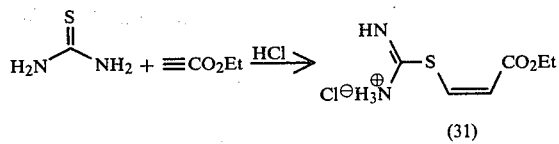

A solution containing ethyl propiolate (9.8 g) in methanol (20 ml) was added to a solution of thiourea (7.6 g) in 2N hydrochloric acid at a rate which allowed the temperature of the exothermic reaction to be maintained at approximately 50° C. After the addition was complete the mixture was stirred for 2 hours and evaporated. The residue was re-evaporated from dry toluene (3×20 ml) and crystallized from propan-2-ol to give the isothiuronium chloride (31) (14.2 g), mp 134°–136° C. (rods); $\nu_{max}$ (Nujol) 3600–2500, 1700, 1675, 1660 cm⁻¹; δ ppm [(CD₃)₂SO] 1.28 (3H, t, J 7 Hz), 3.69 br (1H, s, exch. D₂O), 4.26 (2H, q, J 7 Hz), 6.40 (1H, d, J 10 Hz), 7.96 (1H, d, J 10 Hz), 10.02 br (3H, s, exch. D₂O). (Found: C, 34.1; H, 5.2; N, 13.3; S, 15.2. C₆H₁₁N₂ClO₂S requires C, 34.2; H, 5.2; N, 13.3; S, 15.2%).

PREPARATION 4(b)

(3RS,4SR)-3[1-(SR)-t-Butyldiphenylsilyloxyethyl]-4-[2-(Z)-ethoxycarbonylvinylthio]azetidin-2-one

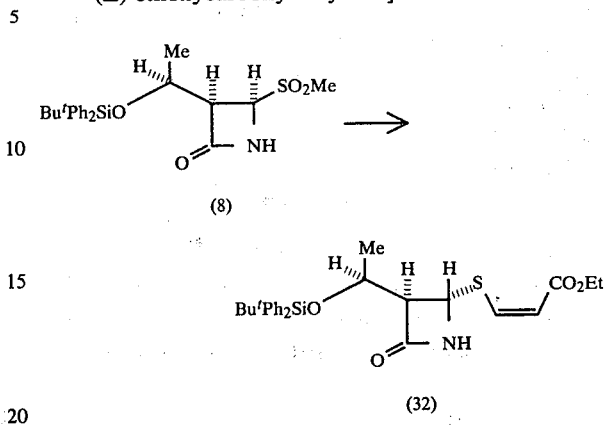

A 1N solution of sodium hydroxide (8.64 ml) was added, dropwise over 2 minutes, to a stirred solution of the isothiuronium chloride (31) (910 mg) in ethanol (20 ml) at −10° C. The resulting mixture was treated, in 2 minutes, with a pre-cooled (−10° C.) solution of the sulphone (8) (1.86 g) in ethanol (40 ml). After stirring at −10° C. for 30 minutes the mixture was allowed to attain room temperature (30 minutes), diluted with ethyl acetate (400 ml) and washed with brine (3×50 ml). The aqueous washings were back-extracted with ethyl acetate (50 ml). The dried (MgSO₄), combined, organic layers were evaporated and the residue chromatographed to give the azetidinone (32) (1.68 g) as an amorphous solid, $\nu_{max}$ (CHCl₃) 3410, 1775, 1695 cm⁻¹; δ ppm (CDCl₃) 1.00–1.20 (m) and 1.28 (t, J 7 Hz) together 15H, 3.15–3.28 (1H, m, sharpens to 3.22, dd, J 2.2 and 4.4 Hz on irradiation of the signal at 6.45 ppm), 4.1–4.4 (m) and 4.19 (q, J 7 Hz) together 3H, 4.92 (1H, d, J 2.2 Hz), 5.94 (1H, d, J 10 Hz), 6.45 (1H, s), 7.14 (1H, d, J 10 Hz), 7.3–7.8 (10H, m). (Found: [M—Buᵗ]⁺, 426.1201. C₂₂H₂₄NO₄SSi requires 426.1195).

PREPARATION 4(c)

(3RS,4SR)-3[1-(SR)-t-Butyldiphenylsilyloxyethyl]-4-[2-(Z)-ethoxycarbonylvinylthio]-1(1-hydroxy-1-p-nitrobenzyloxycarbonylmethyl)azetidin-2-one

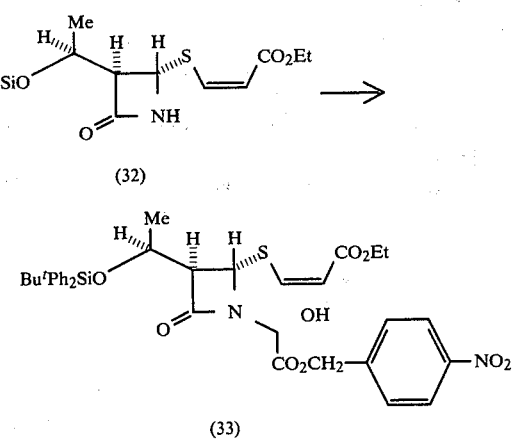

The azetidinone (32) (1.74 g) and p-nitrobenzyl glyoxylate monohydrate (1.63 g) were heated in refluxing benzene (40 ml) under argon for 7 hours with provision for removal of water. The mixture was evaporated and chromatographed to give the hydroxyester (33) (2.25 g), a mixture of stereoisomers, as an amorphous solid, $\nu_{max}$ (CHCl$_3$) 3520, 1775, 1760 sh, 1695 cm$^{-1}$; δ ppm (CDCl$_3$) 1.0–1.4 (15H, m), 3.15–3.30 (1H, m), 3.6–3.9 (1H, broad signal, exch. D$_2$O), 4.0–4.4 (3H, m), 5.0–5.7 (4H, m, simplifies on exch. D$_2$O), 5.82 and 5.87 (1H, each d, J 10 Hz), 7.02 and 7.11 (1H, each d, J 10 Hz), 7.3–7.8 (12H, m), 8.21 (2H, d, J 8.5 Hz).

PREPARATION 4(d)

(3RS,4SR)-3[1-(SR)-t-Butyldiphenylsilyloxyethyl]-1-(1-chloro-1-p-nitrobenzyloxycarbonylmethyl)-4-[2-(Z)-ethoxycarbonylvinylthio]azetidin-2-one

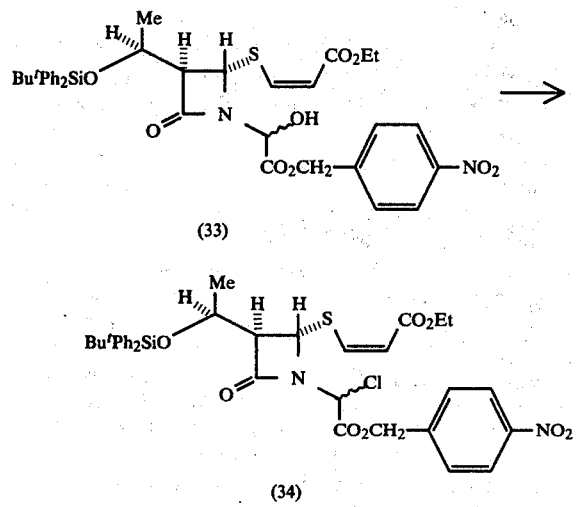

A solution of thionyl chloride (573 mg) in dry tetrahydrofuran (10 ml) was added, dropwise over 10 minutes, to a stirred mixture of the hydroxyester (33) (2.22 g) and 2,6-lutidine (515 mg) in dry tetrahydrofuran (40 ml) at −10° C. After stirring at −10° C. for a further 10 minutes the mixture was filtered and evaporated. The residue was re-evaporated from dry toluene to give the chloroester (34) (2.32 g) as a gum, $\nu_{max}$ (CHCl$_3$) 1785 br, 1695 cm$^{-1}$.

PREPARATION 4(e)

(3RS,4SR)-3-[1-(SR)-t-Butyldiphenylsilyloxyethyl]-4-[2-(Z)-ethoxycarbonylvinylthio]-1-(1-p-nitrobenzyloxycarbonyl-1-triphenylphosphoranylidenemethyl)azetidin-2-one

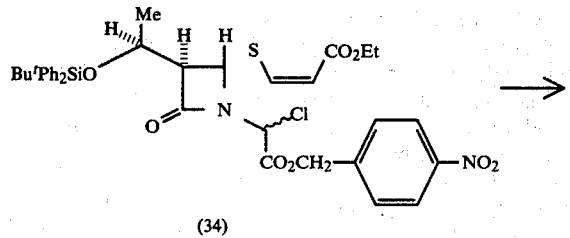

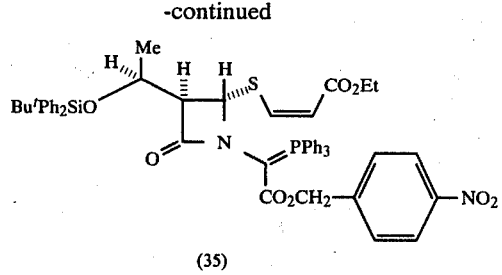

A mixture of the chloroester (34) (2.32 g), triphenylphosphine (3.42 g) and 2,6-lutidine (420 mg) in dry dioxane (40 ml) was heated at 60° C. under dry argon for 16 hours. The mixture was worked up as for preparation 1(i) to give the phosphorane (35) (2.82 g) as an amorphous solid, $\nu_{max}$ (CHCl$_3$) 1750, 1695, 1625 cm$^{-1}$.

PREPARATION 4(f)

(3RS,4SR)-4-[2-(Z)-Ethoxycarbonylvinylthio]-3-[1-(SR)-hydroxyethyl]-1-(1-p-nitrobenzyloxycarbonyl-1-triphenylphosphoranylidenemethyl)azetidin-2-one

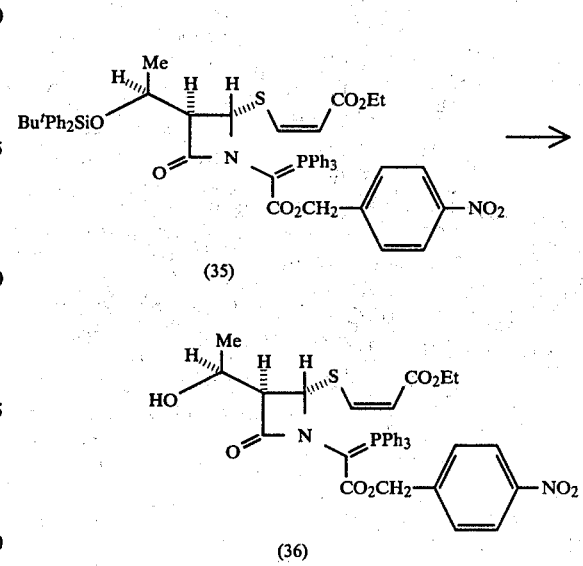

Hydrogen chloride was passed into an ice-bath cooled solution of the phosphorane (35) (1.32 g) in methanol (25 ml) until the concentration was approximately 15% w/v. The mixture was kept at room temperature for 3 hours, diluted with ethyl acetate (150 ml) and neutralised with saturated sodium bicarbonate solution. The organic layer was separated and washed with brine (3×25 ml). The dried (MgSO$_4$) organic layer was evaporated and the residue chromatographed to give the phosphorane (36) (745 mg) as an amorphous solid, $\nu_{max}$ (CHCl$_3$) 3700–3100, 1750, 1695, 1620 cm$^{-1}$.

PREPARATION 4(g)

(5RS,6SR,8RS)-p-Nitrobenzyl 6-(1-Hydroxyethyl)penem-3-carboxylate

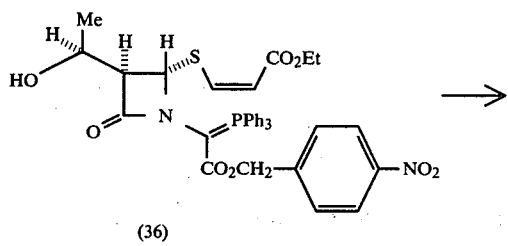

(36)

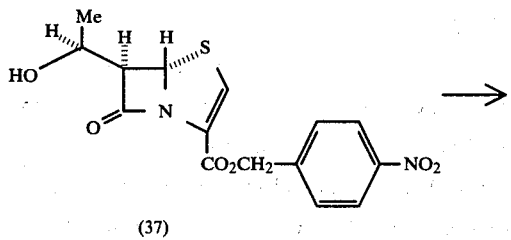

(37)

The phosphorane (36) (745 mg) was dissolved in ethyl acetate (15 ml) and treated with trifluoroacetic acid (3.27 ml) at room temperature. After 10 minutes the mixture was cooled to −76° C. and ozonised oxygen passed till a pale blue colour persisted. Excess ozonised oxygen was removed by passage of argon and the mixture was treated with a solution of triphenylphosphine (280 mg) in ethyl acetate (3 ml). The mixture was allowed to reach 0° C. and was neutralised with saturated sodium bicarbonate solution. The organic layer was separated and washed with brine (3×5 ml), dried (MgSO4) and heated at 50° C. under argon for 45 minutes. The mixture was evaporated and the residue chromatographed to give the penem ester (37) (293 mg) as a solid, m.p. 119°–120° C. (needles ex ethyl acetate/petroleum ether); $\lambda_{max}$(EtOH) 262 ($\epsilon_m$, 12730) and 317 nm (8490); $\nu_{max}$ (CHCl$_3$) 3600–3100, 1790, 1720 cm$^{-1}$; δ ppm (CDCl$_3$) 1.38 (3H, d, J 6.3 Hz), 2.10 (1H, d, J 4.7 Hz), 3.85 (1H, ddd, J 6.3, 1.5 and 1.0 Hz), 4.29 (1H, ddq, J 6.3, 6.3 and 4.7 Hz), 5.26 and 5.43 (2H, ABq, J 14 Hz), 5.79 (1H, d, J 1.5 Hz), 7.34 (1H, d, J 1.0 Hz), 7.59 (2H, d, J 8 Hz), 8.24 (2H, d, J 8 Hz). (Found: C, 51.1; H, 4.0; N, 7.8; S, 8.9; M+, 350.0557. C$_{15}$H$_{14}$N$_2$O$_6$S requires C, 51.4; H, 4.0; N, 8.0; S, 9.0% M, 350.0573).

EXAMPLE 4(a)

(5RS,6SR,8RS)-p-Nitrobenzyl 6-(1-methylsulphonyloxyethyl)penem-3-carboxylate

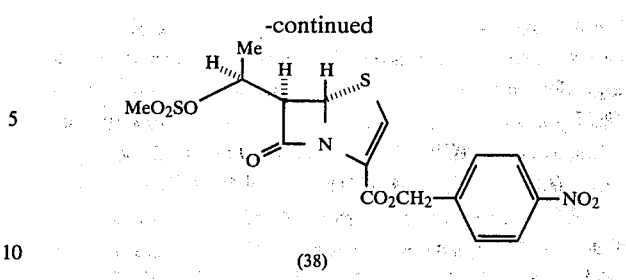

(37)

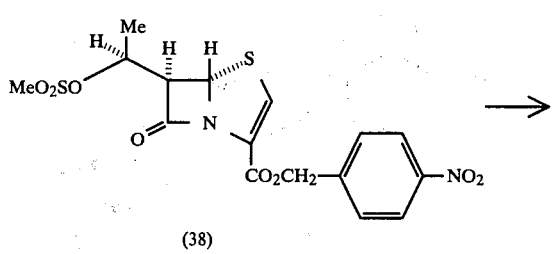

(38)

A solution of the penem ester (37) (145 mg) in methylene chloride (5 ml) was cooled to −10° C. and treated with triethylamine (84 mg) and methanesulphonyl chloride (95 mg). After stirring at −10° C. for 15 minutes the mixture was diluted with ethyl acetate (25 ml) and washed with brine (3×5 ml). The dried (MgSO4) organic layer was evaporated to give the crude mesylate (38) (191 mg) as a gum, $\nu_{max}$(CHCl$_3$) 1795, 1720 cm$^{-1}$; δ ppm (CDCl$_3$) 1.61 (3H, d, J 7 Hz), 3.28 (3H, s), 4.12 (1H, dd, J 2 and 7 Hz), 5.20 (dq, J 7 and 7 Hz) plus 5.28 and 5.52 (ABq, J 14 Hz) together 3H, 5.94 (1H, d, J 2 Hz), 7.46 (1H, s), 7.66 (2H, d, J 8 Hz), 8.29 (2H, d, J 8 Hz).

EXAMPLE 4(b)

(5RS)-p-Nitrobenzyl (Z)-6-Ethylidenepenem-3-carboxylate

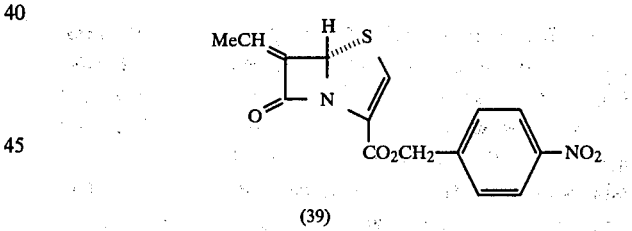

(38)

(39)

The crude mesylate (38) (191 mg) was dissolved in dry methylene chloride (5 ml), cooled to −10° C. and treated with a solution of 1,8-diazabicyclo[5.4.0]undec-7-ene (DBU) (63 mg) in dry methylene chloride (1 ml) dropwise over 1 minute. After stirring at −10° C. for 10 minutes the mixture was treated with DBU (25 mg). After stirring for a further 10 minutes at −10° C. the mixture was diluted with ethyl acetate (30 ml) and washed with 5% citric acid solution (3 ml), brine (2×3 ml), saturated sodium bicarbonate solution (3 ml), and brine (3×3 ml). The dried (MgSO4) organic layer was evaporated and the residue chromatographed to give the 6-ethylidenepenem ester (39) (113 mg), a 5:2 mixture of (Z) and (E)-isomers as determined by nmr. Fractional crystallisation of the mixture from ethyl acetate/petroleum ether afforded the pure (Z)-isomer, m.p. 164°–166° C. (rods); $\lambda_{max}$ (EtOH) 265 ($\epsilon_m$, 12010) and 296 nm (inflection); $\nu_{max}$ (CHCl$_3$) 1790 and 1720 cm$^{-1}$; δ ppm (CDCl$_3$) 1.86 (3H, d, J 7.1 Hz with further fine coupling), 5.28 and 5.45 (2H, ABq, J 13 Hz), 6.32 (1H, d, J 1.1 Hz with further fine coupling), 6.53 (1H, dq, J 7.1 and 1.1 Hz), 7.37 (1H, s), 7.61 (2H, d, J 9 Hz), 8.24 (2H, d, J 9 Hz). (Found: C, 54.2; H, 3.4; N, 8.3; S, 9.5; M+, 332.0474. $C_{15}H_{12}N_2O_5S$ requires C, 54.2; H, 3.6; N, 8.4; S, 9.6%; M, 332.0464).

EXAMPLE 4(c)
(5RS)-Sodium(Z)-6-Ethylidenepenem-3-carboxylate

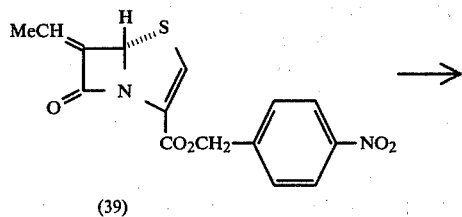

(39)

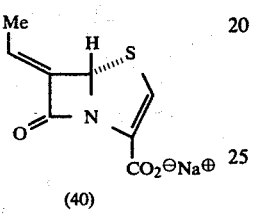

(40)

The (Z)-ethylidenepenem ester (39) (56 mg) was dissolved in a mixture of dioxan (8 ml) and water (2 ml) and hydrogenated over 5% palladium/charcoal catalyst (84 mg) at S.T.P. for 45 minutes. Further catalyst (56 mg) was added and the hydrogenation continued for 30 minutes. A 1% sodium bicarbonate solution (1.42 ml) was added and the mixture worked up as in example (1b) to give the sodium salt (40) (20 mg) as a buff-coloured amorphous solid, $\lambda_{max}$ ($H_2O$) 288 nm ($\epsilon_m$ 3590); $\nu_{max}$ (KBr) 3700–2300, 1765, 1700, 1600, 1560 sh.cm$^{-1}$; δ ppm ($D_2O$) 1.64 (3H, d, J 7 Hz), 6.20 (1H, s), 6.34 (1H, q, J 7 Hz), 6.90 (1H, s).

PREPARATION 5(a)
(3RS,4SR)-3[1-(SR)-t-Butyldiphenylsilyloxyethyl]-4-n-butyrylthioazetidin-2-one

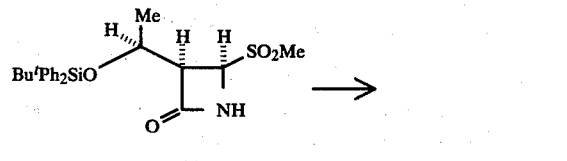

(8)

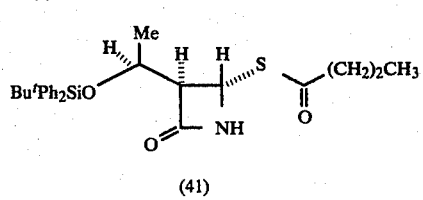

(41)

The sulphone (8) (2.00 g) was dissolved in dioxan (40 ml), cooled in an ice-bath, and treated with a solution of thiolbutyric acid (965 mg) in 1N sodium hydroxide (9.28 ml). The mixture was stirred at ice-bath temperature for 40 minutes, diluted with ethyl acetate and washed with brine. The dried (MgSO$_4$) organic layer was evaporated and chromatographed to give the thiolester (41) (1.73 g) as a solid, m.p. 82°–83° C. (rods ex petroleum ether); $\nu_{max}$ (CHCl$_3$) 3420, 1770, and 1690 cm$^{-1}$; δ ppm (CDCl$_3$) 0.95–1.15 (15H, m), 1.70 (2H, dq, J 7 and 7 Hz), 2.58 (2H, t, J 7 Hz), 3.14 (1H, dd, J 2.3 and 4.8 Hz), 4.25 (1H, dq, J 4.8 and 6 Hz), 5.30 (1H, d, J 2.3 Hz), 6.30 br (1H, s, exch. D$_2$O), 7.3–7.8 (10H, m). (Found: C, 66.3; H, 7.3; N, 3.0; S, 6.7; $C_{25}H_{33}NO_3SSi$ requires C, 65.9; H, 7.3; N, 3.1; S, 7.0%).

PREPARATION 5(b)
(3RS,4SR)-3[1-(SR)-t-Butyldiphenylsilyloxyethyl]-4-n-butyrylthio-1-(1-hydroxy-1-p-nitrobenzyloxycarbonyl-methyl)azetidin-2-one

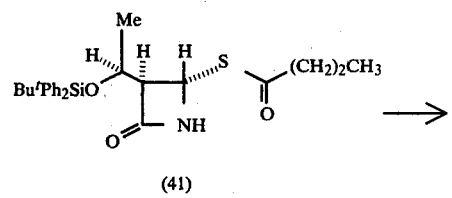

(41)

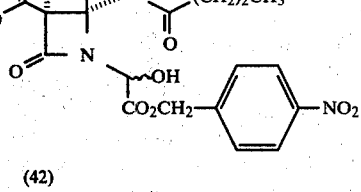

(42)

The thiolester (41) (1.80 g) and p-nitrobenzylglyoxylate monohydrate (1.80 g) were heated in refluxing benzene (40 ml) under argon for 7 hours with provision for removal of water. The mixture was evaporated and chromatographed to give a partial separation of the stereisomers of the hydroxyester (42). The less polar isomer was obtained as a gum (420 mg), $\nu_{max}$ (CHCl$_3$) 3600–3100, 1780, 1760, 1690 cm$^{-1}$; δ ppm (CDCl$_3$) 0.85–1.10 (15H, m), 1.40–1.85 (2H, m), 2.48 (2H, t, J 7 Hz), 3.20 (1H, dd, J 2.8 and 4.9 Hz), 4.24 (1H, dq, J 4.9 and 6 Hz), 4.41 (1H, d, J 11 Hz, exch. D$_2$O), 5.23 (2H, s), 5.53 (1H, d, J 11 Hz collapses to s on exch. D$_2$O), 5.58 (1H, d, J 2.8 Hz), 7.3–7.8 (12H,m), 8.20 (2H, d, J 9 Hz). The more polar isomer was also obtained as a gum (691 mg), $\nu_{max}$ (CHCl$_3$) 3600–3100, 1775, 1760 sh., 1700 cm$^{-1}$; δ ppm (CDCl$_3$) 0.85–1.10 (15H, m), 1.50–1.85 (2H, m), 2.58 (2H, t, J 7 Hz), 3.25 (1H, dd, J 2.7 and 4.9 Hz), 3.55–3.80 (1H, br signal, exch. D$_2$O), 4.25 (1H, dq, J 4.9 and 6 Hz), 5.15–5.50 (3H, m, collapses to 5.23, s, plus 5.22 and 5.41, ABq, J 13 Hz on exch. D$_2$O), 5.62 (1H, d, J 2.7 Hz), 7.3–7.8 (12H, m), 8.19 (2H, d, J 9 Hz). Also obtained was a mixture of the two stereoisiomers as a gum (884 mg).

PREPARATION 5(c)

(3RS,4SR)-3-[1-(SR)-t-Butyldiphenylsilyloxyethyl]-4-n-butyrylthio-1-(1-chloro-1-p-nitrobenzyloxycarbonyl-methyl)azetidin-2-one

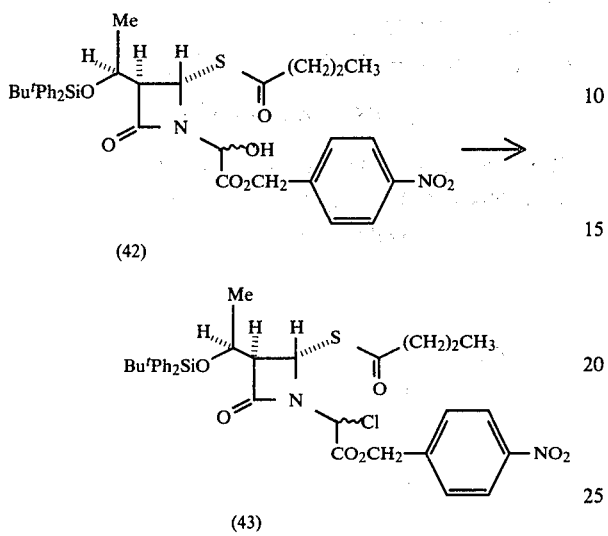

A solution of thionyl chloride (535 mg) in dry tetrahydrofuran (10 ml) was added, dropwise over 10 minutes, to a stirred mixture of the hydroxyester (42) (1.99 g) and 2,6-lutidine (482 mg) in dry tetrahydrofuran (40 ml) at −10° C. After stirring at −10° C. for a further 15 minutes, the mixture was filtered and the filtrate evaporated. The residue was re-evaporated from dry toluene (2×5 ml) to give the chloroester (43) (2.08 g) as a gum, $\nu_{max}$ (CHCl$_3$) 1785 br, 1700 cm$^{-1}$.

PREPARATION 5(d)

(3RS,4SR)-3-[1-(SR)-t-Butyldiphenylsilyloxyethyl]-4-n-butyrylthio-1-(1-p-nitrobenzyloxycarbonyl-1-triphenylphosphoranylidenemethyl)azetidin-2-one

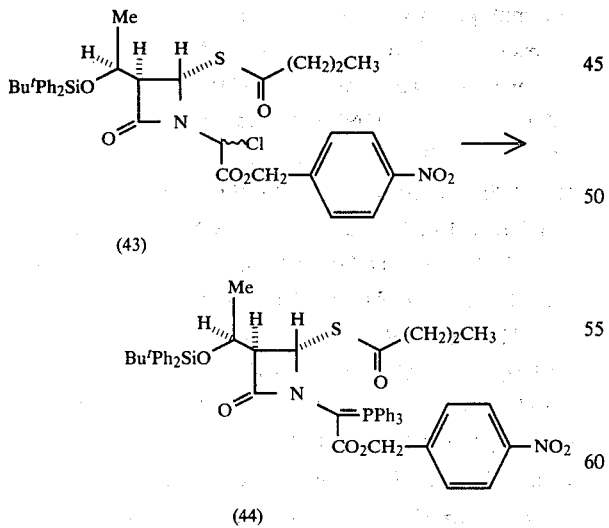

A mixture of the chloroester (43) (2.08 g), triphenylphosphine (3.14 g) and 2,6-lutidine (384 mg) in dry dioxan (40 ml) was heated at 60° C. under dry argon for 22 hours. The mixture was worked up as for preparation 1(i) to give the phosphorane (44) (1.46 g) as an amorphous solid, $\nu_{max}$ (CHCl$_3$) 1750, 1695, 1620 and 1610 sh. cm$^{-1}$. The chloroester (43) (587 mg) which was recovered from this experiment was retreated with triphenylphosphine (900 mg) and 2,6-lutidine (111 mg) in dioxan (10 ml) at 60° C. for 30 hours to give, after work-up, the phosphorane (44) (490 mg).

PREPARATION 5(e)

(5RS,6SR,8RS)-p-Nitrobenzyl 6-(1-t-Butyldiphenylsilyloxyethyl)-2-n-propylpenem-3-carboxylate

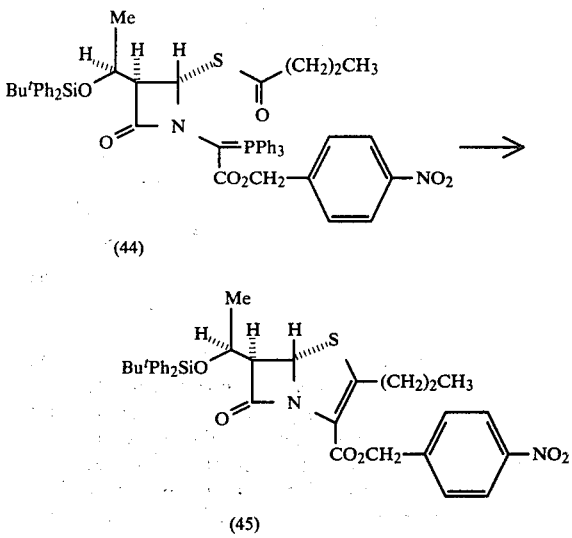

The phosphorane (44) (1.75 g) was heated in refluxing toluene (400 mg) under dry argon for 12 hours. The mixture was evaporated and chromatographed to give the penem ester (45) (960 mg) as a solid, m.p. 121°–123° C. (rods ex ethyl acetate/petroleum ether); $\lambda_{max}$ (EtOH) 264 ($\epsilon_m$, 12,285) and 316 nm (8435); $\nu_{max}$ (CHCl$_3$) 1785, 1710 cm$^{-1}$; δ ppm (CDCl$_3$) 0.85–1.35 (m) plus 1.01 (s) and 1.16 (d, J 6 Hz) together 15H, 1.40–1.80 (2H, m), 2.50–3.08 (2H, m), 3.72 (1H, dd, J 5.5 and 2 Hz), 4.23 (1H, dq, J 5.5 and 6 Hz), 5.15 and 5.43 (2H, ABq, J 14 Hz), 5.46 (1H, d, J 2 Hz), 7.3–7.8 (12H, m), 8.16 (1H, d, J 8.5 Hz). (Found: C, 64.7; H, 6.2; N, 4.4; S, 5.0. C$_{34}$H$_{38}$N$_2$O$_6$SSi requires C, 64.8; H, 6.0; N, 4.4; S, 5.1%).

PREPARATION 5(f)

(5RS,6SR,8RS)-p-Nitrobenzyl 6-(1-Hydroxyethyl)-2-n-propylpenem-3-carboxylate

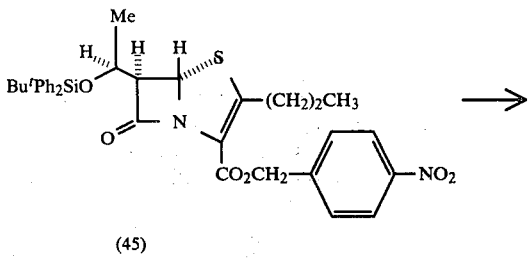

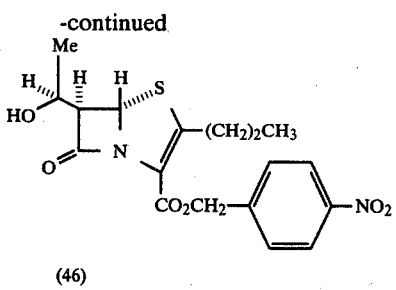

(46)

Tetra-n-butylammonium fluoride (6.04 ml of a solution containing 0.5 m.Mole n-Bu₄NF.3H₂O/ml in tetrahydrofuran, dried over molecular sieves Type 4A for 24 hours) was added over five minutes to a stirred, ice-bath cooled, solution of the penem ester (45) (950 mg) in dry tetrahydrofuran (20 ml). The mixture was kept at ice-bath temperature for 30 minutes and then allowed to attain room temperature during a further 30 minutes. The mixture was worked up as for Example 1(k) to give the hydroxyethylpenem ester (46) (190 mg) as a solid, m.p. 118°–119° C. (needles ex ethyl acetate/petroleum ether); $\lambda_{max}$ (EtOH) 263 (em 12,720) and 316 nm (9,380); $\nu_{max}$ (CHCl₃) 3630–3150, 1785, 1710 cm⁻¹; δ ppm (CDCl₃) 0.96 (3H, t, J 7 Hz), 1.37 (d, J 6 Hz) overlaying 1.3–1.8 (m) together 5H, 2.03 (1H, broad signal), 2.69 and 2.93 (2H, each dt, J 14 and 7 Hz), 3.71 (1H, dd, J 1.6 and 6.4 Hz), 4.0–4.5 (1H, m, simplifies on irradiation of signal at 2.03 ppm), 5.19 and 5.47 (2H, ABq, J 14 Hz), 5.59 (1H, d, J 1.6 Hz), 7.62 (2H, d, J 8 Hz), 8.22 (2H, d, J 8 Hz). (Found: C, 55.1; H, 5.3; N, 7.2. C₁₈H₂₀N₂O₆S requires C, 55.1; H, 5.1; N, 7.1%).

EXAMPLE 5(a)

(5RS,6SR,8RS)-p-Nitrobenzyl 6-(1-Methylsulphonyloxyethyl)2-n-propylpenem-3-carboxylate

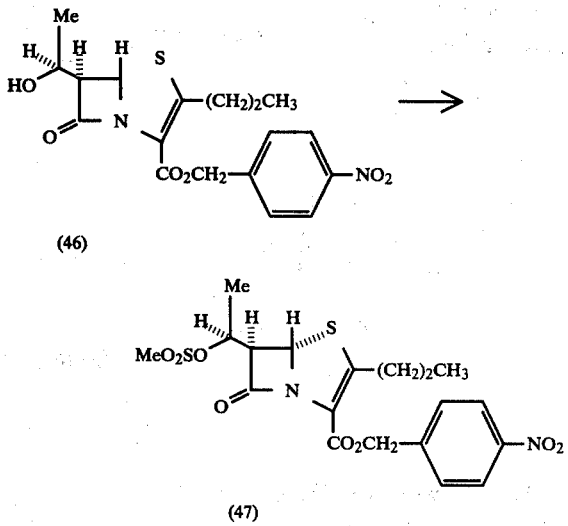

A solution of methanesulphonyl chloride (88 mg) in dry methylene chloride (1 ml) was added dropwise over 1 minute to a stirred mixture of the hydroxyethylpenem ester (46) (150 mg) and triethylamine (77 mg) in dry methylene chloride (5 ml) with cooling at −10° C. After 20 minutes at −10° C. the mixture was diluted with ethyl acetate (20 ml) and washed with brine (3×2 ml). The dried (MgSO₄) organic layer was evaporated to give the crude mesylate (47) (181 mg) as a gum, $\nu_{max}$ (CHCl₃) 1785, 1715 cm⁻¹.

EXAMPLE 5(b)

(5RS)-p-Nitrobenzyl (Z)-6-Ethylidene-2-n-propylpenem-3-carboxylate

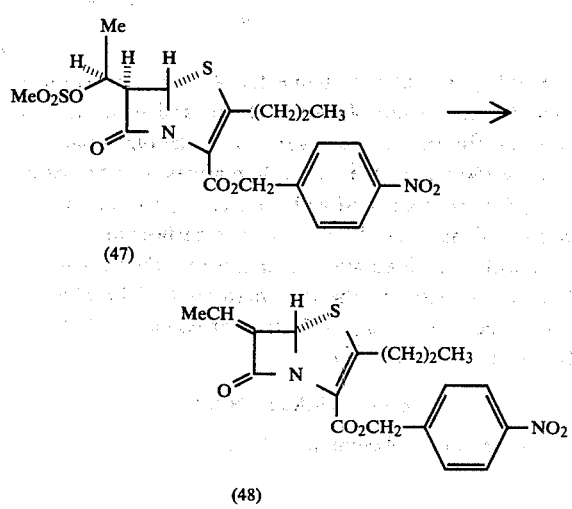

The crude mesylate (47) (181 mg) was dissolved in dry methylene chloride (5 ml), cooled to −10° C., and treated with a solution of 1,8-diazobicyclo-[5.4.0]undec-7-ene (58 mg) in dry methylene chloride (1 ml) dropwise over 1 minute. After stirring at −10° C. for 10 minutes the mixture was treated with DBU (23 mg). The mixture was stirred at −10° C. for a further 10 minutes, diluted with ethyl acetate (20 ml) and washed with 5% citric acid (2 ml), brine (2 ml), saturated sodium bicarbonate solution (2 ml) and brine (3×2 ml). The dried (MgSO₄) organic layer was evaporated and chromatographed to give the 6-ethylidenepenem ester (48) (116 mg), a mixture of (Z) and (E)-isomers, as a gummy solid. Fractional crystallisation of the mixture from ethyl acetate/petroleum ether gave pure (Z)-isomer (42 mg), m.p. 101°–102° C. (rods), $\lambda_{max}$ (EtOH) 267 ($\epsilon_m$ 12,190) and approximately 296 nm (10,500); $\nu_{max}$ (CHCl₃) 1775 and 1710 cm⁻¹; δ ppm (CDCl₃) 0.92 (3H, t, J 7 Hz), 1.35–1.70 (2H, m), 1.79 (3H, d, J 7 Hz), 2.50–3.00 (2H, m), 5.16 and 5.44 (2H, ABq, J 14 Hz), 6.06 (1H, slightly broadened s), 6.41 (1H, dq, J 7 and approximately 1 Hz), 7.60 (2H, d, J 8 Hz), 8.19 (2H, d, J 8 Hz). (Found: M⁺, 374.0900. C₁₈H₁₈N₂O₅S requires M, 374.0936).

EXAMPLE 5(c)

(5RS)-Sodium(Z)-6-Ethylidene-2-n-propylpenem-3-carboxylate

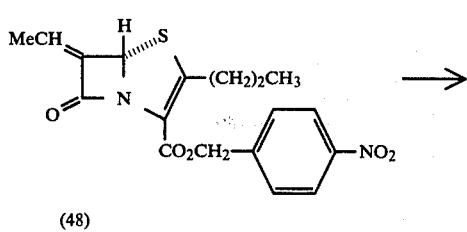

(48)

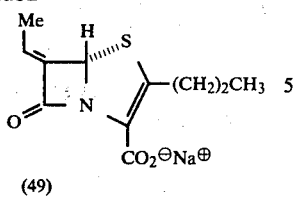

(49)

The (Z)-ethylidenepenem ester (48) (40 mg) was dissolved in a mixture of dioxan (8 ml) and water (2 ml) and was hydrogenated over 5% palladium/charcoal catalyst (60 mg) at S.T.P. for 30 minutes. Further catalyst (40 mg) was added and the hydrogenation continued for 30 minutes. A 1% sodium bicarbonate solution (0.90 ml) was added and the mixture worked up as for Example 1(b) to give the sodium salt (49) (4.4 mg) as an amorphous solid, $\lambda_{max}$ (H$_2$O) approximately 270 ($\epsilon_m$ 5610) and 288 nm (5940).

PREPARATION 6(a)

Potassium 2-Acetamidoethyltrithiocarbonate

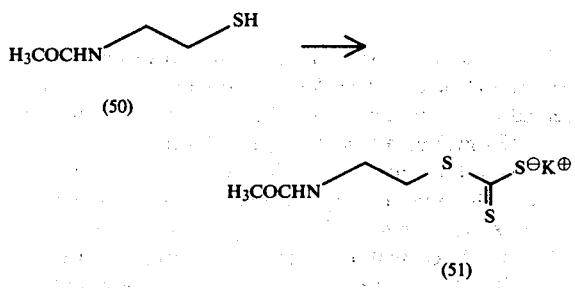

2-Acetamidoethanethiol (50) (3.57 g) was added to a solution of potassium hydroxide (1.62 g) in ethanol (25 ml) at room temperature. After 15 minutes the stirred mixture was cooled in an ice-bath and treated with carbon disulphide (3.6 ml). After 15 minutes at ice-bath temperature the stirred mixture was allowed to attain room temperature during 30 minutes. The yellow solid which had crystallised was filtered, washed with dry ether, and dried under vacuum to give the trithiocarbonate (51) (4.79 g), $\nu_{max}$ (Nujol) 3390, and 1640 cm$^{-1}$; $\delta$ ppm [(CD$_3$)$_2$SO] 1.82 (3H, s), 3.0–3.4 (4H, m), 8.1 (1H, broad signal, exch. D$_2$O). (Found: C, 25.6; H, 3.4; N, 5.8; S, 41.0. C$_4$H$_8$NOS$_3$K requires C, 25.8; H, 3.4; N, 6.0; S, 41.2%).

PREPARATION 6(b)

(3RS,4SR)-4(2-Acetamidoethylthiothiocarbonylthio)-3-[1-(SR)-t-butyldiphenylsilyloxyethyl]azetidin-2-one

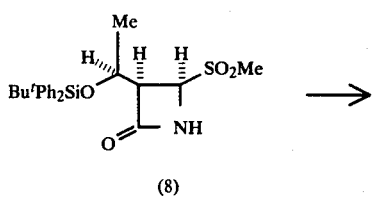

(8)

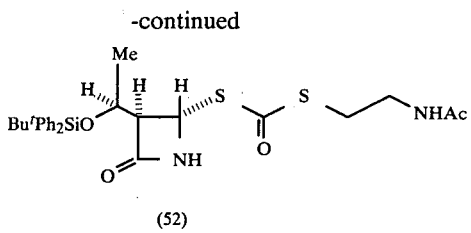

(52)

The sulphone (8) (2.05 g) was dissolved in methylene chloride (20 ml) and was treated with a solution of potassium 2-acetamidoethyltrithiocarbonate (51) (2.22 g) in water (4 ml). The mixture was stirred at room temperature for 4 hours, diluted with methylene chloride (20 ml) and washed with brine (10 ml). The dried (MgSO$_4$) organic layer was evaporated and the residue chromatographed to give the trithiocarbonate (52) (1.20 g) as an amorphous solid, $\lambda_{max}$ (CH$_3$CN) 302 nm ($\epsilon_m$ 12,880); $\nu_{max}$ (CHCl$_3$) 3440, 3400, 1775, 1670 cm$^{-1}$; $\delta$ ppm (CDCl$_3$) 1.05–1.15 (12H, m), 1.98 (3H, s), 3.21 (1H, dd, J 2.5 and 4.5 Hz), 3.5–3.6 (4H, m), 4.1–4.4 (1H, m), 5.67 (1H, d, J 2.5 Hz), 5.75–6.0 (1H, broad signal, exch. D$_2$O), 6.70 br (1H, s, exch. D$_2$O), 7.3–7.8 (10H, m).

PREPARATION 6(c)

(3RS,4SR)-4-(2-Acetamidoethylthiothiocarbonylthio)-3-[1-(SR)-t-butyldiphenylsilyloxyethyl]-1-(1-hydroxy-1-p-nitrobenzyloxycarbonylmethyl)azetidin-2-one

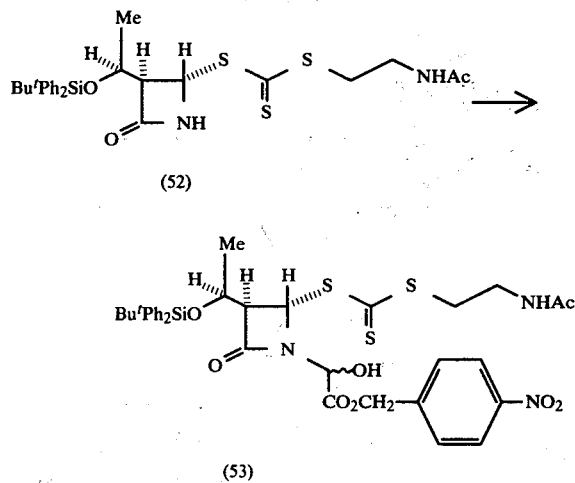

The trithiocarbonate (52) (1.26 g) and p-nitrobenzyl glyoxylate monohydrate (1.05 g) were heated in refluxing benzene (25 ml) under argon for 24 hours with provision for removal of water. The mixture was evaporated and chromatographed to give the hydroxyester (53) (1.04 g), a mixture of stereo-isomers, as an amorphous solid, $\nu_{max}$ (CHCl$_3$) 3600–3000, 1775, 1755 slight shoulder, 1670 cm$^{-1}$.

PREPARATION 6(d)

(3RS,4SR)-4-(2-Acetamidoethylthiothiocarbonylthio)-3-[1-(SR)-t-butyldiphenylsilyloxyethyl]-1-(1-chloro-1-p-nitrobenzyloxycarbonylmethyl)azetidin-2-one

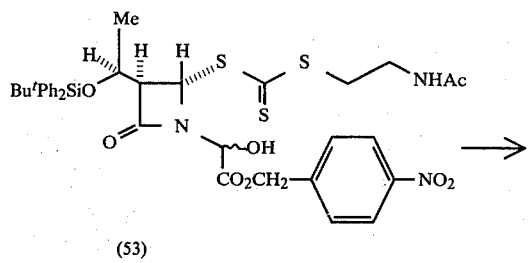

(53)

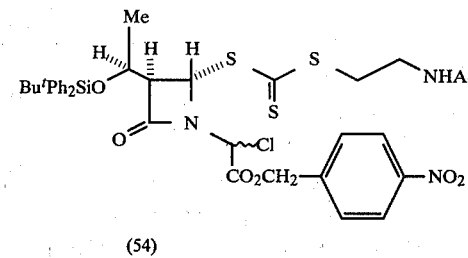

(54)

A solution of thionyl chloride (246 mg) in dry tetrahydrofuran (5 ml) was added, dropwise in 5 minutes, to a stirred mixture of the hydroxyester (53) (1.04 g) and 2,6-lutidine (221 mg) in dry tetrahydrofuran (20 ml) at −10° C. After stirring at −10° C. for 15 minutes the mixture was filtered and the filtrate evaporated. The residue was re-evaporated from dry toluene (2×5 ml) to give the chloroester (54) (1.04 g) as an amorphous solid, $\nu_{max}$ (CHCl$_3$) 3430, 1785, 1760 slight shoulder, 1670 cm$^{-1}$.

PREPARATION 6(e)

(3RS,4SR)-4-(2-Acetamidoethylthiothiocarbonylthio)-3-[1-(SR)-t-butyldiphenylsilyloxyethyl]-1-(1-p-nitrobenzyloxycarbonyl-1-triphenylphosphoranylidenemethyl)azetidin-2-one

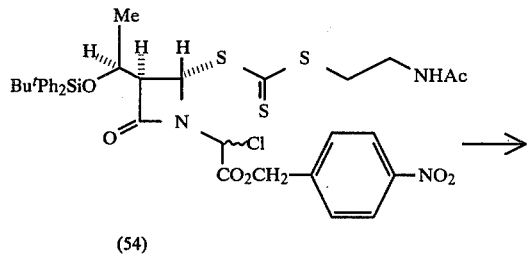

(54)

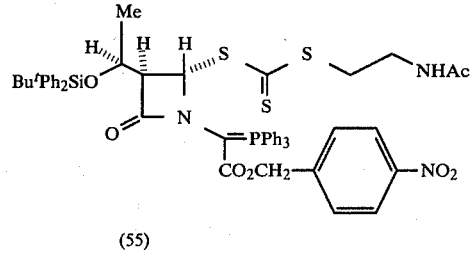

(55)

A mixture of the chloroester (54) (1.04 g), triphenylphosphine (1.44 g) and 2,6-lutidine (177 mg) was heated in dry dioxan (20 ml) at 60° C. under dry argon for 32 hours. The mixture was worked up as for preparation 1(i) to give the phosphorane (55) (662 mg) as an amorphous solid, $\nu_{max}$ (CHCl$_3$) 3430, 1755, 1670, 1620, 1605 shoulder cm$^{-1}$. Also obtained was recovered chloroester (54) (245 mg) which was recycled to give the phosphorane (55) (195 mg).

PREPARATION 6(f)

(3RS,4SR)-4-(2-Acetamidoethylthiothiocarbonylthio)-3-[1-(SR)-hydroxyethyl]-1-(1-p-nitrobenzyloxycarbonyl-1-triphenylphosphoranylidenemethyl)azetidin-2-one

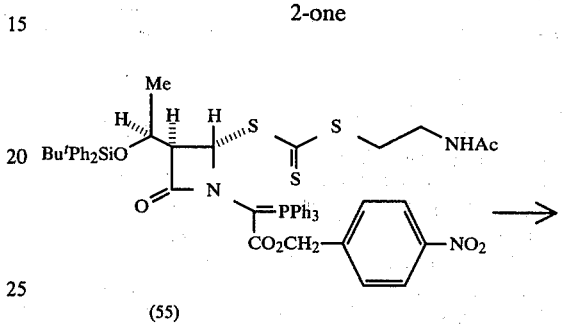

(55)

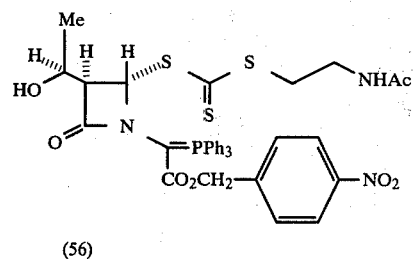

(56)

The phosphorane (55) (800 mg) was dissolved in methanolic hydrogen chloride (15% w/v HCl, 20 ml) and the mixture kept at room temperature for 7 hours. The mixture was diluted with ethyl acetate and neutralised with saturated sodium bicarbonate solution. The organic layer was separated and washed with brine. The dried (MgSO$_4$) organic layer was evaporated and chromatographed to give the phosphorane (56) (397 mg) as an amorphous solid, $\nu_{max}$ (CHCl$_3$) 3600–3100, 1755, 1670, 1625, 1610 shoulder cm$^{-1}$.

PREPARATION 6(g)

(5RS,6SR,8RS) and (5RS,6RS,8SR)-p-Nitrobenzyl 2-(2-Acetamidoethylthio)-6-(1-hydroxyethyl)penem-3-carboxylate

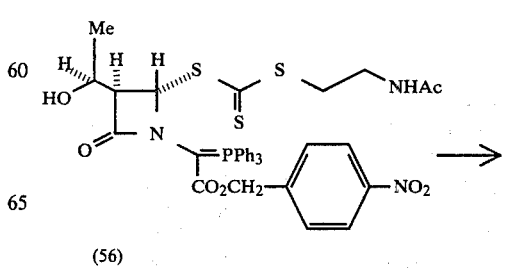

(56)

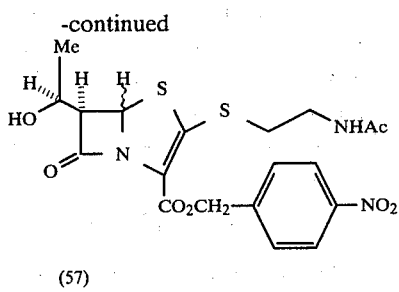

(57)

The phosphorane (56) (375 mg) was heated in refluxing xylene (375 ml) under dry argon for 5 hours. The mixture was evaporated and the residue chromatographed to give a mixture of the cis and trans isomers of the hydroxyethylpenem (57) (150 mg). Fractional crystallisation of the mixture from methanol gave the pure (5RS,6SR,8RS) isomer of the penem ester (57) (50 mg) as needles, m.p. 199°–202° C.; $\lambda_{max}$ (EtOH) 261 ($\epsilon_m$ 12,360) and 338 nm (7,760); $\nu_{max}$ (Nujol) 3520, 3290, 1800, 1670 and 1635 cm$^{-1}$; δ ppm [(CD$_3$)$_2$SO]1.17 (3H, d, J 6 Hz), 1.80 (3H, s), 2.95–3.17 (2H, m), 3.26–3.36 (2H, m), 3.86 (1H, dd, J 1.5 and 5.5 Hz), 3.92–4.06 (1H, m, collapsing to dq, J 5.5 and 6 Hz on exch. D$_2$O), 5.2–5.5 (3H, m, 1H exch. D$_2$O leaving 5.28 and 5.33, 2H, ABq, J 14 Hz), 5.74 (1H, d, J 1.5 Hz), 7.68 (2H, d, J 8 Hz), 8.15 (1H, t, J 5 Hz, exch. D$_2$O), 8.23 (2H, d, J 8 Hz). (Found: C, 48.6; H, 4.4; N, 8.7. $C_{19}H_{21}N_3O_7S_2$ requires C, 48.8; H, 4.5; N, 9.0%). Evaporation and rechromatography of the mother liquors gave the impure (5RS,6RS,8SR) isomer (57) (53 mg), δ ppm [(CD$_3$)$_2$CO] (inter alia) 1.51 (3H, d, J 6 Hz), 2.01 (3H, s), 4.12 (1H, dd, J 4.0 and 10.5 Hz), 4.28–4.45 (1H, m), 4.54 (1H, d, J 5.5 Hz), 5.98 (1H, d, J 4.0 Hz).

EXAMPLE 6(a)

(5RS)-p-Nitrobenzyl 2-(2-Acetamidoethylthio)-6-ethylidenepenem-3-carboxylate

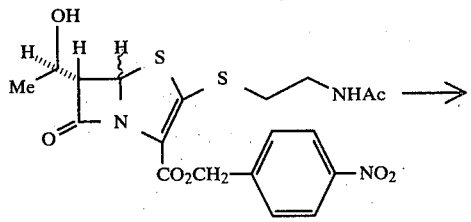

(57)

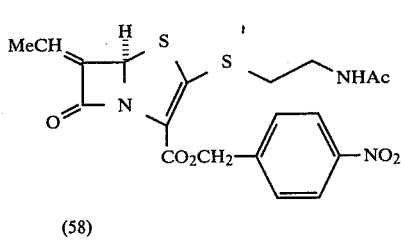

(58)

The (5RS,6SR,8RS) isomer of the penem ester (57) (40 mg) was suspended in dry dioxan (10 ml), cooled in an ice-water bath, and treated with triethylamine (17 mg) and methanesulphonyl chloride (20 mg). After stirring at room temperature for 30 minutes the mixture was treated with a further 1 equivalent of each reagent. The mixture was stirred for a further 30 minutes, cooled in an ice-water bath and treated with 1,8-diazabicyclo[5.4.0]undec-7-ene (DBU) (39 mg). The mixture was allowed to attain room temperature, stirred for 10 minutes, and treated with further DBU (26 mg). After stirring at room temperature for 20 minutes the mixture was evaporated to low volume, diluted with ethyl acetate (20 ml) and washed successively with 5% citric acid (4 ml), brine (4 ml), saturated NaHCO$_3$ solution (4 ml) and brine (3×4 ml). The dried (MgSO$_4$) organic layer was evaporated and chromatographed to give the ethylidenepenem ester (58) (26 mg), a 2:1 mixture of (E) and (Z) isomers, as an amorphous solid, $\lambda_{max}$ (EtOH) 265 and 318 nm; $\nu_{max}$ (CHCl$_3$) 3440, 1780 and 1675 cm$^{-1}$; δ ppm (CDCl$_3$) 1.84 and 2.10 (3H, each d, J 7 Hz), 1.94 (3H, s), 2.95–3.65 (4H, m), 5.19 and 5.49 (2H, ABq, J 13 Hz), 6.02 (⅔H, q, J 7 Hz), 6.13 and 6.17 (1H, each s), 6.46 (⅓H, q, J 7 Hz), 7.4–7.8 (3H, broad signal plus d, J 9 Hz), 8.21 (2H, d, J 9 Hz).

Similar treatment of the impure (5RS,6RS,8SR) isomer of the penem ester (57) (40 mg) gave a 4:1 mixture of the (E) and (Z) isomers of the ethylidenepenem ester (58) (18 mg).

EXAMPLE 6(b)

(5RS)-Sodium 2-(2-Acetamidoethylthio)-6-ethylidenepenem-3-carboxylate

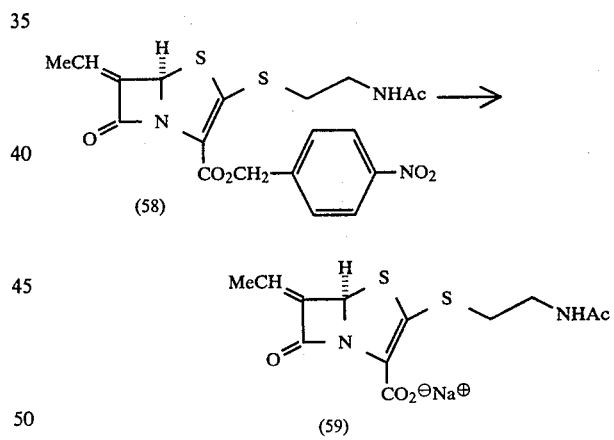

(58)

(59)

The ethylidenepenem ester (58) (40 mg) was dissolved in a mixture of dioxan (8 ml) and water (2 ml) and hydrogenated over 5% palladium/charcoal catalyst (60 mg) at S.T.P. for 40 minutes. Further catalyst (40 mg) was added and the hydrogenation continued for 30 minutes. A 1% sodium bicarbonate solution (0.75 ml) was added and the mixture worked up as for Example 1(b) to give the sodium salt (59) (9.9 mg), a 2:1 mixture of (E) and (Z) isomers, as an amorphous solid, $\lambda_{max}$ (H$_2$O)302 nm; δ ppm (D$_2$O) 1.83 (⅓ CH$_3$, d, J 7 Hz), 1.98 (3H, s), 2.04 (⅔ CH$_3$, d, J 7 Hz), 2.87–3.20 (2H, m), 3.35–3.55 (2H, m), 6.18 (⅔H, s), 6.20 (⅔H q, J 7 Hz), 6.27 (⅓H, s), 6.54 (⅓H, q, J 7 Hz).

PREPARATION 7(a)

3-(1-Acetoxyethyl)-1-(1-methoxycarbonyl-2-methyl-prop-1-enyl)-4-methylthioazetidin-2-one

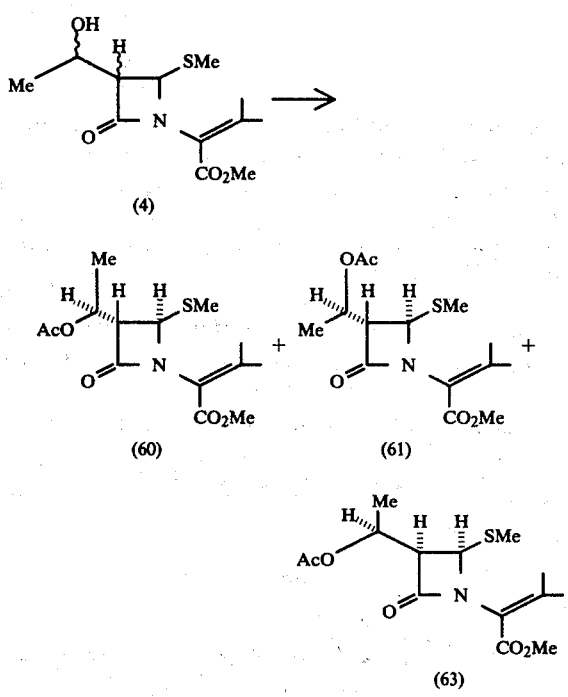

A solution of acetic anhydride (292 mg) in dry methylene chloride (2 ml) was added dropwise over 3 minutes to a stirred, ice-bath cooled, mixture of the hydroxyethylazetidinones (4) (650 mg), triethylamine (288 mg) and 4-dimethylaminopyridine (26 mg) in dry methylene chloride (10 ml). After 45 minutes at ice-bath temperature the mixture was evaporated to low volume, diluted with ethyl acetate, and washed with dilute hydrochloric acid, brine, sodium bicarbonate solution, and brine. The dried (MgSO$_4$) organic layer was evaporated and chromatographed to give two fractions. The less polar fraction, the (3RS,4SR)-3-[1-(RS)-acetoxyethyl]azetidinone (60), contaminated with approximately 25% of the (3RS,4SR)-3-[1-(SR)-acetoxyethyl]azetidinone (61), was obtained as a gum (204 mg), $\nu_{max}$ (CHCl$_3$) 1760, 1730 sh. cm$^{-1}$; δ ppm (CDCl$_3$) 1.41 and 1.43 (3H, each d, J 7 Hz), 1.98–2.23 (12H, m), 3.18–3.37 (1H, m), 3.76 (3H, s), 4.91 (0.75H, d, J 2 Hz), 4.99 (0.25H, d, J 2 Hz), 5.15–5.50 (1H, m).

The more polar fraction, the (3RS,4RS)-3-[1-(SR)-acetoxyethyl]azetidinone (63) (502 mg) was obtained as a waxy solid, m.p. 73°–5° C. (cubes ex ethyl acetate/petroleum ether), $\nu_{max}$ (CHCl$_3$) 1760, 1750 sh, 1730 sh. cm$^{-1}$; δ ppm (CDCl$_3$) 1.47 (3H, d, J 6.5 Hz), 1.99, 2.03 and 2.24 (12H, each s), 3.63 (1H, dd, J 5 and 9 Hz), 3.76 (3H, s), 5.07 (1H, d, J 5 Hz), 5.29 (1H, dq, J 6.5 and 9 Hz). (Found: C, 53.5; H 6.7; N, 4.4; S, 10.5; M+, 315.1149. C$_{14}$H$_{21}$NO$_5$S requires C, 53.3; H, 6.7; N, 4.4; S, 10.2%; M, 315.1137).

PREPARATION 7(b)

(3RS,4RS)-3-[1-(SR)-Acetoxyethyl]-4-methylsulphonylazetidin-2-one

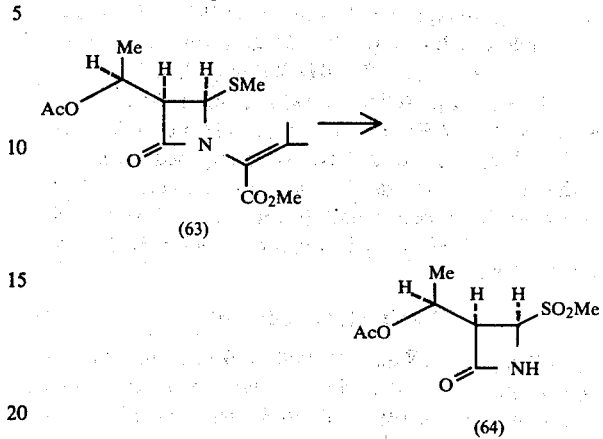

A solution of m-chloroperbenzoic acid (307 mg) in ethyl acetate (5 ml) was added dropwise over 3 minutes to a stirred, ice-bath cooled, solution of the (3RS,4RS) azetidinone (63) (255 mg) in ethyl acetate (10 ml). The mixture was allowed to attain room temperature during 45 minutes and was washed with saturated sodium bicarbonate solution (2×5 ml) and brine (3×5 ml). The dried (MgSO$_4$) organic layer was diluted with ethyl acetate (25 ml), cooled to −20° C., and ozonised oxygen passed until the starting material had been consumed (t.l.c.). The excess ozone was removed by passage of argon and the mixture was treated with methanol (20 ml). After stirring at room temperature for 20 hours the mixture was evaporated and the residue triturated with ether to give the sulphone (64) (137 mg) as a solid, m.p. 139°–141° C. (plates ex chloroform/ether); $\nu_{max}$ (CHCl$_3$) 3400, 3340, 1790, 1735, cm$^{-1}$; δ ppm [CDCl$_3$+(CD$_3$)$_2$CO] 1.44 (3H, d, J 6 Hz), 2.01 (3H, s), 2.97 (3H, s), 3.86 (1H, dd, J 5 and 10 Hz with further slight coupling to the NH proton as revealed by a decoupling experiment), 4.83 (1H, d, J 5 Hz), 5.65 (1H, dq, J 6 and 10 Hz), 7.99 (1H, broad signal). (Found: C, 41.2; H, 5.6; N, 5.9; S, 13.7. C$_8$H$_{13}$NO$_5$S requires C, 40.9; H, 5.5; N, 6.0; S, 13.6%).

PREPARATION 7(c)

(3RS,4SR)-3-[1-(SR)-Acetoxyethyl]-4-ethylthiothiocarbonylthioazetidin-2-one

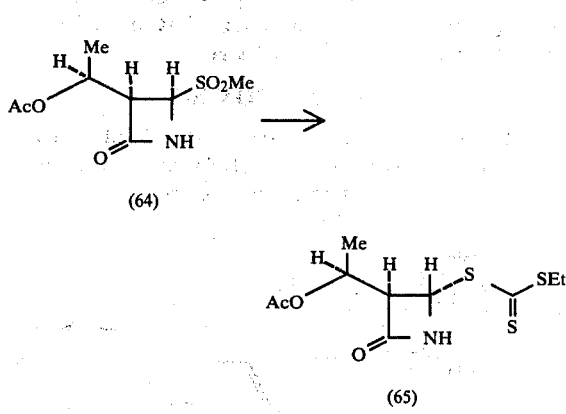

Potassium ethyltrithiocarbonate (82 mg) was added to a stirred, ice-bath cooled, mixture of the sulphone

(64) (100 mg), methylene chloride (8 ml) and water (2 ml). After 10 minutes the stirred mixture was allowed to attain room temperature during 30 minutes. The mixture was worked up as for preparation 1(f) to give, after chromatography, the trithiocarbonate (65) (100 mg) as a as a yellow solid, m.p. 101°–5° C. (ethyl acetate/petroleum ether); $\lambda_{max}$. (EtOH) 300 ($\epsilon_m$ 13,700) and 236 nm (3,700); $\nu_{max}$. (CHCl$_3$) 3420, 1780, 1740 cm$^{-1}$; δ ppm 1.36 (t, J 7 Hz) and 1.37 (d, J 6 Hz) together 6H, 2.03 (3H, s), 3.35 (q, J 7 Hz) superimposed on m, together 3H, 5.30 (1H, dq, J 6 and 6 Hz), 5.58 (1H, d, J 2.5 Hz), 6.80 (1H, broad signal). (Found: C, 41.3; H, 5.2; N, 4.7; S, 33.2. C$_{10}$H$_{15}$NO$_3$S$_3$ requires C, 41.0; H, 5.1; N, 4.8; S, 32.8%).

PREPARATION 7(d)

(3RS,4SR)-3-[1-(SR)-Acetoxyethyl]-4-ethylthiothiocarbonylthio-1-(1-hydroxy-1-p-nitrobenzyloxycarbonylmethyl)azetidin-2-one

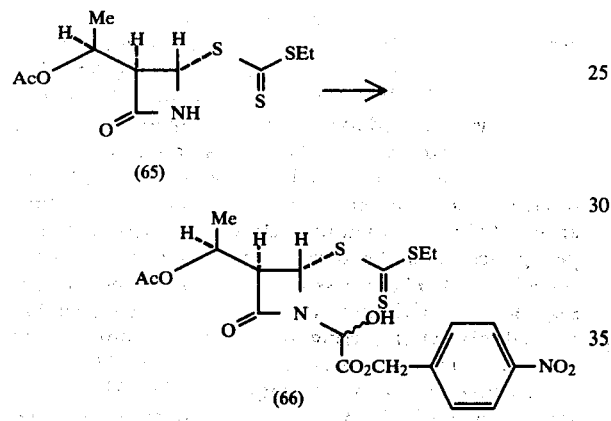

The trithiocarbonate (65) (100 mg) and p-nitrobenzyl glyoxylate monohydrate (116 mg) were heated in refluxing benzene (5 ml) under argon for 26 hours with provision for removal of water. The mixture was evaporated and chromatographed to give the hydroxyester (66) (112 mg), a 1:1 mixture of stereoisomers, as a gum, $\nu_{max}$. (CHCl$_3$) 3600–3000, 1780, 1750 cm$^{-1}$; δ ppm (CDCl$_3$) 1.25–1.45 (6H, m), 2.00 (3H, s), 3.22–3.60 (3H, m, plus q, 7 Hz), 3.90 (½H, d, J 8 Hz, exch. D$_2$O), 4.04 (½H, d, J 9 Hz, exch. D$_2$O), 5.25–5.45 (3½H, m), 5.56 (½H, d, J 9 Hz, collapses to s on exch. D$_2$O), 6.08 (½H, d, J 2½ Hz), 6.11 (½H, d, J 2½ Hz), 7.54 and 7.56 (2H, each d, J 8 Hz), 8.24 (2H, d, J 8 Hz).

PREPARATION 7(e)

(3RS,4SR)-3-[1-(SR)-Acetoxyethyl]-1-(1-chloro-1-p-nitrobenzyloxycarbonylmethyl)-4-ethylthiothiocarbonylthioazetidin-2-one

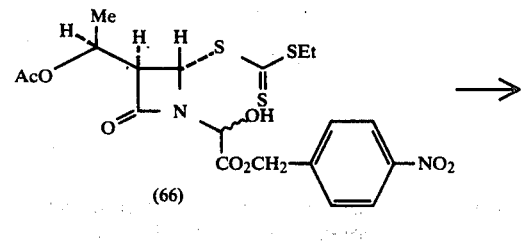

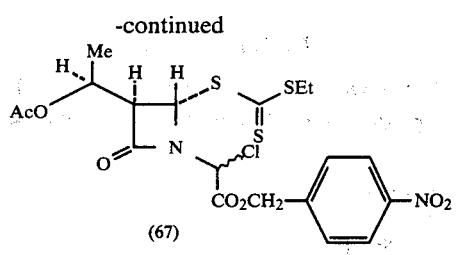

A solution of thionyl chloride (39 mg) in dry tetrahydrofuran (0.5 ml) was added dropwise to a stirred mixture of the hydroxyester (66) (110 mg) and 2,6-lutidine (35 mg) in dry tetrahydrofuran (5 ml) at −10° C. The mixture was stirred at −10° C. for 10 minutes, filtered, and evaporated. The residue was re-evaporated from dry toluene (2×3 ml) to give the chloroester (67) (114 mg) as a gum, $\nu_{max}$. (CHCl$_3$) 1790, 1745 cm$^{-1}$.

PREPARATION 7(f)

(3RS,4SR)-3-[1-(SR)-Acetoxyethyl]-4-ethylthiothiocarbonylthio-1-(1-p-nitrobeznyloxycarbonyl-1-triphenylphosphoranylidenemethyl)azetidin-2-one

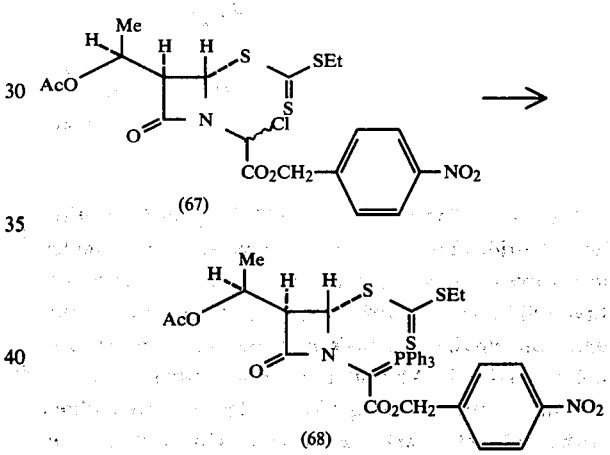

A mixture containing the chloroester (67) (114 mg), triphenylphosphine (115 mg) and 2,6-lutidine (28 mg) in dry dioxan (5 ml) was stirred at 60° C. under dry argon for 26 hours. The mixture was worked up for preparation 1(i) to give, after chromatography, the phosphorane (68) (77 mg) as an amorphous solid, $\nu_{max}$. (CHCl$_3$) 1760, 1620, 1605 shoulder cm$^{-1}$.

PREPARATION 7(g)

(5RS,6SR,8RS) and (5RS,6RS,8SR)-p-Nitrobenzyl-6-(1-Acetoxyethyl)-2-ethylthiopenem-3-carboxylate

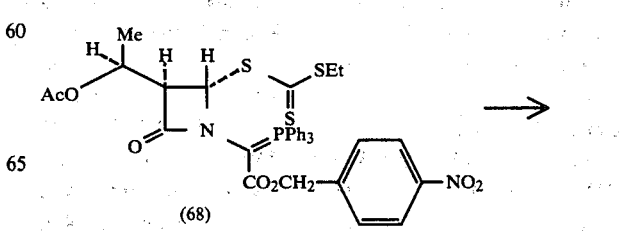

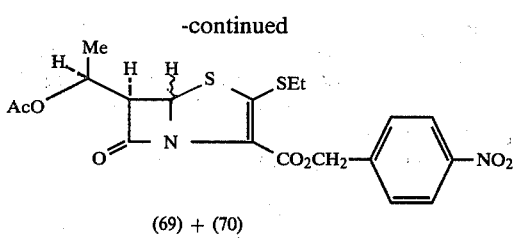

(69) + (70)

A solution of the phosphorane (68) (1.0 g) in xylene (1000 ml) was refluxed under argon for 10 hours. The mixture was evaporated and chromatographed to give two products. The less polar product, the (5RS,6RS,8SR) penem ester (69) (120 mg) was obtained as a solid, m.p. 131°–133° C. (needles ex ethylacetate/petroleum ether), $\lambda_{max}$. (EtOH) 260 ($\epsilon_m$ 16,200) and 334 n.m. (11,000); $\nu_{max}$. (CHCl$_3$) 1795, 1730 and 1695 cm$^{-1}$; $\delta$ ppm (CDCl$_3$) 1.37 (3H, t, J 7.7 Hz) 1.54 (3H, d, J 6.3 Hz), 2.04 (3H, s), 2.76–3.26 (2H, m), 4.00 (1H, dd, J 4.0 and 9.9 Hz), 5.18 and 5.48 (ABq, J 14 Hz) overlaying a m, together 3H, 5.73 (1H, d, J 4.0 Hz), 7.60 (2H, d, J 8 Hz), 8.21 (2H, d, J 8 Hz). (Found: C, 50.5; H, 4.2; N, 6.1; S, 13.8; M+, 452.0729. C$_{19}$H$_{20}$N$_2$O$_7$S$_2$ requires C, 50.5; H, 4.4; N, 6.2; S, 14.2%; M, 452.0712). The more polar product, the (5RS,6SR,8RS) penem ester (70) (221 mg), was obtained as a solid, m.p. 131°–132° C. (needles ex ethyl acetate/petroleum ether), $\lambda_{max}$. (EtOH) 261 ($\epsilon_m$ 16,500) and 339 n.m. (11,000); $\nu_{max}$. (CHCl$_3$) 1795, 1740, and 1695 cm$^{-1}$; $\delta$ ppm (CDCl$_3$) 1.29–1.46 (6H, m), 2.05 (3H, s), 2.70–3.16 (2H, m), 3.84 (1H, dd, J 1.6 and 7.7 Hz), 5.21 and 5.47 (ABq, J 14 Hz) overlaying a m, together 3H, 5.62 (1H, d, J 1.6 Hz), 7.62 (2H, d, J 8 Hz), 8.21 (2H, d, J 8 Hz). (Found: C, 50.4; H, 4.2; N, 6.1; S, 13.9; M+, 452.0707. C$_{19}$H$_{20}$N$_2$O$_7$S$_2$ requires C, 50.5; H, 4.4; N, 6.2; S, 14.2%; M, 452.0712).

EXAMPLE 7

(5RS)-p-Nitrobenzyl 6-Ethylidene-2-ethylthiopenem-3-carboxylate

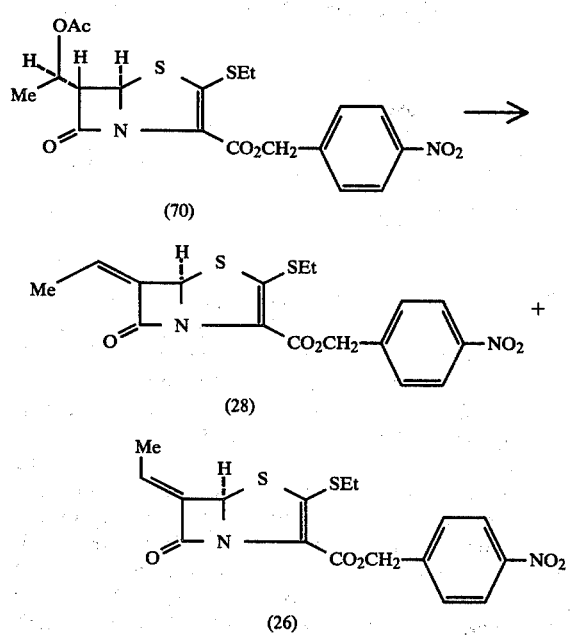

An ice-bath cooled solution of the penem ester (70) (45 mg) in dry methylene chloride (1 ml) was treated with 1,8-diazabicyclo[5.4.0]undec-7-ene (DBU) (0.1 ml of a solution containing 166 mg DBU/ml methylene chloride). After stirring at ice-bath temperature for 15 minutes the mixture was diluted with ethyl acetate (10 ml) and washed with 5% citric acid (2 ml), brine (2 ml), saturated sodium bicarbonate solution (2 ml) and brine (3×2 ml). The dried (MgSO$_4$) organic layer was evaporated and the residue chromatographed on silica gel eluting with methylene chloride to give the E-ethylidenepenem ester (28) (7 mg) and the Z-ethylidenepenem ester (26) (14 mg).

PREPARATION 8(a)

Silver (3RS,4SR)-3-[1-(SR)-Acetoxyethyl]-1-(1-p-nitrobenzyloxycarbonyl-1-triphenylphosphoranylidenemethyl)azetidin-2-one-4-thiolate (72)

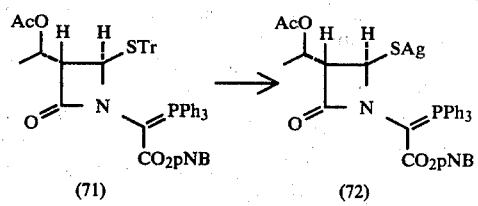

A solution of the phosphorane (71) (GB No. 2 042 515 A) (230 mg, 0.26 mmol) was dissolved in dry dichloromethane (3 ml) and diluted with hot (50°) methanol (8 ml). The mixture was sequentially treated with pyridine (25 μl, 0.31 mmol) and a hot (50°) 0.15M methanolic solution of silver nitrate (2.08 ml, 0.31 mmol). The mixture was then stirred at room temperature for one hour and a further hour at 0°. The reaction mixture was concentrated, then filtered and the solid washed with ice-cold methanol and ether, then dried to give the silver thiolate (72) (100 mg, 51%) as a light brown solid, $\nu_{max}$. (Nujol) 1760, 1745 cm$^{-1}$.

PREPARATION 8(b)

(3RS,4SR)-3-[1-(SR)-Acetoxyethyl]-4-acetylthio-1-(1-p-nitrobenzyloxycarbonyl-1-triphenylphosphoranylidenemethyl)azetidin-2-one (73)

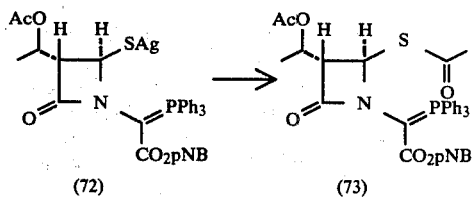

A solution of the silver thiolate (72) (100 mg, 0.13 mmol) in dry dichloromethane (6 ml) under argon at 0° was sequentially treated with pyridine (40 μl, 0.49 mmol) and acetyl chloride (30 μl, 0.42 mmol). The mixture was stirred at 0° for 30 minutes and the solid was filtered and washed with dichloromethane. The organic solution was washed with dilute hydrochloric acid solution, dilute sodium bicarbonate solution and brine. The dried organic phase was evaporated and the residue was chromatographed on silica eluting with ethyl acetate/petroleum ether mixtures to give the thioester (73) (50 mg, 55%) as a light yellow amorphous solid, $\nu_{max}$. (CH$_2$Cl$_2$) 1760, 1740 (sh), 1690, 1620 cm$^{-1}$.

PREPARATION 8(c)

(5RS,6SR,8RS)-p-Nitrobenzyl-6-(1-Acetoxyethyl)-2-methylpenem-3-carboxylate (74)

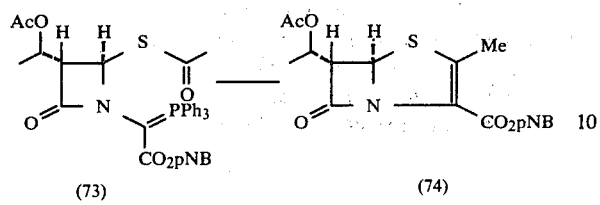

A solution of the thioester (73) (50 mg, 0.073 mmol) in toluene (50 mol) was heated at reflux under argon for 6 hours. The reaction mixture was evaporated and chromatographed on silica eluting with ethyl acetate/petroleum ether mixtures to give the penem (74) as a white solid after trituration with ether (24 mg, 81%), m.p. 115°–6° (needles ex ethyl acetate/petroleum ether), $\lambda_{max}$. (EtOH) 311 n.m. ($\epsilon_m$ 9,325), 264 (12,700) $\nu_{max}$. (CHCl$_3$) 1790, 1760, 1710, 1590 cm$^{-1}$, $\delta$ (CDCl$_3$) 1.39 (3H, d, J 7 Hz), 2.04 (3H, s), 2.35 (3H, s), 3.81 (1H, dd, J 2, 8 Hz), 5.20 and 5.45 (ABq, J 14 Hz) overlaying 5.26 (dd, J 7, 8 Hz) (together 3 Hz, 5.53 (1H, d, J 2 Hz), 7.60 (2H, d, J 8 Hz), 8.22 (2H, d, J 8 Hz); Found: M+406.0844. C$_{18}$H$_{18}$N$_2$O$_7$S requires M, 406.0833).

EXAMPLE 8(a)

(5RS)-p-Nitrobenzyl-6-Ethylidene-2-methylpenem-3-carboxylate (75)

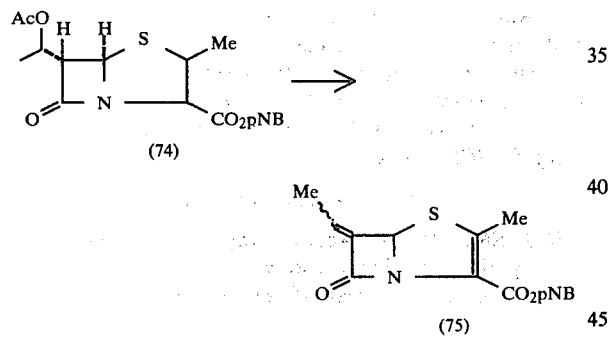

A solution of the acetate (74) (22 mg, 0.054 mmol) in dry dichloromethane (2 ml) at −20° under argon was treated with a solution of 1,8-diazabicyclo-[5.4.0]undec-7-ene (DBU) (10.1 mg, 0.067 mmol) in dichloromethane (0.1 ml). After 45 minutes the reaction mixture was treated with more DBU (0.24 equivalents). After a further 30 minutes at −20° the reaction mixture was poured into dichloromethane, washed with 5% citric acid solution, brine, dilute sodium bicarbonate solution and brine, then dried and evaporated. The residue was dissolved in 25% dichloromethane/petroleum ether and chromatographed on silica eluting with dichloromethane/petroleum ether mixtures to give a separable mixture of E and Z ethylidenepenems (75). The less polar, E isomer (2 mg, 11%), was obtained as a gum, $\nu_{max}$. (CH$_2$Cl$_2$) 1780, 1715, 1590 cm$^{-1}$; $\delta$ (CDCl$_3$) 2.15 (3H, d, J 7.5 Hz), 2.39 (3H, s), 5.23 and 5.48 (2H, ABq, J 13.5 Hz), 6.00 (1H, q, J 7.5 Hz), 6.09 (1H, s), 7.65 (2H, d, J 9 Hz), 8.25 (2H, d, J 9 Hz).

The more polar, Z isomer (15 mg, 80%), was obtained as light yellow needles, m.p. 139°–140° (ex ethyl acetate/petroleum ether), $\lambda_{max}$. (EtOH) 267 n.m. ($\epsilon_m$ 10,015), approx. 280 (inflection) $\nu_{max}$. (CH$_2$Cl$_2$) 1780, 1715, 1590, cm$^{-1}$; $\delta$ (CDCl$_3$) 1.85 (3H, d, J 7.5 Hz), 2.40 (3H, s), 5.25 and 5.48 (2H, ABq, J 15 Hz), 6.12 (1H, s, $\omega_{\frac{1}{2}}$ 3 Hz), 6.45 (1H, q with further fine coupling, J 7.5 Hz), 7.66 (2H, d, J 9 Hz), 8.24 (2H, d, J 9 Hz). (Found: M+ 346.0612. C$_{16}$H$_{14}$N$_2$O$_5$S requires M, 346.0602).

EXAMPLE 8(b)

(5RS)-Sodium (Z)-Ethylidene-2-methylpenem-3-carboxylate

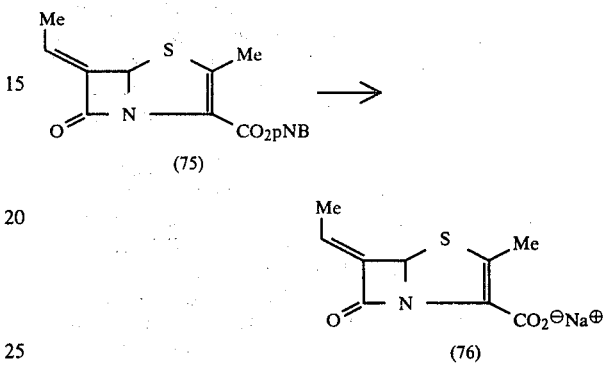

A solution of the (Z)-ethylidenepenem ester (75) (15 mg) in dioxane (2.5 ml) and water (0.5 ml) was hydrogenated over 5% palladium/charcoal catalyst (23 mg) at S.T.P. for 45 minutes. A further amount of catalyst (15 mg) was added and the hydrogenation continued for 30 minutes. A 1% sodium bicarbonate solution (0.36 m!) was added and the mixture worked up as for Example 1(b) to give the sodium salt (76) (2 mg) as an amorphous solid, $\nu_{max}$. (H$_2$O) 291, 257 n.m., $\delta$(D$_2$O) 1.82 (3H, d, J 7.5 Hz), 2.32 (3H, s), 6.25 (1H, s), 6.57 (1H, q, J 7.5 Hz).

PREPARATION 9(a)

(3ξ,4RS)-3-Bromo-3-hydroxymethyl-1-(1-methoxycarbonyl-2-methylprop-1-enyl)-4-methylthioazetidin-2-one

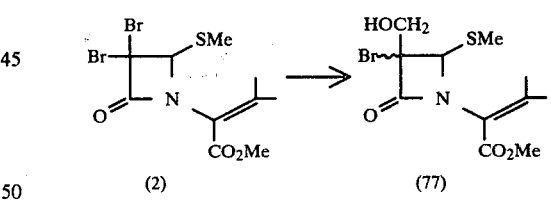

A solution of methyl magnesium bromide (2M in diethyl ether, 0.7 ml) was added dropwise to a stirred solution of the dibromosecopenicillanate (2) (0.5 g) in dry tetrahydrofuran (10 ml) at −76° C. After stirring at −76° C. for 10 minutes a stream of argon was passed, first over dry paraformaldehyde (0.5 g) heated at 150° C. and then over the surface of the vigorously stirred reaction mixture. [During a 10 minutes reaction time approximately 0.2 g of formaldehyde was generated]. The argon/formaldehyde stream was then interrupted, stirring was maintained for 5 minutes, then a saturated aqueous solution of ammonium chloride (1 ml) was added and the stirred mixture was allowed to reach room temperature. The mixture was then diluted with ethyl acetate, washed with water and brine, dried (MgSO$_4$) and evaporated to give a crude gum. Chromatography of the crude product on silica gel eluting with ethyl acetate/petroleum ether mixtures gave the bromohydrin (77) (0.23 g, 53%) as a clear gum, $\nu_{max}$ (CHCl$_3$) 3570, 3350 (b), 1765, 1720, 1625 (w) cm$^{-1}$. δ(CDCl$_3$) 2.03 (3H, s), 2.14 (3H, s), 2.26 (3H, s) 2.86 (1H, t, J 7 Hz exch. D$_2$O) 3.78 (s) 4.1 (m, collapses to ABq, centres 3.92 and 4.17, J 12 Hz with D$_2$O) two signals together 4H, 5.39 (1H, s).

PREPARATION 9(b)

(3RS,4RS) and (3RS,4SR)-3-Hydroxymethyl-1-(1-methoxycarbonyl-2-methylprop-1-enyl)-4-methylthioazetidin-2-one

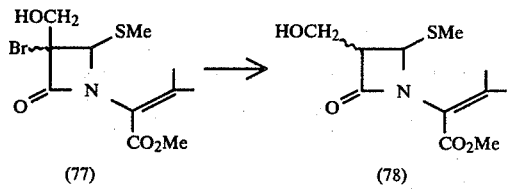

The bromohydrin (77) (100 mg) in tetrahydrofuran (1 ml) cooled in ice/salt mixture was stirred with zinc dust (200 mg) and N/1 aqueous ammonium acetate solution (0.2 ml). After 10 minutes in the cold and 10 minutes at room temperature the reaction mixture was filtered, diluted with ethyl acetate and washed with N/10 aqueous hydrochloric acid then brine. The solution was dried (MgSO$_4$) and evaporated to an oil. Chromatography on silica gel eluting with ethyl acetate/petroleum ether mixture gave an 85:15 mixture of the cis and trans-hydroxymethylazetidinones (78) (54 mg, 70%) $\nu_{max}$. (CHCl$_3$) 3450 (b), 1760, 1725, 1630 cm$^{-1}$. δ(CDCl$_3$) 2.0 (3H, s) 2.14 (3H, s) 2.24 (3H, s) 2.4–2.8 (1H, m, exch. D$_2$O) 3.2–3.7 (1H, m), 3.75 (3H, s), 3.9–4.1 (2H, m), 5.03 (d, J 3 Hz) 5.10 (d, J 5 Hz) together 1H.

PREPARATION 9(c)

3-t-Butyldiphenylsilyloxymethyl-1-(1-methoxycarbonyl-2-methylprop-1-enyl-4-methylthioazetidinone

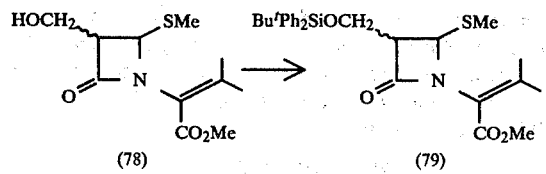

The mixture of cis and trans-hydroxymethylazetidinones (78) (0.650 g) in dry dimethylformamide (20 ml) was treated with t-butyldiphenylsilyl chloride (1.25 g) and imidazole (0.34 g) at room temperature for 2½ hours. Most of the solvent was evaporated off in vacuo and the residue was partitioned between ethyl acetate and water. The solvent layer was then separated, dried (MgSO$_4$) and evaporated. The residue was chromatographed on silica gel eluting with ethylacetate/petroleum ether mixtures. First to be eluted was the fraction containing the trans isomer (240 mg), then a mixed cis/trans fraction (45 mg) and finally the cis isomer (825 mg). The less polar fraction, the (3RS,4SR)-3-t-butyldiphenylsilyloxymethylazetidin-2-one was obtained as a gum, $\nu_{max}$. (CHCl$_3$) 1755, 1725, 1630 cm$^{-1}$. δ(CDCl$_3$) 1.12 (9H, s) 2.05 (3H, s) 2.15 (3H, s), 2.30 (3H, s) 3.2–3.55 (1H, m) 3.77 (3H, s) 4.08 (2H, b.d., J 4 Hz) 5.25 (1H, d, J 3 Hz) 7.35–8.0 (10H, m). The more polar fraction, the (3RS,4RS)-3-t-butyldiphenylsilyloxymethylazetidin-2-one was obtained as a gum, $\nu_{max}$ (CHCl$_3$) 1755, 1725, 1630 cm$^{-1}$; δ(CDCl$_3$) 1.10 (9H, s) 2.08 (3H, s) 2.17 (3H, s) 2.28 (3H, s) 3.79 (3H, s) 4.0–4.45 (3H, m) 5.23 (1H, d, J 6 Hz) 7.2–8.1 (10H, m).

PREPARATION 9(d)

(3RS,4RS) and (3RS,4SR)-3-t-Butyldiphenylsilyloxymethyl-4-methylsulphonylazetidin-2-one

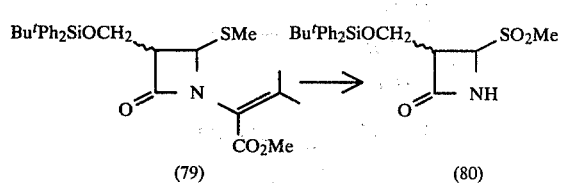

A solution of m-chloroperbenzoic acid (0.85 g) in ethyl acetate (10 ml) was added dropwise over ten minutes to a stirred, ice-cooled solution of the azetidinone (79) (cis/trans mixture) in ethyl acetate (30 ml). After 10 minutes the temperature was raised to room temperature for half an hour. The reaction mixture was washed with saturated aqueous sodium bicarbonate, water and brine. The dried (MgSO$_4$) organic layer was evaporated. The white amorphous residue was redissolved in methylene dichloride, cooled to $-20°$ C., and ozonized oxygen was passed for 45 minutes. Methanol (50 ml) and 2,6-lutidine (10 drops) were then added and the mixture was kept at room temperature for 1 hour then evaporated to give a gum. This was redissolved in ethyl acetate, washed with 5% aqueous citric acid, then brine, dried (MgSO$_4$) and evaporated. The residual gum was chromatographed on silica gel eluting with ethyl acetate/petroleum ether mixtures to give the sulphone (80) as a gummy mixture of cis/trans isomers (500 mg), $\nu_{max}$. (CHCl$_3$) 3400, 1790, 1320, 1150 cm$^{-1}$. δ(CDCl$_3$) 1.1 (9H, s) 3.1 (3H, s) 3.65–4.65 (m, CH$_2$OSi, C-3-H and C-4-H trans) 4.78 (d, J 4 Hz, C-4-H cis) together 4H, 7.2–7.9 (11H, one H exch. D$_2$O).

PREPARATION 9(e)

(3RS,4SR)-3-(t-Butyldiphenylsilyloxymethyl)-4-ethylthiothiocarbonylthioazetidin-2-one

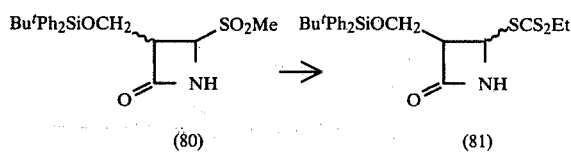

A mixture of the sulphone (80) (cis/trans mixture, 1.8 g) in methylene chloride (50 ml) and potassium ethyl trithiocarbonate (1.52 g) in water (50 ml) was stirred vigorously at room temperature. After 6 hours the solvent layer was separated, washed with water, dried (MgSO$_4$) and evaporated. The residue was a yellow crystalline mass which was washed with a little toluene/petroleum ether mixture (1.22 g). Recrystallisation from ethyl acetate/petroleum ether gave the pure trans azetidinone (81) as yellow needles, m.p. 142°, $\nu_{max}$. (CHCl$_3$) 3420, 1780 cm$^{-1}$, δ(CDCl$_3$) 1.06 (9H, s), 1.38 (3H, t, J 8 Hz) 3.40 (q, J 8 Hz) overlaying (m), together 3H, 3.95–4.15 (2H, m), 5.76 (1H, d, J 2 Hz) 6.78 (1H, b.s.) 7.25–7.9 (10H, m). (Found: C, 57.8; H, 6.0; N, 2.9;

S, 20.3. $C_{23}H_{29}NO_2S_3Si$ requires C, 58.1; H, 6.1; N, 3.0; S, 20.2%).

PREPARATION 9(f)

(RS,4SR)-3-t-Butyldiphenylsilyloxymethyl-4-ethylthiocarbonylthio-1-(1-hydroxy-1-p-nitrobenzyloxycarbonylmethyl)azetidin-2-one

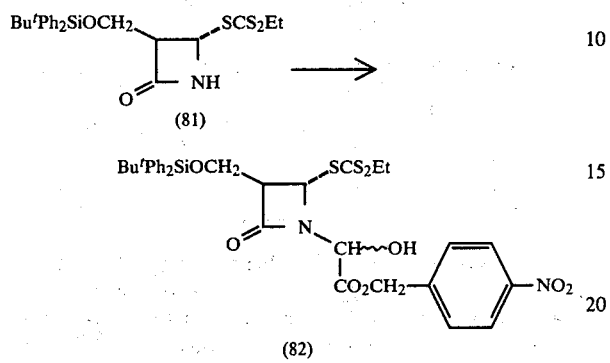

The trithiocarbonate (81) (310 mg) and p-nitrobenzyl glyoxylate monohydrate (300 mg) were refluxed in benzene (20 ml) under argon for 24 hours with provision for removal of water. The mixture was evaporated and the residual gum chromatographed on silica gel eluting with ethyl acetate/petroleum ether mixtures to give the hydroxy-ester (82) as a mixture of diastereoisomers (420 mg), a yellow amorphous solid. $\nu_{max}$. (CHCl$_3$) 3500, 1780, 1760 cm$^{-1}$. $\delta$(CDCl$_3$) 1.06 (9H, s) 1.45 (3H, t, J 8 Hz) 3.40 (q, J 8 Hz) 3.52 (b.d. J 2 Hz) together 3H, 4.1 (2H, b.s.) 4.34 and 4.4 (1H, 2 d, J 8 Hz, exch. D$_2$O) 5.35 (s) 5.47 and 5.73 (2 d, J 8 Hz) together 3H, 6.3 and 6.44 (1H, 2 d, J 2 Hz) 7.3–8.5 (14H, m).

PREPARATION 9(g)

(3RS,4SR)-3-t-Butyldiphenylsilyloxymethyl-4-ethylthiothiocarbonylthio-1-(1-p-nitrobenzyloxycarbonyl-1-triphenylphosphoranylidenemethyl)azetidin-2-one

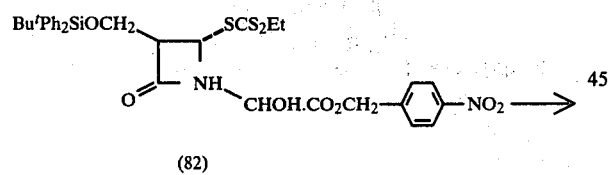

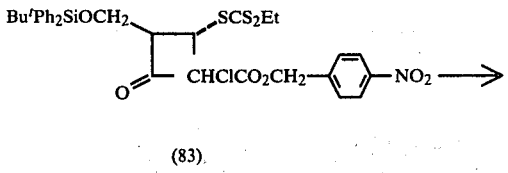

The hydroxy-ester (82) (420 mg) in tetrahydrofuran (20 ml) at −20° C. was treated with 2,6-lutidine (99 mg) and thionyl chloride (0.07 ml) and allowed to reach room temperature over 0.5 hours. The solution was then filtered and evaporated under high vacuum to give the crude chloro-ester (83). This was redissolved in dioxan (20 ml) then 2,6-lutidine (29 mg) and triphenylphosphine (320 mg) were added. The stirred mixture was kept at 60° C. under argon for 7 days and was then evaporated to dryness in vacuo. The residue was dissolved in ethyl acetate and washed successively with 1% aqueous citric acid solution, sodium bicarbonate solution and brine. The dried (MgSO$_4$) organic layer was evaporated the residue chromatographed on silica gel eluting with ethyl acetate/petroleum ether mixtures to give the phosphorane (84) as an amorphous yellow solid (370 mg) $\nu_{max}$. (CHCl$_3$) 1750, 1615, 1605 cm$^{-1}$.

PREPARATION 9(h)

(3RS,4SR)-3-Hydroxymethyl-4-ethylthiothiocarbonylthio-1-(1-p-nitrobenzyloxycarbonyl)-1-triphenylphosphoranylidenemethyl)azetidin-2-one

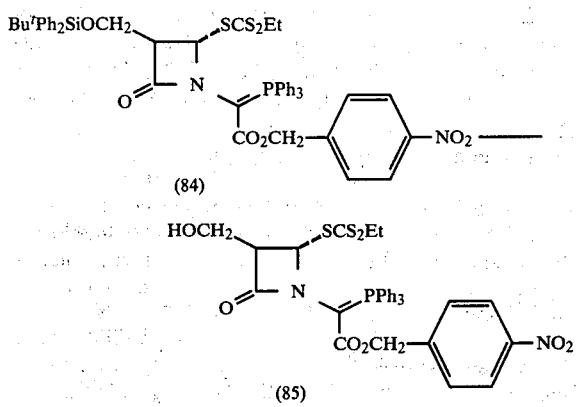

A solution of the phosphorane (84) (1.75 g) in 15% methanolic hydrogen chloride (30 ml) was kept for 1 hour at room temperature. It was then neutralised with aqueous sodium hydrogen carbonate and extracted with ethyl acetate. The solvent layer was dried (MgSO$_4$) and evaporated then the residue was chromatographed on silica gel eluting with ethyl acetate—petroleum ether mixtures. The pure product (85) was isolated as a yellow amorphous solid (1.09 g), $\nu_{max}$. (CHCl$_3$) 3400 (b), 1760, 1620, 1610 cm$^{-1}$.

PREPARATION 9(i)

(6RS,5SR) and (6RS,4RS)-p-Nitrobenzyl 6-Hydroxymethyl-2-ethylthiopenem-3-carboxylate

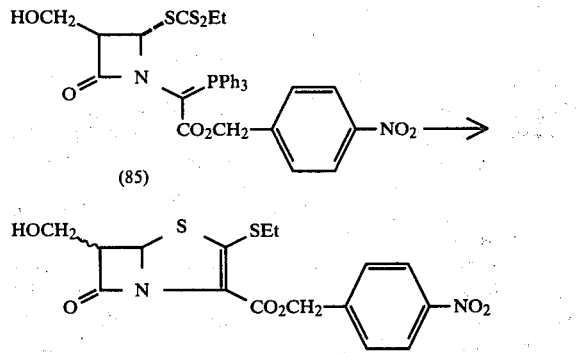

A solution of the phosphorane (85) (547 mg) was refluxed in xylene (150 ml) under argon for 10 hours. The mixture was evaporated and the residue chromatographed on silica gel eluting with ethyl acetate/petroleum ether mixtures to give the cis and trans penems (86) 260 mg trans/cis 7/3. Careful re-chromatography allowed pure samples of the trans and cis isomers to be separated. The more polar trans isomer was a cream crystalline solid, m.p. 162°–163° (from ethyl acetate/petroleum ether) $\nu_{max}$. (EtOH) 338 n.m. ($\epsilon_m$ 10,025) 261 (13,050) $\nu_{max}$. 3600, 3400 (b), 1790, 1695, 1610 cm$^{01}$. $\epsilon$(250 m.c. (CDCl$_3$) 1.35 (3H, t, J 7 Hz) 2.90–3.20 (2H, m) 3.94–4.10 (3H, m, 4.38 (1H, t, J 5 Hz, exch. D$_2$O) 5.28 and 5.53 (2H, ABq, J 14 Hz) 5.81 (1H, d, J 1.5 Hz) 7.78 (2H, d, J 7 Hz) 8.26 (2H, d, J 7 Hz). (Found: M+, 396.480. C$_{16}$H$_{16}$N$_2$O$_6$S$_2$ requires 396.0446). The less polar cis isomer was also a cream solid, m.p. 150°–155°, $\nu_{max}$. (CHCl$_3$) 3600, 3400 (b), 1790, 1690 cm$^{-1}$. $\delta$(CDCl$_3$) 1.37 (3H, t, J 7 Hz) 3.6 (2H, q, with fine coupling, J 7 Hz) 2.75 (1H, s, exch. D$_2$O) [4.03 and 4.05 (2H, q, J 7 and 9 Hz) 4.34 (1H, ddd, J 9, 7, 4 Hz) these signals described with D$_2$O exch.] 5.27 and 5.50 (2H, ABq, J 14 Hz) 5.90 (1H, d, J 4 Hz) 7.75 (2H, d, J 7 Hz) 8.24 (2H, d, J 7 Hz). (Found: M+, 396.0480, C$_{16}$H$_{16}$N$_2$O$_6$S$_2$ requires 396.0446).

EXAMPLE 9

5(RS)-p-Nitrobenzyl 6-Methylene-2-ethylthiopenem-3-carboxylate

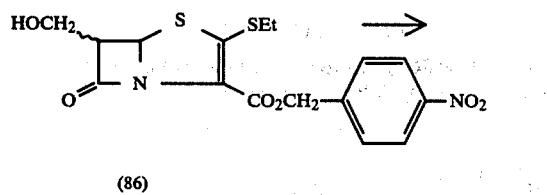

(86)

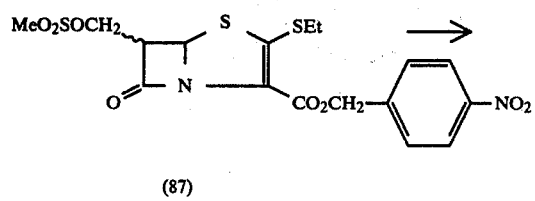

(87)

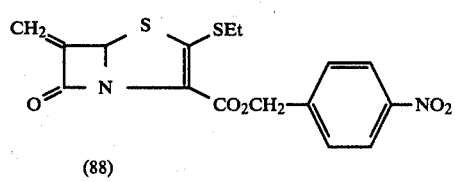

(88)

The hydroxymethylpenem (86) (102 mg) in methylene chloride (15 ml) at 0° C. was treated with triethylamine (33 mg) followed by methanesulphonyl chloride (33 mg). The mixture was then kept at room temperature for 0.5 hours, evaporated to dryness and redissolved in ethyl acetate. The solution was washed with brine, dried (MgSO$_4$) and again evaporated to give the crude methane sulphonate (87). This was dissolved in methylene chloride (10 ml) cooled to 0° C. and treated with DBU (43 mg). The mixture was then kept at room temperature for 0.5 hours. This was then evaporated and chromatographed on silica gel eluting with ethyl acetate/petroleum ether mixtures to give the methylene penem (88) (47 mg) as a yellow crystalline solid, m.p. 146°–147° C. (from ethyl acetate), $\lambda_{max}$. (EtOH) 267 n.m. ($\epsilon_m$ 18,500) 302 n.m. (infl.) (11,500) 343 n.m. (infl.) (5,400), $\delta$(CDCl$_3$) 1.38 (3H, t, J 7 Hz) 2.96 and 2.98 (2H, 2 d, J 7 Hz) 5.20 and 5.48 (2H, ABq, J 14 Hz) 5.48 (1H, dd, J 2.4 and 0.7 Hz) 5.98 (1H, dd, J 2.4 and 1.3 Hz) 6.19 (1H, dd J 1.3 and 0.7 Hz) 7.63 and 8.20 (4H, 2 d, J 8 Hz). (Found: M+ 378.0333. C$_{16}$H$_{14}$N$_2$O$_5$S$_2$ requires M, 378.0342).

PREPARATION 10(a)

(3RS,4SR)-3-[1-(RS)-Acetoxyethyl]-4-methylsulphonylazetidin-2-one

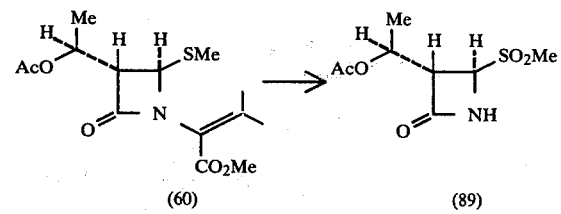

(60)             (89)

A solution of m-chloroperbenzoic acid (241 mg) in ethyl acetate (3 ml) was added dropwise over 2 minutes to a stirred, ice bath cooled, solution of the impure azetidinone (60) (200 mg) in ethyl acetate (10 ml). The stirred mixture was allowed to attain room temperature during 45 minutes and was washed with saturated sodium bicarbonate solution (2×5 ml) and brine (3×5 ml). The dried (MgSO$_4$) organic layer was diluted with ethyl acetate (15 ml) and treated with ozonised oxygen and methanol as in preparation 1(e) to give, after chromatography, the sulphone (89) (137 mg) contaminated with approximately 25% of the (3RS,4SR)-3-[1-(SR)-acetoxyethyl] isomer as a gum, $\nu_{max}$. (CHCl$_3$) 3550 br, 3410, 3300 br, 1795, 1745 cm$^{-1}$; $\delta$ppm (CDCl$_3$) 1.41 and 1.43 (3H, each d, J 6.5 Hz), 2.03 and 2.08 (3H, each s) 2.95 (3H, s), 3.68 (dd, J 2 and 7 Hz) and 3.79 (dd, J 2 and 5 Hz) together 1H, 4.53 (¾H, d, J 2 Hz), 4.73 (¼H, d, J 2 Hz), 5.14–5.45 (1H, m), 7.05 (1H, br. signal).

PREPARATION 10(b)

(3RS,4SR)-3-[1-(RS)-Acetoxyethyl]-4-ethylthiocarbonylthioazetidin-2-one

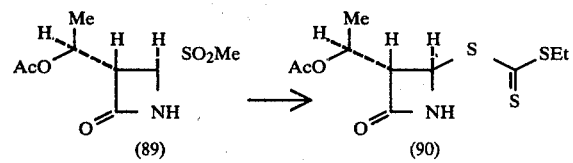

(89)             (90)

A solution of the impure sulphone (89) (110 mg) in methylene chloride (5 ml) was cooled in an ice bath and treated with a solution of potassium ethyltrithiocarbonate (91 mg) in water (1 ml). After 10 minutes at ice bath temperature the stirred mixture as allowed to attain room temperature during 30 minutes. The mixture was worked up as for preparation 1(f) to give, after chromatography, the (3RS,4SR)-3-[1-(RS)-acetoxyethyl]azetidinone (90) (97 mg) containing approximately 20% of the (3RS,4SR)-3-[1-(SR)-acetoxyethyl] isomer as impurity, $\nu_{max}$. (CHCl$_3$) 3610, 3410, 1780, 1740 cm$^{-1}$; $\delta$ppm (CDCl$_3$) 1.35 (t, J 7 Hz), 1.37 (d, J 6 Hz) and 1.41 (d, J 6.5 Hz) together 6H, 2.03 and 2.07 (3H, each s), 3.2–3.5 (3H, m), 5.17–5.5 (1H, m), (5.43, 0.8H, d, J 2 Hz), 5.58 (0.2H, d, J 2 Hz), 6.5–6.8 br (1H).

PREPARATION 10(c)

(3RS,4SR)-3-[1-(RS)-Acetoxyethyl]-4-ethylthiothiocarbonylthio-1-(1-hydroxy-1-p-nitrobenzyloxycarbonylmethyl)azetidin-2-one

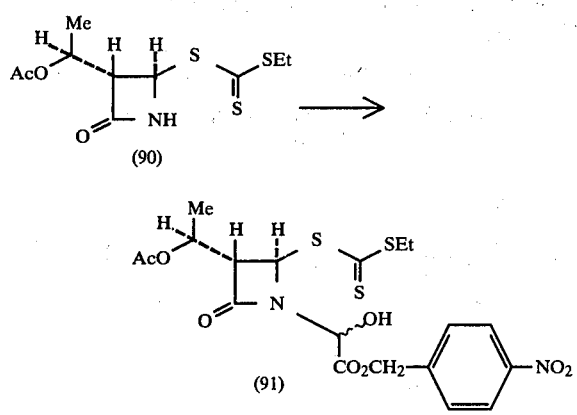

The impure azetidinone (90) (1.0 g) and p-nitrobenzyl glyoxylate monohydrate (1.55 g) were heated in refluxing benzene (40 ml) under argon with provision for removal of water for 22 hours. The mixture was evaporated and chromatographed to give the hydroxyester (91) (1.51 g), a mixture of stereoisomers, as a gum, $\nu_{max}$. (CHCl$_3$) 3600–3100, 1780, 1745 cm$^{-1}$.

PREPARATION 10(d)

(3RS,4SR)-3-[1-(RS)-Acetoxyethyl]-1-(1-chloro-1-p-nitrobenzyloxycarbonylmethyl)-4-ethylthiothiocarbonylthioazetidin-2-one

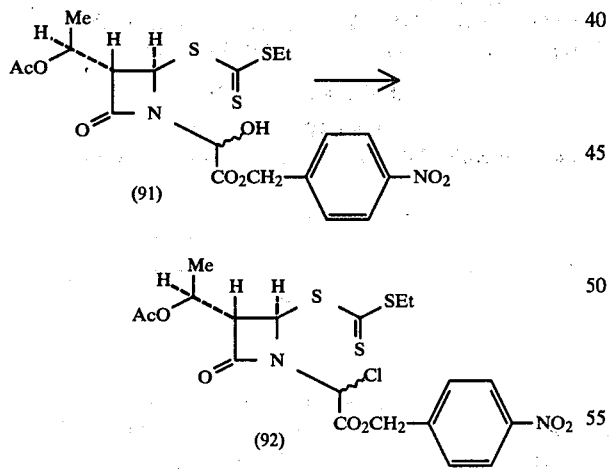

A solution of thionyl chloride (537 mg) in dry tetrahydrofuran (5 ml) was added dropwise over 10 minutes to a stirred mixture of the hydroxyester (91) (1.51g) and 2,6-lutidine (483 mg) in dry tetrahydrofuran (30 ml) at −10° C. The mixture was stirred at −10° C. for 10 minutes, filtered and evaporated. The residual gum was re-evaporated from dry toluene (2×3 ml) to give the chloroester (92) (1.57 g) as a gum, $\nu_{max}$. (CHCl$_3$) 1790 and 1745 cm$^{-1}$.

PREPARATION 10(e)

(3RS,4SR)-3-[1-(RS)-Acetoxyethyl]-4-ethylthiothiocarbonylthio-1-(1-p-nitrobenzyloxycarbonyl-1-triphenylphosphoranylidenemethyl)azetidin-2-one

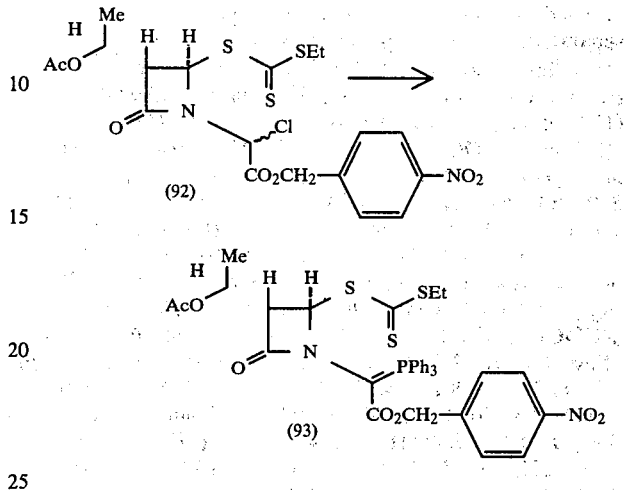

A mixture containing the chloroester (92) (1.57 g), triphenylphosphine (1.58 g) and 2,6-lutidine (387 mg) in dry dioxan (30 ml) was stirred at 60° C. under dry argon for 24 hours. The mixture was worked up as for preparation 1(i) to give the phosphorane (93) (1.12 g) as an amorphous solid, $\nu_{max}$. (CHCl$_3$) 1760, 1625 cm$^{-1}$.

PREPARATION 10(f)

(5RS,6SR,8SR) and (5RS,6RS,8RS)-p-Nitrobenzyl 6-(1-Acetoxyethyl)-2-ethylthiopenem-3-carboxylate

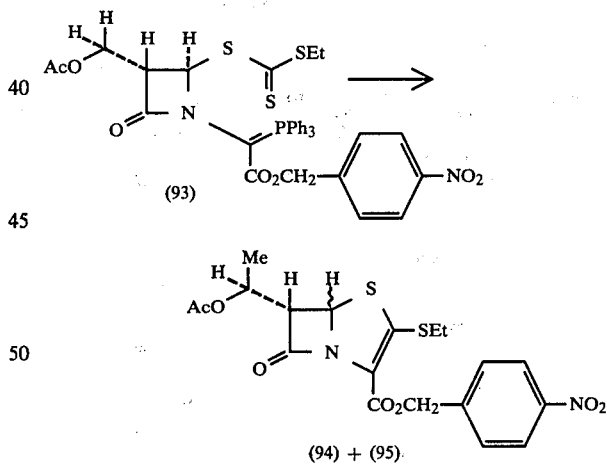

The phosphorane (93) (1.04 g) was heated in refluxing xylene (1000 ml) under dry argon for 10 hours. The mixture was evaporated and chromatographed to give two products. The less polar product, the (5RS,6SR,8SR) penem ester (94) (262 mg) was obtained as a solid, m.p. 143°–144° C. (needles ex ethyl acetate/petroleum ether); $\lambda_{max}$. (EtOH) 339 ($\epsilon_m$ 9,600) and 261 n.m. (14,400); $\nu_{max}$. (CHCl$_3$) 1785, 1740, 1695 cm$^{-1}$; $\delta$ppm (CDCl$_3$) 1.37 (3H, t, J 7.4 Hz), 1.44 (3H, d, J 6.4 Hz), 2.09 (3H, s), 2.84–3.13 (2H, m), 3.96 (1H, dd, J 1.6 and 4.0 Hz), 5.1–5.5 (3H, m), 5.54 (1H, d, J 1.6 Hz), 7.62 (2H, d, J 8.6 Hz), 8.22 (2H, d, J 8.6 Hz). (Found: C, 50.5; H, 4.4; N, 6.2; S, 14.0; M+, 452.0721. C$_{19}$H$_{20}$N$_2$O$_7$S$_2$ requires C, 50.5; H, 4.4; N, 6.2; S, 14.2%; M, 452.0712). The more polar product, the (5RS,6RS,8RS)penem ester (95) (15 mg) was also obtained as a solid, m.p. 179°-181° C. (needles ex ethyl acetate/petroleum ether); $\lambda_{max.}$ (EtOH) 336 ($\epsilon_m$ 10,300) and 261 n.m. (15,500); $\nu_{max.}$ (CHCl$_3$) 1795, 1735, 1690 cm$^{-1}$; δppm (CDCl$_3$) 1.21-1.39 (6H, m), 2.09 (3H, s), 2.87-3.14 (2H, m), 4.04 (1H, dd, J 4.1 and 7.8 Hz), 5.09-5.55 (3H, m), 5.73 (1H, d, J 4.1 Hz), 7.61 (2H, d, J 8.7 Hz), 8.22 (2H, d, J 8.7 Hz). (Found: M+, 452.0692. C$_{19}$H$_{20}$N$_2$O$_7$S$_2$ requires 452.0712).

PREPARATION 10(g)

(5RS,6SR,8SR)-p-Nitrobenzyl 6-(1-Acetoxyethyl)-2-ethylsulphinylpenem-3-carboxylate

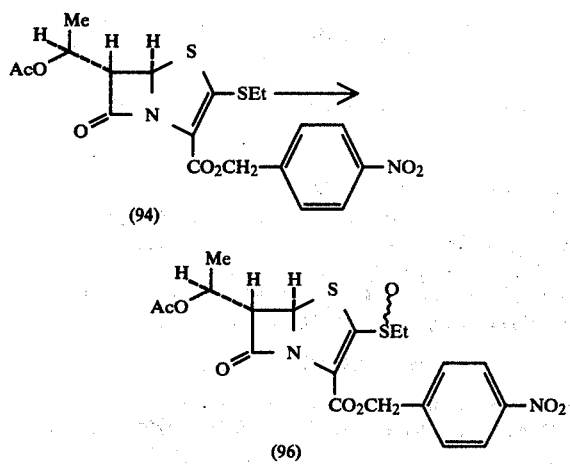

A solution of m-chloroperbenzoic acid (45 mg) in methylene chloride (1 ml) was added, in one portion, to a vigorously stirred, ice-bath cooled, mixture of the penem ester (94) (90 mg), methylene chloride (5 ml) and saturated sodium bicarbonate solution (5 ml). The mixture was stirred at ice-bath temperature for 10 minutes and diluted with methylene chloride (10 ml). The organic layer was separated and washed with brine (3×2 ml), dried (MgSO$_4$), evaporated and chromatographed to give the sulphoxide (96) (53 mg), an approximately 1:1 mixture of isomers, as an amorphous solid, $\nu_{max.}$ (CHCl$_3$) 1805, 1740 and 1710 cm$^{-1}$; δ ppm (CDCl$_3$) 1.32-1.50 (6H, m), 2.10 (3H, s), 2.9-3.3 (2H, m), 4.11 (1H, dd, J 2 and 4 Hz), 5.23 and 5.46 (ABq, J 14 Hz) plus 5.1-5.5 (m) together 3H, 5.59 (½H, d, J 2 Hz), 5.70 (½H, d, J 2 Hz), 7.59 and 7.60 (2H, each d, J 8 Hz), 8.25 (2H, d, J 8 Hz).

PREPARATION 10(h)

(5RS,6SR,8SR)-p-Nitrobenzyl 6-(1-Acetoxyethyl)-2-(2-pyridylthio)penem-3-carboxylate

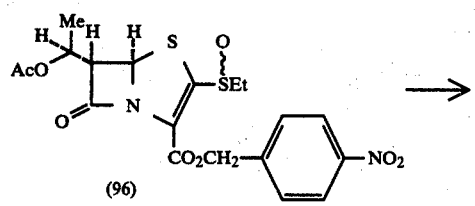

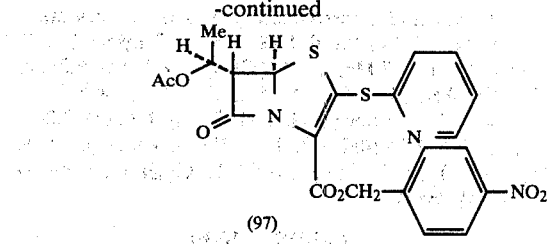

A stirred, ice-bath cooled, mixture of the penem sulphoxide (96) (50 mg), methylene chloride (5 ml), and water (2 ml) was treated with sodium 2-mercaptopyridine (16 mg) followed by benzyldimethyl-n-hexadecylammonium chloride (47 mg) portionwise over 5 minutes. The cooled mixture was stirred for a further 5 minutes, diluted with methylene chloride (10 ml) and washed successively with 5% citric acid (2 ml), brine (2 ml), saturated sodium bicarbonate solution (2 ml) and brine (3×2 ml). The dried (MgSO$_4$) organic layer was evaporated and chromatographed to give the penem ester (97) (22 mg) as a solid, m.p. 140°-142° C. (needles ex ethyl acetate/petroleum ether); $\lambda_{max.}$ (EtOH) 262 ($\epsilon_m$ 17,790) and 339 n.m. (12,090); $\nu_{max.}$ (CHCl$_3$) 1790, 1735, 1700 cm$^{-1}$; δ ppm (CDCl$_3$) 1.43 (3H, d, J 7 Hz), 2.10 (3H, s), 3.96 (1H, dd, J 1.7 and 3.9 Hz), 5.22-5.32 (1H, m), 5.30 and 5.50 (2H, ABq, J 14 Hz), 5.44 (1H, d, J 1.7 Hz), 7.25-734 (1H, m), 7.54-7.74 (4H, m), 8.20-8.27 (2H, m), 8.58-8.62 (1H, MO. (Found: C, 52.8; H, 4.0; N, 8.2; S, 12.5. C$_{22}$H$_{19}$N$_3$O$_7$S$_2$ requires C, 52.7; H, 3.8; N, 8.4; S, 12.8%).

EXAMPLE 10 (a)

(5RS)-p-Nitrobenzyl 6-Ethylidene-2-(2-pyridylthio)penem-3-carboxylate

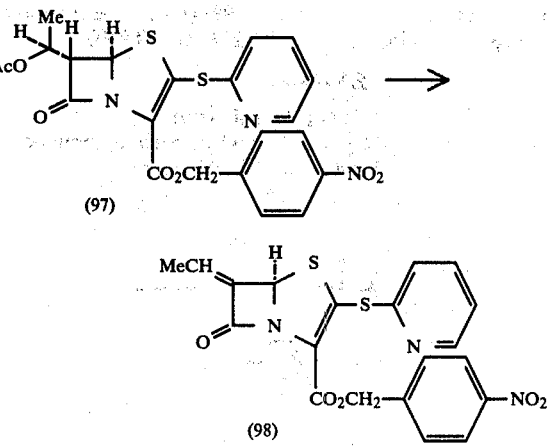

A solution of the penem ester (97) (55 mg) in dry methylene chloride (2 ml) was cooled to −20° C. and treated with a solution of 1,8-diazabicyclo-[5.4.0]undec-7-ene (DBU) (20 mg) in dry methylene chloride (1.2 ml). After stirring a −20° C. for 10 minutes the mixture was treated with DBU (5 mg) in dry methylene chloride (0.3 ml). After a further 10 minutes at −20° C. the mixture was diluted with ethyl acetate (15 ml) and washed with 5% citric acid (2 ml), brine (2 ml), saturated sodium bicarbonate solution (2 ml), and brine (3×2 ml). The dried (MgSO$_4$) organic layer was evaporated and chromatographed to give the 6-ethylidenepenem ester (98) (26 mg), an approximately 2:1 mixture of Z and E isomers, as a solid, $\lambda_{max}$. (EtOH) 261 (16,860) and approximately 316 n.m. (inflection); $\nu_{max}$. (CHCl$_3$) 1780 and 1700 cm$^{-1}$; $\delta$ ppm (CDCl$_3$) 1.76 ($\frac{2}{3}$CH$_3$, d, J 7 Hz), 2.08 ($\frac{1}{3}$CH$_3$, d, J 7 Hz), 5.25 and 5.51 (2H, ABq, J 14 Hz), 5.95 (q, J 7 Hz) plus 6.03 and 6.08 (each s) together (1$\frac{1}{3}$H, 6.44 ($\frac{2}{3}$H, q, J 7 Hz), 7.2–7.4 (1H, m), 7.5–7.75 (4H, m), 8.21 (2H, d, J 8 Hz), 8.5–8.7 (1H, m). (Found: M+, 441.0461. C$_{20}$H$_{15}$N$_3$O$_5$S$_2$ requires 441.0452).

EXAMPLE 10(b)

(5RS)-Sodium 6-Ethylidene-2-(2-pyridylthio)penem-3-carboxylate

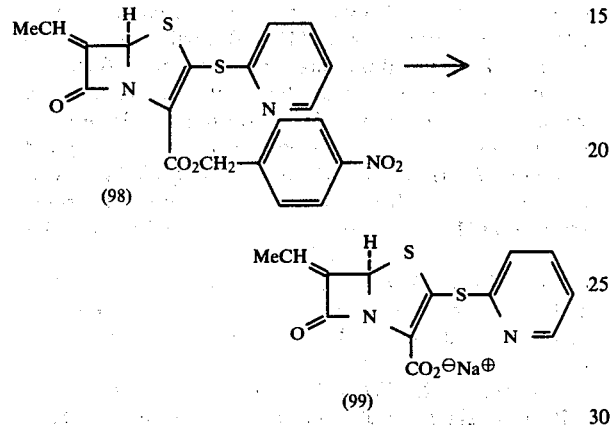

The 6-ethylidenepenem ester (98) (24 mg) was dissolved in a mixture of dioxan (8 ml) and water (2 ml) and hydrogenated over 5% palladium/charcoal catalyst (36 mg) at S.T.P. for 40 minutes. Further catalyst (24 mg) was added and the hydrogenation continued for 40 minutes. A 1% sodium bicarbonate solution (0.46 ml) was added and the mixture was worked up as for Example 1(b) to give the sodium salt (99) (8.2 mg) as a yellow amorphous solid, $\lambda_{max}$. (H$_2$O) 294 n.m. (6960).

EXAMPLE 11(a)

(5RS)-p-Nitrobenzyl 6-Ethylidene-2-(2-p-nitrobenzyloxycarbonylaminoethylthio)penem-3-carboxylate

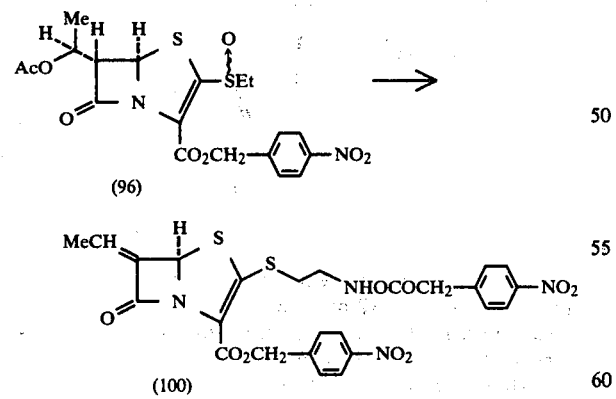

2-p-Nitrobenzyloxycarbonylaminoethanethiol (49 mg) was dissolved in 0.1N sodium hydroxide solution (1.9 ml), cooled in an ice-bath, and treated with a solution of the sulphoxide (96) (79 mg) in methylene chloride (5 ml). The stirred, ice-bath cooled, mixture was treated, portionwise over 5 minutes, with benzyldimethyl-n-hexadecylammonium chloride (75 mg). The cooled mixture was stirred for a further 10 minutes, diluted with methylene chloride (10 ml), and washed with 5% citric acid (2 ml), brine (2 ml), saturated sodium bicarbonate (2 ml), and brine (3×2 ml). The dried (MgSO$_4$) organic layer was evaporated and chromatographed to give the 6-ethylidenepenem ester (100) (46 mg), an approximately 2:1 mixture of E and Z isomers, as an amorphous solid, $\lambda_{max}$. (EtOH) 262 ($\epsilon_m$23,600) and approximately 314 n.m. (inflection); $\nu_{max}$. (CHCl$_3$) 3450, 1785, 1730, 1705 slight shoulder cm$^{-1}$; $\delta$ ppm (CDCl$_3$) 1.81 ($\frac{1}{3}$ CH$_3$, d, J 7 Hz), 2.10 ($\frac{2}{3}$ CH$_3$, d, J 7 Hz), 2.95–3.20 (2H, m), 3.35–3.65 (2H, m), 5.18 (s) plus 5.19 and 5.49 (ABq, J 14 Hz) plus 5.1–5.5 (m) together 5H, 6.02 ($\frac{2}{3}$H, q, J 7 Hz), 6.13 and 6.18 (1H, each s), 6.47 ($\frac{1}{3}$ H, q, J 7 Hz), 7.48 and 7.62 (4H, each d, J 8 Hz), 8.19 (4H, d, J 8 Hz).

EXAMPLE 11(b)

(5RS)-Sodium 2-(2-aminoethylthio)-6-ethylidenepenem-3-carboxylate

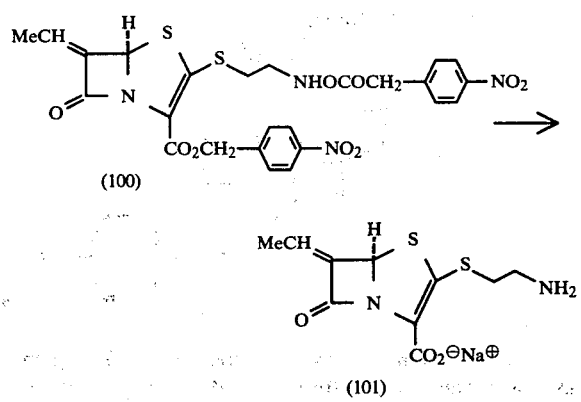

The 6-ethylidenepenem ester (100) (42 mg) was dissolved in a mixture of dioxan (8 ml), water (2 ml), and a 1% sodium bicarbonate solution (0.60 ml) and was hydrogenated over 5% palladium/charcoal catalyst (63 mg) at S.T.P. for 30 minutes. Further catalyst (42 mg) was added and the hydrogenation continued for 15 minutes. The mixture was filtered through Kieselguhr and worked up as for Example 1(b) to give the sodium salt (101) (1.6 mg), as 1:1 mixture of E and Z isomers, as an amorphous solid, $\delta$ ppm (D$_2$O) 1.85 ($\frac{1}{2}$ CH$_3$, d, J 7 Hz), 2.06 ($\frac{1}{2}$ CH$_3$, d, J 7 Hz), 3.00–3.34 (4H, m), 6.22 (q, J 7 Hz) and 6.24 (s) together 1H, 6.33 ($\frac{1}{2}$H, s), 6.58 ($\frac{1}{2}$H, q, J 7 Hz).

EXAMPLE 12(a)

(5RS)-p-Nitrobenzyl 6-Ethylidene-2-ethylsulphinylpenem-3-carboxylate

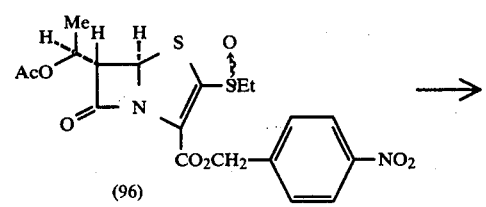

-continued

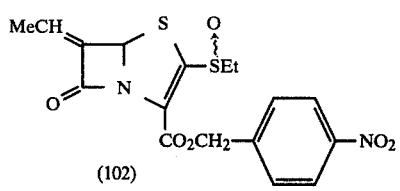
(102)

A solution of the penem sulphoxide (96) (60 mg) in dry methylene chloride (3 ml) was cooled to −20° C. and treated, dropwise, over 3 minutes, with a solution of 1,8-diazabicyclo [5.4.0]undec-7-ene (27 mg) in dry methylene chloride (4.2 ml). The mixture was stirred at −20° C. for 10 minutes and worked up as for Example 7 to give, after chromatography, the 6-alkylidenepenem sulphoxide ester (102) (30 mg) as an amorphous solid $\lambda_{max}$. (EtOH) 213 ($\epsilon_m$ 22,380), 261 (13,570) and 356 n.m. (5,420); $\nu_{max}$. (CHCl$_3$) 1790 and 1705 cm$^{-1}$; δ ppm (CDCl$_3$) 1.35–1.50 (3H, m), 1.87 and 1.89 (½ CH$_3$, each d, J 7 Hz), 2.16 and 2.18 (½ CH$_3$, each d, J 7 Hz), 3.03–3.24 (2H, m), 5.21–5.32 (1H, m), 5.41–5.52 (1H, m), 6.12 and 6.17 (½H, each dq, J 7 and 0.8 Hz), 6.23 and 6.25 (½H, each broadened s), 6.38 (½H, broadened s), 6.57 and 6.61 (½H, each dq, J 7 and 1.2 Hz), 7.60–7.68 (2H, m), 8.23–8.29 (2H, m). (Found: M+, 408.0410. C$_{17}$H$_{16}$N$_2$O$_6$S$_2$ requires M, 408.0447).

EXAMPLE 12(b)

(5RS)-Sodium 6-Ethylidene-2-ethylsulphinylpenem-3-carboxylate

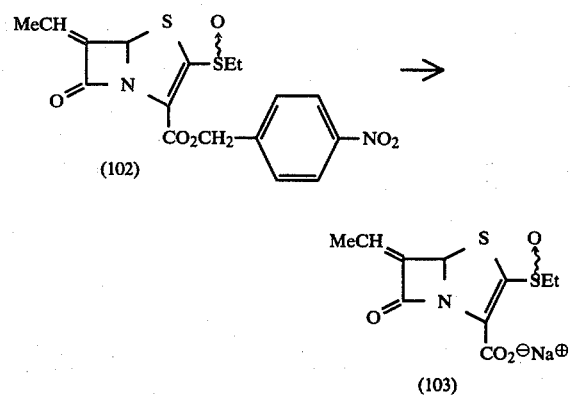

The 6-ethylidenepenem sulphoxide ester (102) (26 mg) was dissolved in a mixture of dioxan (8 ml) and water (2 ml) and hydrogenated over 5% palladium/charcoal catalyst (39 mg) at S.T.P. for 40 minutes. A 1% sodium bicarbonate solution (0.54 ml) was added and the mixture was worked up as for Example 1(b) to give the sodium salt (103) (12.2 mg) as an amorphous solid, $\lambda_{max}$. (H$_2$O) 222 ($\epsilon_m$, 13,490), 306 (3390) and approximately 335 n.m. (inflection); $\nu_{max}$. (KBr) 3700–3000, 1765, 1700, 1610, 1550 cm$^{-1}$.

EXAMPLE 13

(5RS)-p-Nitrobenzyl 6-Ethylidene-2-(2-p-nitrobenzyloxycarbonylaminoethylthio)penem-3-carboxylate

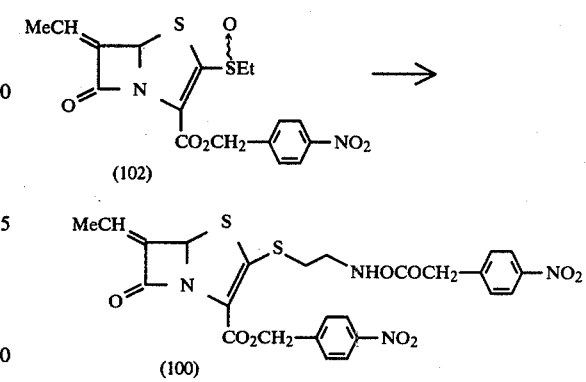

2-p-Nitrobenzyloxycarbonylaminoethanethiol (5.6 mg) was dissolved in 0.1N sodium hydroxide solution (0.22 ml), cooled in an ice-bath, and treated with a solution of the penem sulphoxide (9 mg) in methylene chloride (1 ml). The stirred, ice-bath cooled, mixture was treated, portionwise over 1 minute, with benzyldimethyl-n-hexadecylammonium chloride (8.7 mg). The mixture was stirred at ice-bath temperature for 10 minutes and worked up as for Example 11(a) to give the 6-ethylidenepenem ester (100) (5 mg), an approximately 1:1 mixture of E and Z isomers, as a gum (infra-red and n.m.r. data consistent with those obtained in Example 11(a).

PREPARATION 14(a)

(3ξ,4RS)-3-Bromo-3-{1-(ξ)-hydroxy-1-phenylmethyl}-1-(1-methoxycarbonyl-2-methylprop-1-enyl)-4-methylthioazetidin-2-one

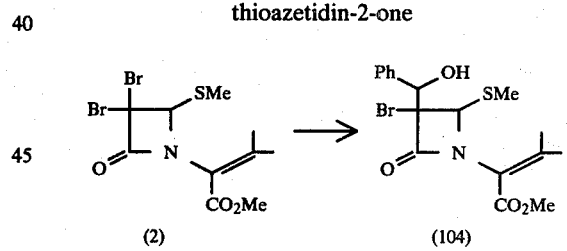

A solution of methyl magnesium bromide (2M in diethyl ether, 17.1 ml) was added, dropwise over 15 minutes, to a stirred solution of the dibromosecopenicillanate (2) (12.0 g) in dry tetrahydrofuran (120 ml) at −76° C. After stirring at −76° C. for a further 20 minutes a solution of redistilled benzaldehyde (3.96 g) in dry tetrahydrofuran (10 ml) was added dropwise over 10 minutes. The mixture was stirred at −76° C. for a further 10 minutes, treated with saturated ammonium chloride solution (60 ml) and allowed to attain room temperature. The mixture was diluted with ethyl acetate and the organic layer was separated. After washing with brine the dried (MgSO$_4$) organic layer was evaporated to give, after trituration with ether, the bromohydrin (104) (11.7 g as a solid, m.p. 111°–112° C. (plates ex ethyl acetate/hexane) $\nu_{max}$. (CHCl$_3$) 3600–3100, 1765, 1720 cm$^{-1}$; δ p.p.m. (CDCl$_3$) 1.85 (3H, s), 2.02 (3H, s), 2.19 (3H, s), 2.88 (1H, d, J 3 Hz), 3.49 (3H, s), 5.18 (1H, s), 5.25 (1H, d, J 3 Hz), 7.2–7.7 (5H, m). (Found: C, 49.5;

H, 4.8; N, 3.6; S, 7.6. $C_{17}H_{20}NBrO_4S$ requires C, 49.3; H, 4.8; N, 3.4; S, 7.7%).

PREPARATION 14(b)

(3RS,4RS)-3-{1-(RS)-Hydroxy-1-phenylmethyl} and (3RS,4SR)-3-{1-(SR)-Hydroxy-1-phenylmethyl}-1-(1-methoxycarbonyl-2-methylprop-1-enyl)-4-methylthioazetidin-2-ones

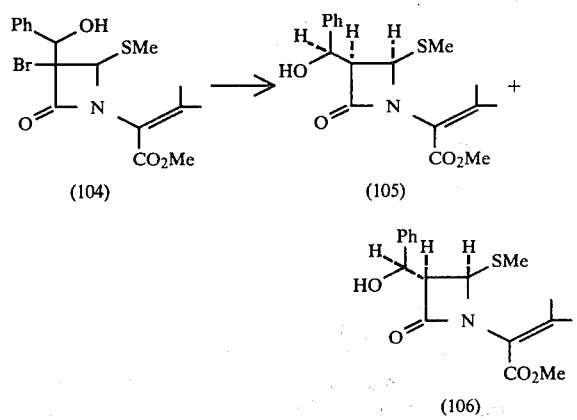

A stirred, ice-bath cooled, mixture of the bromohydrin (104) (11.7 g), tetrahydrofuran (120 ml) and aqueous ammonium acetate solution (1M., 24 ml) was treated with zinc powder (23.4 g). After stirring at ice-bath temperature for 30 minutes the mixture was treated with a further portion of zinc powder (2 g). The mixture was stirred at ice-bath temperature for a further 10 minutes and filtered through Kieselguhr, the residual zinc being washed with a little tetrahydrofuran. The combined filtrates were evaporated to low volume, diluted with ethyl acetate (300 ml) and washed successively with 1N. hydrochloric acid (20 ml), brine (20 ml), saturated sodium bicarbonate solution (20 ml) and brine (3×20 ml). The dried (MgSO$_4$) organic layer was evaporated and chromatographed to give an approximately 1:1 mixture of the (3RS,4RS)-3-{1-(RS)-hydroxy-1-phenylmethyl} and (3RS,4SR)-3-{1-(SR)-hydroxy-1-phenylmethyl} azetidinones (105) and (106) (8.60 g), $\nu_{max}$. (CHCl$_3$) 3600–3200, 1760, 1725 cm$^{-1}$; δ p.p.m. (CDCl$_3$) 1.92 (3H, s), 2.01 (3H, s), 2.19 (½ CH$_3$, s), 2.24 (½ CH$_3$, s), 2.5–3.3 (1H, broad signal, exch. D$_2$O), 3.49 (½H, dd, J 3 and 6½ Hz), 3.68 (½ CH$_3$, s), 3.73 (½ CH$_3$, s), 3.91 (½H, dd, J 5 and 7½ Hz), 4.82 (½H, d, J 3 Hz), 4.95–5.35 {1½H, m, collapses on exch. D$_2$O to 5.07 (d, J 6½ Hz), 5.09 (d, J 5 Hz) and 5.21 (d, J 7½ Hz)}, 7.2–7.6 (5H, m).

PREPARATION 14(c)

(3RS,4RS)-3-{1-(RS)-Acetoxy-1-phenylmethyl} and (3RS,4SR)-3-{1-(SR)-Acetoxy-1-phenylmethyl}-1-(1-methoxycarbonyl-2-methylprop-1-enyl)-4-methylthioazetidin-2-ones

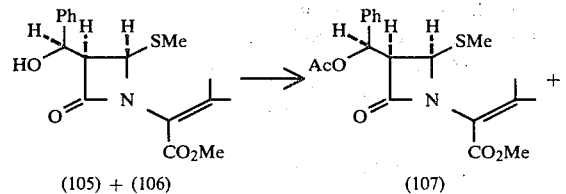

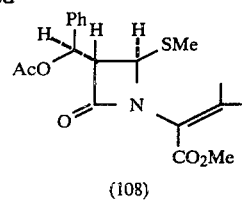

Acetic anhydride (3.14 g) was added dropwise over 5 minutes to a stirred, ice-bath-cooled, mixture of the azetidinones (105) and (106) (a 1:1 mixture, 8.60 g), triethylamine (3.11 g) and 4-dimethylaminopyridine (282 mg) in dry methylene chloride (100 ml). The mixture was stirred at room temperature for 1 hour and washed successively with 5% citric acid (30 ml), brine (30 ml), saturated sodium bicarbonate solution (30 ml) and brine (3×30 ml). The dried (MgSO$_4$) organic layer was evaporated and chromatographed to give two fractions. The less polar product, the (3RS,4SR)-3-{1-(SR)-acetoxy-1-phenylmethyl} azetidinone (108) (4.20 g) was obtained as a solid, m.p. 102°–104° C. (cubes ex ethyl acetate/hexane); $\nu_{max}$. (CHCl$_3$) 1760 and 1725 cm$^{-1}$; δ p.p.m. (CDCl$_3$) 1.89 (3H,s) 1.99 (3H, s), 2.11 (3H, s), 2.19 (3H, s), 3.55–3.75 (4H, m), 4.82 (1H, d, J 2½ Hz), 6.20 (1H, d, J 5 Hz), 7.2–7.6 (5H, m). (Found: C, 60.6; H, 6.1; N, 3.6; S, 8.3. $C_{19}H_{23}NO_5S$ requires C, 60.5; H, 6.1; N, 3.7; S, 8.5%). The more polar product, the (3RS,4RS)-3-{1-(RS)-acetoxy-1-phenylmethyl} azetidinone (107) (3.64 g) was obtained as a solid, m.p. 96°–97° C. (needles ex ethyl acetate/hexane); $\nu_{max}$. (CHCl$_3$) 1765 and 1725 cm$^{-1}$; δ p.p.m. (CDCl$_3$) 1.96 (3H, s), 2.05 and 2.07 (6H, each s), 2.21 and (3H, s), 3.71 (3H, s), 4.03 (1H, dd, J 5 and 9 Hz), 5.13 (1H, d, J 5 Hz), 6.16 (1H, d, J 9 Hz), 7.2–7.6 (5H, m). (Found: C, 60.9; H, 6.1; N, 3.6; S, 8.4. $C_{19}H_{23}NO_5S$ requires C, 60.5; H, 6.1; N, 3.7; S, 8.5%).

PREPARATION 14(d)

(3RS,4RS)-3-{1-(RS)-Acetoxy-1-phenylmethyl}-4-methylsulphonylazetidin-2-one

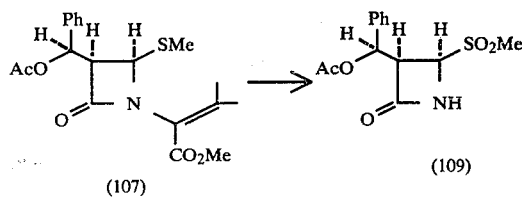

A solution of m-chloroperbenzoic acid (3.53 g) in ethyl acetate (20 ml) was added dropwise over 15 minutes to a stirred, ice-bath-cooled, solution of the cis-azetidinone (107) (3.50 g) in ethyl acetate (70 ml). The mixture was stirred at room temperature for 1 hour when a solid precipitated. The mixture was diluted with methylene chloride (100 ml) and the resulting solution was washed with saturated sodium bicarbonate solution (2×50 ml) and brine (3×50 ml). The dried (MgSO$_4$) organic layer was cooled to −20° C. and treated with ozonised oxygen for 1 hour. The excess ozone was removed by passage of argon and the mixture evaporated. The residue was dissolved in a mixture of methanol (100 ml) and methylene chloride (400 ml) and treated with 2,6-lutidine (40 drops). The mixture was stirred at room temperature for 10 minutes and evaporated to give, after trituration with ether, the sulphone (109) (2.44 g), as a solid, m.p. 178°-82° C. (fine needles ex acetone/ether); $v_{max}$. (Nujol) 3370, 1795, 1730 cm$^{-1}$; δ p.p.m. {(CD$_3$)$_2$CO} 3.03 (3H, s), 4.38 (1H, dd, J 5 and 12 Hz with further fine coupling which collapsed on exch. D$_2$O), 5.10 (1H, d, J 5 Hz), 6.43 (1H, d, J 12 Hz), 7.2–7.5 (5H, m), 8.1–8.4 (1H, broad signal, exch. D$_2$O). (Found: C, 52.7; H, 5.1; N, 4.6; S, 10.7. C$_{13}$H$_{15}$NO$_5$S requires C, 52.5; H, 5.1; N, 4.7; S, 10.8%).

PREPARATION 14(e)

(3RS,4SR)-3-{1-(RS)-Acetoxy-1-phenylmethyl}-4-ethylthiothiocarbonylthioazetidin-2-one

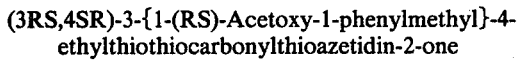

Potassium ethyltrithiocarbonate (1.50 g) was added to an ice-bath cooled mixture of the sulphone (109) (2.30 g), methylene chloride (200 ml) and water (40 ml). The mixture was stirred at room temperature for 1½ hours and worked up as for preparation 1(f) to give the trithiocarbonate (110) (2.01 g) as a yellow gum, $v_{max}$. (CHCl$_3$) 3410, 1785, 1750 shoulder cm$^{-1}$; δ p.p.m. (CDCl$_3$) 1.34 (3H, t, J 7 Hz), 2.10 (3H, s), 3.32 (2H, q, J 7 Hz), 3.66 (1H, dd, J 2 and 5 Hz), 5.65 (1H, d, J 2 Hz), 6.19 (1H, d, J 5 Hz), 6.62 br (1H, s, exch. D$_2$O), 7.32 (5H, s).

PREPARATION 14(f)

(3RS,4SR)-3-{1-(RS)-Acetoxy-1-phenylmethyl}-4-ethylthiothiocarbonylthio-1-(1-p-nitrobenzyloxycarbonyl-1-triphenylphosphoranylidenemethyl)azetidin-2-one

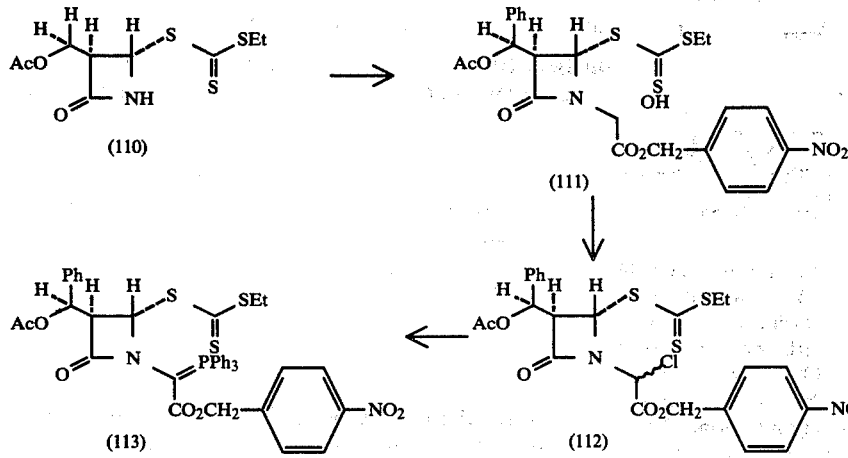

A mixture of the trithiocarbonate (110) (2.01 g) and p-nitrobenzyl glyoxylate monohydrate (1.42 g) was heated in refluxing benzene (100 ml) in a Dean and Stark apparatus containing molecular sieves (type 4A). After 1 hour the mixture was cooled and treated with triethylamine (57 mg). The mixture was kept at room temperature for 15 minutes and evaporated to give the crude hydroxyester (111), $v_{max}$. (CHCl$_3$) 3700–3100, 1785, 1755 cm$^{-1}$.

A solution of thionyl chloride (1.01 g) in dry tetrahydrofuran (5 ml) was added, dropwise over 5 minutes, to a stirred solution of the crude hydroxyester (111) and 2,6-lutidine (910 mg) in dry tetrahydrofuran (60 ml) at −10° C. The mixture was stirred at −10° C. for 10 minutes, filtered and evaporated. The residue was re-evaporated from dry toluene (2×10 ml) to give the crude chloroester (112) as a gum, $v_{max}$. (CHCl$_3$) 1795, 1760 cm$^{-1}$.

A mixture containing the crude chloroester (112), triphenylphosphine (2.97 g) and 2,6-lutidine (727 mg) in dry dioxan (60 ml) was stirred at 60° C. under dry argon for 36 hours. The mixture was worked up as for preparation 1(i) to give, after chromatography, the phosphorane (113) (3.17 g) as an amorphous solid, $v_{max}$. (CHCl$_3$) 1765, 1620, 1610 shoulder cm$^{-1}$.

PREPARATION 14(g)

(5RS,6SR,8SR)- and (5RS,6RS,8RS)-p-Nitrobenzyl 6-(1-Acetoxy-1-phenylmethyl)-2-ethylthiopenem-3-carboxylate

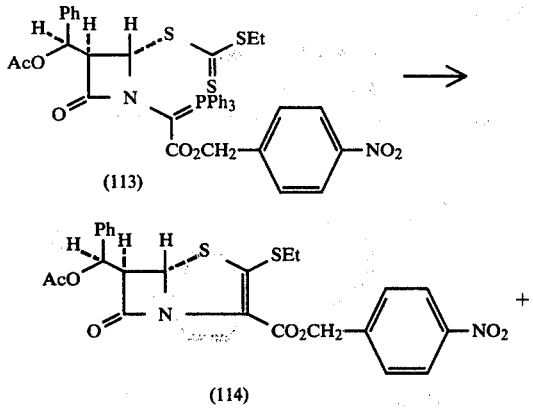

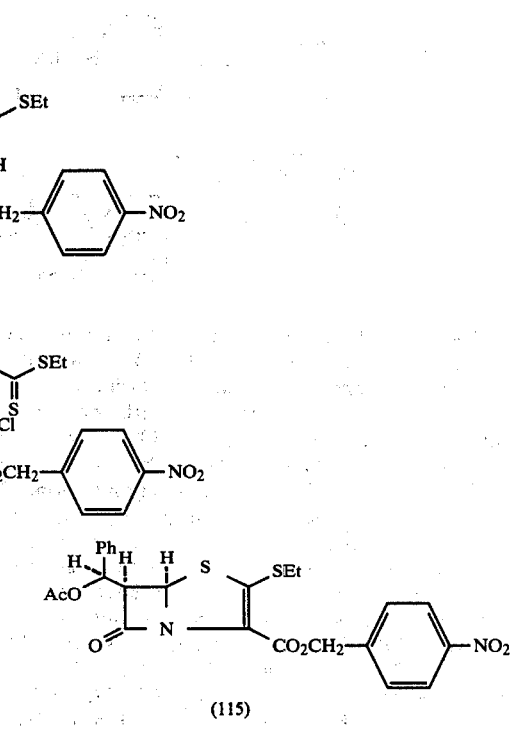

A solution of the phosphorane (113) (2.97 g) in xylene (1500 ml) was refluxed under argon for 8½ hours. The mixture was evaporated and chromatographed to give two products. The less polar product, the (5RS,6RS,8RS) penem ester (115) (195 mg), was obtained as a pale yellow solid, m.p. 176°-178° C. (plates ex ethyl acetate/hexane); λ$_{max}$. (EtOH) 260 (ε$_m$ 15,860) and 335 n.m. (10,650); ν$_{max}$. (CHCl$_3$) 1795, 1745, 1690 cm$^{-1}$; δ p.p.m. (CDCl$_3$) 1.39 (3H, t, J 7 Hz), 2.06 (3H, s), 2.9-3.2 (2H, m), 4.42 (1H, dd, J 4 and 10 Hz), 5.12 and 5.40 (2H, ABq, J 14 Hz), 5.78 (1H, d, J 4 Hz), 6.11 (1H, d, J 10 Hz), 7.38 (5H, s), 7.52 (2H, d, J 9 Hz), 8.14 (2H, d, J 9 Hz). (Found: C, 56.1; H, 4.4; N, 5.4. C$_{24}$H$_{22}$N$_2$O$_7$S$_2$ requires C, 56.0; H, 4.3; N, 5.4%). The more polare product, the (5RS,6SR,8SR) penem ester (114) (740 mg), was obtained as pale yellow solid, m.p. 157°-159° C. (plates ex ethyl acetate/hexane; λ$_{max}$. (EtOH) 261 (ε$_m$ 15,930) and 339 n.m. (9840); ν$_{max}$. (CHCl$_3$) 1795, 1740, 1690 cm$^{-1}$; δ p.p.m. (CDCl$_3$) 1.34 (3H, t, J 7 Hz), 2.10 (3H, s), 2.78-3.12 (2H, m), 4.18 (1H, dd, J 1.7 and 6 Hz), 5.19 and 5.42 (2H, ABq, J 14 Hz), 5.64 (1H, d, J 1.7 Hz), 6.18 (1H, d, J 6 Hz), 7.33 (5H, s), 7.58 (2H, d, J 9 Hz), 8.19 (2H, d, J 9 Hz). (Found: C, 56.3; H, 4.4; N, 5.5 C$_{24}$H$_{22}$N$_2$O$_7$S$_2$ requires C, 56.0; H, 4.3; N, 5.4%).

EXAMPLE 14(a)

(5RS)-p-Nitrobenzyl (Z)-6-Benzylidene-2-ethylthiopenem-3-carboxylate

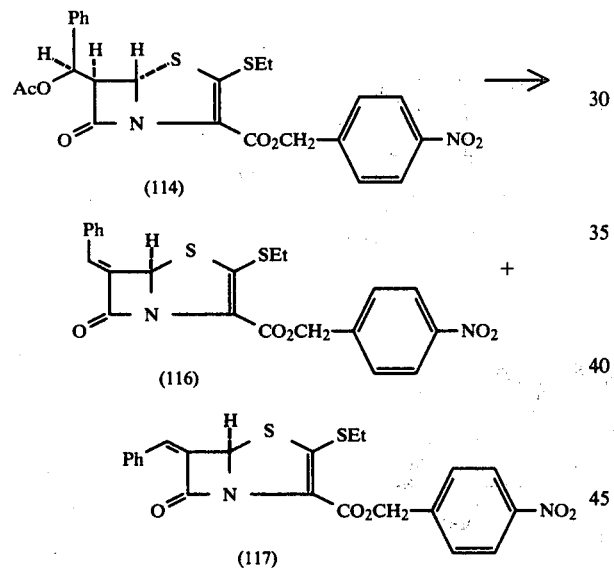

A solution of 1,8-diazabicyclo{5.4.0}-undec-7-ene (44 mg) in dry methylene chloride (1 ml) was added, dropwise over 1 minute, to a stirred solution of the trans-penem ester (114) (100 mg) in dry methylene chloride (4 ml) at −40° C. After stirring at −40° C. for 10 minutes the mixture was diluted with methylene chloride (10 ml) and washed with 5% citric acid (2 ml), brine (2 ml), saturated sodium bicarbonate solution (2 ml) and brine (3×2 ml). The dried (MgSO$_4$) organic layer was evaporated and chromatographed to give two fractions. The less polar product, the (E)-benzylidenepenem ester (117) (12 mg) was obtained as a yellow solid, ν$_{max}$. (CHCl$_3$) 1770, 1690 cm$^{-1}$; δ p.p.m. (CDCl$_3$) 1.37 (3H, t, J 7 Hz), 2.73-3.25 (2H, m), 5.23 and 5.51 (2H, ABq, J 14 Hz), 6.29 (1H, s), 6.61 (1H, s), 7.3-7.5 (3H, m), 7.67 (2H, d, J 9 Hz) 7.85-8.05 (2H, m), 8.23 (2H, d, J 9 Hz). The more polar product, the (Z)-benzylidenepenem ester (116) (64 mg) was obtained as a yellow solid, m.p. 178°-179° C. (fine needles ex ethyl acetate/hexane); λ$_{max}$. (EtOH) 286 (ε$_m$ 31,450) and approximately 328 n.m. (inflection); ν$_{max}$. (CHCl$_3$) 1780, 1690 cm$^{-1}$; δ p.p.m. (CDCl$_3$) 1.35 (3H, t, J 7 Hz), 2.65-3.25 (2H, m), 5.22 and 5.49 (2H, ABq, J 14 Hz), 6.49 (1H, s), 7.12 (1H, s), 7.2-7.5 (5H, m), 7.65 (2H, d, J 9 Hz), 8.20 (2H, d, J 9 Hz). (Found: M$^+$, 454.0686. C$_{22}$H$_{18}$N$_2$O$_5$S$_2$ requires 454.0654).

EXAMPLE 14(b)

(5RS)-Sodium (Z)-6-Benzylidene-2-ethylthiopenem-3-carboxylate

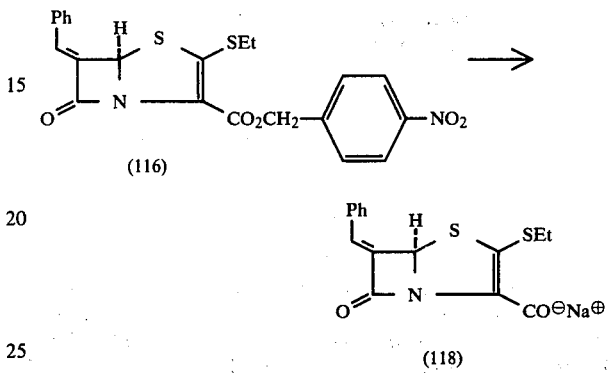

The (Z)-benzylidenepenem ester (116) (50 mg) was dissolved in a mixture of dioxan (8 ml) and water (2 ml) and hydrogenated over 5% palladium/charcoal catalyst at S.T.P. for 40 minutes. Further catalyst (50 mg) was added and the hydrogenation continued for 40 minutes. A 1% sodium bicarbonate solution (0.93 ml) was added and the mixture worked up as for Example 1(b) to give the sodium salt (118) (12.6 mg) as a yellow-orange amorphous solid, λ$_{max}$. (H$_2$O) 291 (ε$_m$ 21,870) and 380 n.m. (2,140); δ p.p.m. (D$_2$O) 1.27 (3H, t, J 7 Hz), 2.68-2.98 (2H, m), 6.49 (1H, s), 7.1 (1H, s), 7.32-7.56 (5H, m).

PREPARATION 15(a)

(3ξ,4RS)-3-Bromo-3(2-hydroxyprop-2-yl)-1(1-methoxycarbonyl-2-methylprop-1-enyl)-4-methylthioazetidin-2-one

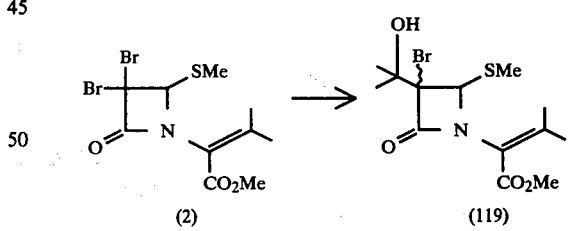

A solution of methyl magnesium bromide (2M in diethyl ether, 20 ml) was added, dropwise over five minutes, to a stirred solution of the dibromosecopenicillanate (2) (13.6 g) in dry tetrahydrofuran (250 ml) at −76° C. After stirring at −76° C. for further ten minutes a mixture of dry acetone (5.2 ml) and tetrahydrofuran (10 ml) was added dropwise over five minutes. The mixture was stirred at −76° C. for a further twenty minutes, treated with a saturated aqueous solution of ammonium chloride (10 ml) and allowed to attain room temperature. Excess of tetrahydrofuran was evaporated in vacuo and the residue was partitioned between ethyl acetate and water. The organic layer was washed with brine, dried (MgSO$_4$) and evaporated to give a pale cream crystalline solid. This was recrystallised from ethyl acetate/petroleum ether to give colourless rhombs, m.p. 130°-131.5° C. (8.0 g). {Chromatography of the mother liquors gave a further portion (1.2 g) of product.} $\nu_{max}$. (CHCl$_3$) 3550, 3400 (b), 1760, 1720, 1625 (w) cm$^{-1}$; δ p.p.m. (CDCl$_3$) 1.45 (3H, s) 1.57 (3H, s) 2.04 (3H, s) 2.16 (3H, s) 2.26 (4H, s, 1H, exchangeable with D$_2$O), 3.77 (3H, s) 5.46 (1H, s). (Found: C, 42.5; H, 5.5; N, 3.8; S, 8.7; Br, 21.9. C$_{13}$H$_{20}$NO$_4$SBr requires C, 42.6; H, 5.5; N, 3.8; S, 8.7; Br, 21.9%).

PREPARATION 15(b)

(3RS,4RS) and (3RS,4SR)-3(2-Hydroxyprop-2-yl)-1(1-methoxycarbonyl-2-methylprop-1-enyl)-4-methylthioazetidin-2-one

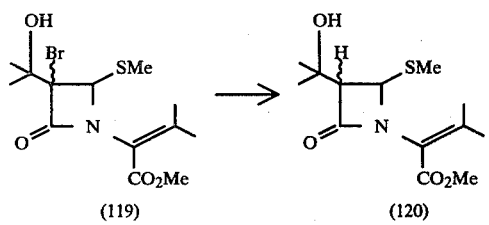

The bromohydrin (119) (7 g) in tetrahydrofuran (100 ml) at room temperature was stirred vigorously with zinc dust (14 g) and N aqueous ammonium acetate solution (14 ml) for 30 minutes. The mixture was filtered and after evaporation in vacuo of most of the solvent the residue was partitioned between ethyl acetate and water. The organic layer was washed with N/10 hydrochloric acid, sodium bicarbonate solution then brine. The dried (MgSO$_4$) organic layer was evaporated and the product was chromatographed on silica gel eluting with ethyl acetate/petroleum ether mixtures to give 2:1 mixture of the trans and cis-hydroxyisopropylazetidinones (120) as a gum (5.2 g) $\nu_{max}$. 3600, 3500 (b), 1750, 1720, 1630 cm$^{-1}$; δ p.p.m. (CDCl$_3$) 1.35 (s), 1.42 (s), 1.46 (s), 1.50 (s) (together 6H), 2.00 (s), 2.04 (s), 2.12 (s), 2.15 (s), 2.22 (s), 2.26 (s) (together 9H) overlaying (⅔H, exchangeable with D$_2$O) 2.71 (⅓H, exchangeable with D$_2$O) 3.16 (⅔H, d, J 3 Hz), 3.54 (⅓H, d, J 5 Hz), 3.76 (3H, s), 5.04 (d, J 3 Hz) and 5.07 (d, J 5 Hz) (together 1H).

PREPARATION 15(c)

(3RS,4RS)-3(2-Hydroxyprop-2-yl)-4-methylsulphonylazetidin-2-one

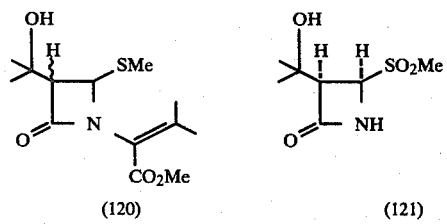

A solution of m-chloroperbenzoic acid (6.4 g) in dichloromethane (50 ml) was added over five minutes to an ice-cooled solution of azetidinone (120) (cis/trans mixture) (4.55 g) in dichloromethane (50 ml). The mixture was kept at room temperature for 30 minutes and was then washed twice with saturated solution, twice with dilute sodium bicarbonate solution, then dried (MgSO$_4$).

The solution was then diluted to 100 ml with dichloromethane, cooled to −60° C. and ozonised oxygen was passed for 2 h with the temperature gradually rising to −10° C. Argon was passed through the solution for five minutes then methanol (100 ml) and 2,6-lutidine (10 drops) were added. After one hour the mixture was concentrated to low volume and white crystals were filtered off (1.63 g) white rhombs 205°-208° (from ethyl acetate) $\nu_{max}$. (CHCl$_3$) 3500, 3300 (b), 1785 cm$^{-1}$. δ p.p.m. (CD$_3$COCD$_3$) 1.52 (6H, s), 3.18 (3H, s), 4.04 (1H, dd, J 6, 1 Hz) 4.22 (1H, s, exchangeable with D$_2$O) 5.14 (1H, d, J 6 Hz) 8.0-8.5 (1H, m, exchangeable with D$_2$O (Found: C, 40.5; H, 6.3; N, 6.6; S, 15.1. C$_7$H$_{13}$NO$_4$S requires C,40.6; H, 6.2; N, 6.8, S, 15.5%).

PREPARATION 15(d)

(3RS,4SR)-3(2-Hydroxyprop-2-yl)-4-ethylthiothiocarbonylthioazetidin-2-one

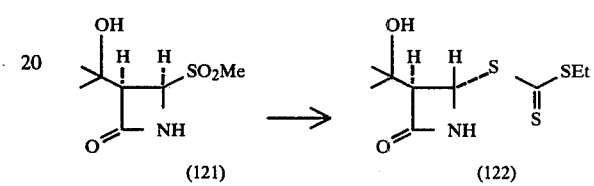

The sulphone (121) (1.38 g) in dichloromethane (15 ml) was vigorously stirred with a solution of potassium ethyltrithiocarbonate (1.25 g) in water (15 ml) at room temperature for 20 minutes. The solvent layer was separated, washed with water, dried (MgSO$_4$) and evaporated to give the trithiocarbonate (122) (1.25 g) as a yellow solid; $\nu_{max}$. (CHCl$_3$) 3600, 3420, 1770, cm$^{-1}$; δ p.p.m. (CDCl$_3$) 1.29 (s), 1.36 (t, J 7 Hz) 1.43 (s), together 9H, 2.00 (1H, s, exchangeable with D$_2$O) 3.22 (d, J 2 Hz), 3.55 (q, J 7 Hz) together 3H, 5.62 (1H, d, J 2 Hz) 6.64 (1H, b.s., exchangeable with D$_2$O). (Found: M$^+$, 265.0269. C$_9$H$_{15}$NO$_2$S$_3$ requires M, 265.0265).

PREPARATION 15(e)

(3RS,4SR)-4-Ethylthiothiocarbonylthio-1(1-hydroxy-1-p-nitrobenzyloxycarbonylmethyl)-3(2-hydroxyprop-2-yl)azetidin-2-one

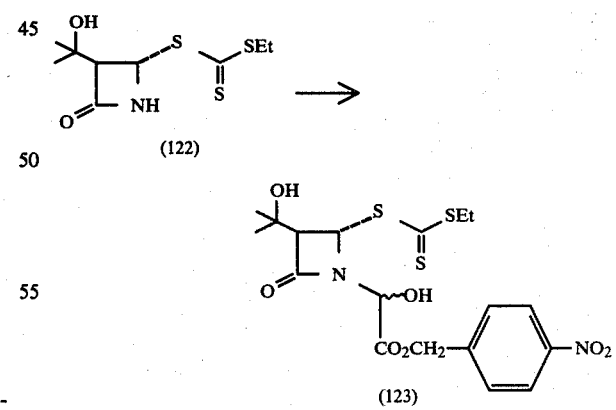

The trithiocarbonate (122) (1.14 g) and p-nitrobenzyl glyoxylate monohydrate (1.95 g) were refluxed in benzene (100 ml) for three hours with constant removal of water. The mixture was then evaporated and chromatographed on silica gel eluting with ethyl acetate/petroleum ether mixtures to give the hydroxy-ester (123) (1.6 g) as a mixture of stereoisomers—a gum, $\nu_{max}$. (CHCl$_3$) 3600-3200, 1775, 1760 cm$^{-1}$; δ p.p.m. (CDCl$_3$)

1.40 (s), 1.47 (t, J 7 Hz) 1.56 (s) (together 9H), 2.9 (1H, b.s., exchangeable with D₂O) 3.5 (q, J 7 Hz) overlaying 3.5 (d, J 2 Hz) (together 3H), 4.85 (1H, d, J 8 Hz exchangeable with D₂O) 5.4 and 5.5 (2H, 2s) 5.77 (1H, d, J 8 Hz) 6.3, 6.37 (1H, 2d, J 2 Hz) 7.7 and 8.3 (4H, 2d, J 8 Hz).

PREPARATION 15(f)

(3RS,4SR)-1(1-Chloro-1-p-nitrobenzyloxycarbonylmethyl)-4-ethylthiothiocarbonylthio-3-(2-hydroxyprop-2-yl)azetidin-2-one

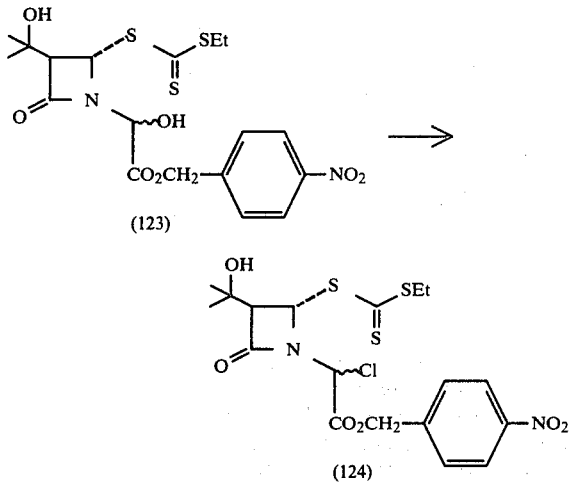

The hydroxy-ester (123) (mixed stereoisomers) (464 mg) in dry tetrahydrofuran (20 ml) at −15° C. was treated with 2,6-lutidine (115 mg) followed by thionyl chloride (0.08 ml) for 10 minutes. The mixture was filtered and the filtrate was evaporated to give the chloro-ester (124) as a yellow gum.

PREPARATION 15(g)

(3RS,4SR)-4-Ethylthiothiocarbonylthio-3(2-hydroxyprop-2-yl)-1(1-p-nitrobenzyloxycarbonyl-1-triphenylphosphoranylidenemethyl)azetidin-2-one

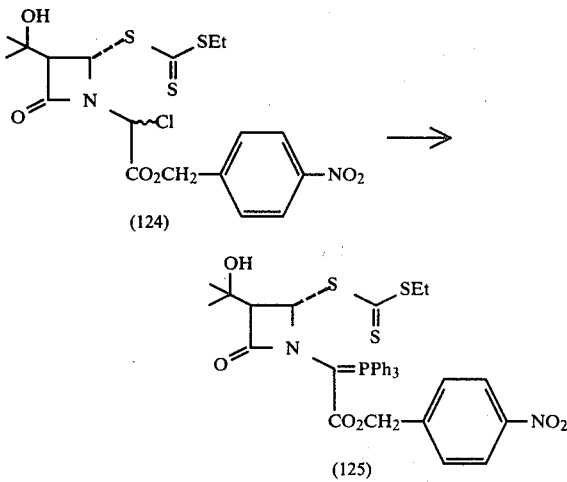

The total chloro-ester (124) from preparation 15(f) in dioxan (40 ml) was heated with triphenylphosphine (510 mg) and lutidine (45 mg) at 60° for 24 hours. The mixture was then evaporated in vacuo and the residue partitioned between ethyl acetate and dilute aqueous citric acid. The organic layer was then separated and washed with water, aqueous sodium bicarbonate then brine. The solution was dried (MgSO₄) and evaporated then the residual gum was chromatographed on silica gel eluting with ethyl acetate/petroleum ether mixtures to give the phosphorane (125) (250 mg) as a yellow amorphous solid, $\nu_{max}$. (CHCl₃) 3600, 3450 (b), 1755, 1620 cm⁻¹.

PREPARATION 15(h)

(5RS,6SR) and (5RS,6RS)-p-Nitrobenzyl 2-Ethylthio-6(2-hydroxyprop-2-yl)penem-3-carboxylate

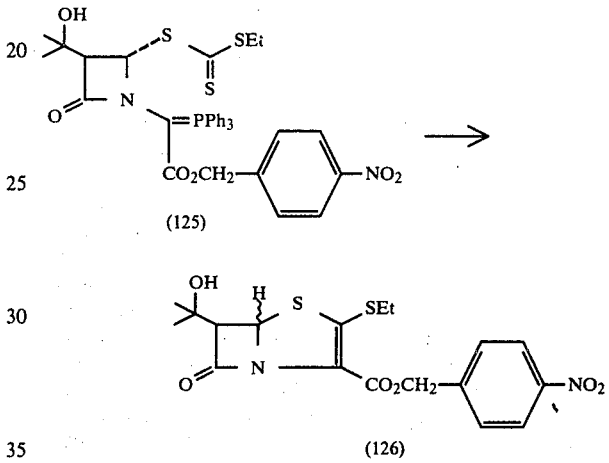

The phosphorane (125) (1.05 g) was refluxed in dry xylene (300 ml) for 12 hours, finally evaporating to dryness in vacuo. The residue was chromatographed on silica gel eluting with ethyl acetate/petroleum ether mixtures giving a fraction consisting of a mixture of cis and trans isomers of the penem (126) and a less mobile fraction of unchanged phosphorane which was recovered (143 mg). Rechromatography of the penem fraction on silica gel eluting with diethyl ether/dichloromethane 1:9 gave the pure trans isomer of (126) (274 mg) preceded by a 1:1 mixture of cis and trans penems (126) (20 mg). The pure trans isomer was an off-white solid, needles m.p. 156°. $\lambda_{max}$. (EtOH) 340 n.m. ($\epsilon_m$ 10,680) 261 n.m. (16,430) $\nu_{max}$. 3600, 3500 (b), 1790, 1690, 1610 cm⁻¹. δ p.p.m. (CDCl₃) 1.34 (s) 1.35 (t, J 7 Hz) 1.43 (s) (together 9H) 1.94 (1H, s, exchangeable with D₂O) 2.96 (2H, q, J 7 Hz with fine coupling) 3.76 (1H, d, J 1½ Hz), 5.18 and 5.48 (2H, ABq, J 14 Hz) 5.64 (1H, d, J 1½ Hz 7.60 and 8.19 (4H, 2d, J 8 Hz). (Found: M+, 424.0740, C₁₈H₂₀N₂O₆S₂ requires M, 424.0718). The cis/trans mixuture showed the following n.m.r. signals charcteristic of the cis compound: δ p.p.m. (CDCl₃) 2.34 (s, exchangeable with D₂O) 4.01 (d, J 4 Hz), 5.74 (d, J 4 Hz).

EXAMPLE 15(a)

(5RS,6SR)-p-Nitrobenzyl 2-Ethylthio-6(2-methylsulphonyloxyprop-2-yl)penem-3-carboxylate

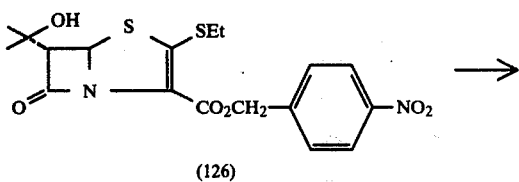

(126)

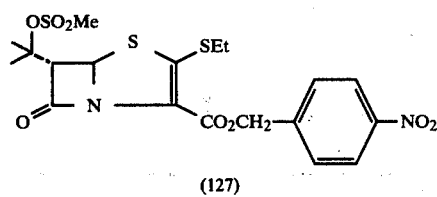

(127)

To a solution of the hydroxy-penem (126) (69 mg) in dry tetrahydrofuran at −76° C. under Ar was added a solution prepared by adding butyl lithium solution in n-hexane (1.6N, 0.2 ml) to diisopropylamine (20 mg) in tetrahydrofuran (5 ml) at −76° C. After 4 minutes methylsulphonyl chloride (3 drops) was added and stirring was continued at low temperature for five minutes then the mixture was allowed to reach room temperature. Chromatography on silica gel eluting with ethyl acetate/petroleum ether mixtures gave first mesyloxypenem (127) (26 mg) as a gum, $\nu_{max}$. (CHCl$_3$) 1790, 1697 cm$^{-1}$. followed by some recovered hydroxypenem (126) (21 mg) (identified by t.l.c. and infra-red spectrum).

EXAMPLE 15(b)

(5RS) p-Nitrobenzyl 2-Ethylthio-6-isopropylidenepenem-3-carboxylate

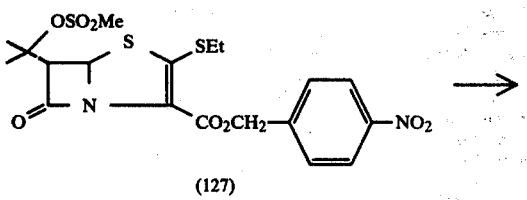

(127)

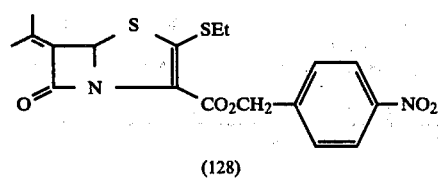

(128)

The mesylate (127) (26 mg) in chloroform (2 ml) was treated at room temperature with 1,8-diazabicyclo{5.4.0}undec-7-ene (1 drop). After 10 minutes the mixture was diluted with ethyl acetate, washed with dilute aqueous citric acid then with brine, dried (MgSO$_4$) and evaporated in vacuo. The residue was chromatographed on silica gel eluting with ethyl acetate/n-hexane 3:7 mixture. The product zone crystallised on standing (8 mg) m.p. 175°–176° from ethyl acetate/n-hexane. $\lambda_{max}$. (EtOH) 322 n.m. ($\epsilon_m$ 8,100) 256 (16,070), $\nu_{max}$. (KBr) 1762, 1720, 1675, 1600 cm$^{-1}$. δ p.p.m. (CDCl$_3$) 1.38 (3H, t, J 7.4 Hz) 1.83 (3H, s) 2.14 (3H, s) 2.96 (2H, q, J 7.4 Hz) 5.22 and 5.50 (2H, ABq, J 14 Hz) 6.15 (1H, s) 7.66 and 8.24 (4H, 2d, J 9 Hz). (Found: M+: 406.0634, C$_{18}$H$_{18}$N$_2$O$_5$S$_2$ requires M, 406.0657).

EXAMPLE 15(c)

(5RS)-Sodium 2-Ethylthio-6-isopropylidenepenem-3-carboxylate

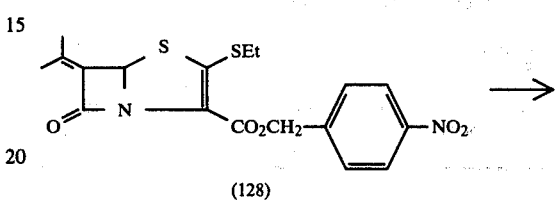

(128)

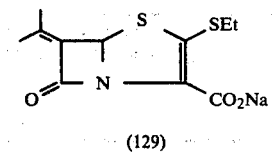

(129)

A solution of isopropylidene-penem ester (128) (5 mg) in dioxan (4 ml) and water (1 ml) was hydrogenated at atmospheric pressure over 5% palladium on carbon catalyst (5 mg) for 30 minutes. A further portion of catalyst (5 mg) was added and hydrogenation was continued at room temperature for 30 minutes longer. The mixture was filtered through Kieselguhr. Sodium bicarbonate (1.2 mg) in water (0.12 ml) was then added and the mixture was evaporated in vacuo. The residue was worked up as in Example 1(b) to give the sodium salt (129) as an amoprhous solid (2 mg), $\lambda_{max}$. (H$_2$O) 290 n.m.

BIOLOGICAL DATA

1. Antibacterial activity

The antibacterial activity of a number of compounds described in the foregoing Examples against a number of organisms is shown in Tables 1 and 10.

2. β-Lactamase inhibitory activity

The β-lactamase inhibitory activity of the compound of Example 1 is demonstrated by the synergistic properties shown in Tables 2–5. These tables show the MIC values of amoxycillin, cephaloridine, ticarcillin and apalcillin against a number of β-lactamase producing organisms. In each case, the addition of the compound of Example 1 shows a marked decrease in the MIC.

Similar data for the compound of Example 2 are given in Tables 6 to 8.

Data demonstrating the β-lactamase inhibitory activity of further compounds of the Examples in combination with amoxycillin are given in Tables 9 and 11.

TABLE I

| | Broth MIC Values (μg/ml) for 6-Ethylidenepenems Compound number - See Examples | | | | | | | | |
|---|---|---|---|---|---|---|---|---|---|
| Organism | (27) | (29) | (40) | (49) | (59) | (76) | (99) | (101) | (103) |
| C. freundii E 8 | 31 | 62 | 125 | 125 | 25 | 100 | 100 | 100 | >100 |
| E. cloacae N 1 | 31 | 31 | 125 | 62 | 25 | >100 | 25 | 100 | >100 |

TABLE I-continued

| Organism | Broth MIC Values (µg/ml) for 6-Ethylidenepenems Compound number - See Examples | | | | | | | | |
|---|---|---|---|---|---|---|---|---|---|
| | (27) | (29) | (40) | (49) | (59) | (76) | (99) | (101) | (103) |
| E. coli 0111 | 31 | 31 | 62 | 125 | 25 | 100 | 100 | 100 | >100 |
| E. coli JT 39 R+ | 16 | 31 | 62 | 62 | 12.5 | 100 | 50 | 100 | >100 |
| E. coli ESS | 16 | 2 | 16 | 1 | 3.1 | 6.2 | 3.1 | 12.5 | 100 |
| K. aerogenes A | 16 | 16 | 62 | 31 | 12.5 | >100 | 50 | 100 | >100 |
| P. mirabilis 977 | 31 | 125 | 250 | 62 | 25 | 100 | 100 | >100 | 100 |
| P. morganii I 580 | 31 | 31 | 250 | 31 | 25 | 100 | 50 | >100 | >100 |
| P. rettgeri WM 16 | 62 | 62 | 125 | 62 | 25 | >100 | 25 | 100 | >100 |
| P. vulgaris WO 91 | 31 | 62 | 250 | 62 | 25 | >100 | 50 | 100 | >100 |
| P. aeruginosa A | >500 | >500 | 250 | >250 | >100 | 100 | >100 | >100 | >100 |
| S. typhimurium CT 10 | 16 | 62 | 62 | 62 | 12.5 | 100 | 50 | 100 | >100 |
| S. marcescens US 20 | 62 | 62 | 250 | 125 | 25 | >100 | 50 | >100 | >100 |
| S. sonnei MB 11967 | 31 | 62 | 62 | 62 | 25 | 100 | 50 | 100 | >100 |
| B. subtilis A | — | 2 | 31 | 1 | 3.1 | 25 | 6.2 | 12.5 | 25 |
| S. aureus Oxford | 2 | 2 | 8 | 1 | 3.1 | 12.5 | 12.5 | 3.1 | 50 |
| S. aureus Russell | 4 | — | 16 | 2 | 3.1 | 6.2 | 6.2 | 3.1 | >100 |
| S. aureus 1517 | 16 | 16 | 125 | 62 | >100 | 50 | 100 | >100 | >100 |
| S. faecalis I | 250 | 250 | >250 | 125 | 100 | >100 | >100 | >100 | >100 |
| S. pneumoniae CN 33 | 2 | 1 | 31 | ≦0.2 | 0.2 | — | — | — | 25 |
| S. pyogenes CN 10 | 4 | 4 | 8 | — | ≦0.1 | — | 1.6 | 3.1 | 12.5 |

TABLE 2

Activity of Amoxycillin Alone or in Combination with Compound of Example 1 MIC (µg/ml)

| Organism | Amoxycillin Alone | Amoxycillin + compound of Example 1 | |
|---|---|---|---|
| | | (5.0 µg/ml) | (1.0 µg/ml) |
| E. coli 0111 | 10 | 5.0 | 5.0 |
| E. coli JT410 C+ | 250 | 250 | 500 |
| E. coli JT39R+ | >1000 | 5.0 | 25 |
| E. coli JT20R+ | >1000 | 25 | 100 |
| K. aerogenes A | 100 | 0.5 | 1.0 |
| K. aerogenes I112 | 500 | 2.5 | 2.5 |
| K. aerogenes Ba95R+ | >1000 | 50 | 250 |
| P. mirabilis 977 | 2.5 | 2.5 | 2.5 |
| P. mirabilis 889 | >1000 | 100 | 500 |
| P. morganii 1580 | 1000 | 50 | 250 |
| P. rettgeri WM16 | 1000 | 50 | 250 |
| P. vulgaris WO91 | >1000 | 1.0 | 2.5 |
| E. cloacae N1 | 500 | 25 | 50 |
| S. marcescens US20 | 50 | 50 | 50 |
| C. freundii E8 | 250 | 100 | 250 |
| C. freundii B10R+ | >1000 | 500 | >1000 |
| P. aeruginosa A | >1000 | >1000 | >1000 |
| P. aeruginosa Dalgleish | >1000 | >1000 | >1000 |
| S. aureus Russell | 100 | ≦0.2* | 0.5 |
| S. aureus MB9 | 25 | ≦0.2* | 0.5 |

*Compound alone inhibitory

TABLE 3

Activity of Cephaloridine alone or in Combination with Compound of Example 1 MIC (µg/ml)

| Organisms | Cephaloridine Alone | Cephaloridine + Compound of Example 1 | |
|---|---|---|---|
| | | (5.0 µg/ml) | (1.0 µg/ml) |
| E. coli 0111 | 2.5 | 2.5 | 2.5 |
| E. coli JT410C+ | 50 | 50 | 50 |
| E. coli JT39R+ | 5.0 | 2.5 | 2.5 |
| E. coli JT20R+ | 25 | 2.5 | 2.5 |
| K. aerogenes A | 2.5 | 1.0 | 2.5 |
| K. aerogenes I112 | 5.0 | 2.5 | 2.5 |
| K. aerogenes Ba95R+ | 100 | 2.5 | 5.0 |
| P. mirabilis 977 | 10 | 10 | 10 |
| P. mirabilis 889 | 250 | 5.0 | 5.0 |
| P. morganii 1580 | 1000 | 10 | 100 |
| P. retterri WM16 | 1000 | 5.0 | 100 |
| P. vulgaris WO91 | 1000 | 5.0 | 5.0 |
| E. cloacae N1 | 500 | 2.5 | 5.0 |
| S. marcescens US20 | 1000 | 25 | 100 |
| C. freundii E8 | 500 | 25 | 100 |
| C. freundii B10R+ | >1000 | 100 | 250 |
| P. aeruginosa A | >1000 | >1000 | >1000 |
| P. aeruginosa Dalgleish | >1000 | >1000 | >1000 |
| S. aureus Russell | 0.5 | <0.2* | <0.2 |
| S. aureus MB9 | <0.2 | <0.2* | <0.2 |

TABLE 4

Activity of Ticarcillin alone or in Combination with Compound of Example 1 MIC (µg/ml)

| Organism | Ticarcillin Alone | Ticarcillin + Compound of Example 1 | |
|---|---|---|---|
| | | (5.0 µg/ml) | (1.0 µg/ml) |
| E. coli 0111 | 5.0 | 5.0 | 5.0 |
| E. coli JT410 C+ | 10 | 10 | 10 |
| E. coli JT39 R+ | >1000 | 10 | 25 |
| E. coli JT20 R+ | >1000 | 50 | 250 |
| K. aerogenes A | 100 | 1.0 | 1.0 |
| K. aerogenes I112 | 500 | 5.0 | 5.0 |
| K. aerogenes Ba95R+ | >1000 | 100 | 500 |
| P. mirabilis 977 | 1.0 | 11.0 | 2.5 |
| P. mirabilis 889 | >1000 | 250 | 1000 |
| P. morganii 1580 | 250 | 2.51 | 2.5 |
| P. rettgeri WM16 | 25 | 2.5 | 5.0 |
| P. vulgaris WO91 | 25 | 2.5 | 5.0 |
| E. cloacae N1 | 2.5 | 1.0 | 1.0 |
| S. marcescens US20 | 5.0 | 5.0 | 5.0 |
| C. freundii E8 | 2.5 | 5.0 | 2.5 |
| C. freundii B10R+ | >1000 | 500 | >1000 |
| P. aeruginosa A | 25 | 25 | 25 |
| P. aeruginosa Dalgleish | >1000 | >1000 | >1000 |
| S. aureus Russell | 25 | <0.2* | 1.0 |
| S. aureus MB9 | 10 | <0.2* | 1.0 |

*Compound alone inhibitory

TABLE 3-continued

Activity of Cephaloridine alone or in Combination with Compound of Example 1 MIC (µg/ml)

| Organisms | Cephaloridine Alone | Cephaloridine + Compound of Example 1 | |
|---|---|---|---|
| | | (5.0 µg/ml) | (1.0 µg/ml) |
| S. aureus MB9 | <0.2 | <0.2* | <0.2 |

TABLE 5

Activity of Apalcillin alone or in Combination with Compound of Example 1 MIC (µg/ml)

| Organism | Apalcillin Alone | Apalcillin + Compound of Example 1 | |
|---|---|---|---|
| | | (5.0 µg/ml) | (1.0 µg/ml) |
| E. coli 0111 | 2.5 | 2.5 | 2.5 |
| E. coli JT410C+ | 25 | 25 | 25 |
| E. coli JT39R+ | 1000 | 2.5 | 2.5 |
| E. coli JT20R+ | >1000 | 2.5 | 5.0 |
| K. aerogenes A | 10 | <0.2 | 0.5 |
| K. aerogenes I112 | 25 | 1.0 | 1.0 |
| K. aerogenes Ba95R+ | >1000 | 2.5 | 10 |
| P. mirabilis 977 | 2.5 | 1.0 | 1.0 |

TABLE 5-continued

Activity of Apalcillin alone or in Combination with Compound of Example 1 MIC (μg/ml)

| Organism | Apalcillin Alone | Apalcillin + Compound of Example 1 | |
|---|---|---|---|
| | | (5.0 μg/ml) | (1.0 μg/ml) |
| P. mirabilis 889 | >1000 | 5.0 | 25 |
| P. morganii 1580 | 1000 | 10 | 10 |
| P. rettgeri WM16 | 10 | 10 | 10 |
| P. vulgaris WO91 | 10 | 1.0 | 2.5 |
| E. cloacae N1 | 5.0 | 5.0 | 5.0 |
| S. marcescens US20 | 5.0 | 5.0 | 5.0 |
| C. freundii E8 | 2.5 | 2.5 | 5.0 |
| C. freundii B10R+ | >1000 | 5.0 | 1000 |
| P. aeruginosa A | 2.5 | 2.5 | 2.5 |
| P. Dalgleish | >1000 | 250 | >1000 |
| S. aureus Russell | 250 | <0.2* | 2.5 |
| S. aureus MB9 | 50 | <0.2* | 1.0 |

*Compound alone inhibitory

TABLE 6

Activity of Amoxycillin Alone and in Combination with Compound of Example 2 MIC (μg/ml)

| Organism | Amoxycillin Alone | Amoxycillin + compound of Example 2 | |
|---|---|---|---|
| | | (5.0 μg/ml) | (1.0 μg/ml) |
| E. coli 0111 | 10 | 5.0 | 5.0 |
| E. coli JT410 C+ | 500 | 100 | 250 |
| E. coli JT39R+ | >1000 | 5.0 | 25 |
| E. coli JT20R+ | >1000 | 25 | 250 |
| P. mirabilis 977 | 2.5 | 2.5 | 1.0 |
| P. mirabilis 889 | >1000 | 250 | 1000 |
| P. morganii 1580 | 1000 | 100 | 250 |
| P. rettgeri WM16 | 1000 | 100 | 250 |
| P. vulgaris WO91 | >1000 | 1.0 | 1.0 |
| K. aerogenes I112 | 500 | 2.5 | 5.0 |
| K. aerogenes Ba95R+ | >1000 | 100 | 1000 |
| E. cloacae N1 | 500 | 12.5 | 250 |
| S. marcescens US20 | 100 | 50 | 50 |
| C. freundii E8 | 250 | 50 | 100 |
| C. freundii B10R+ | >1000 | 500 | >1000 |
| P. aeruginosa A | >1000 | >1000 | >1000 |
| P. aeruginosa Dalgleish | >1000 | >1000 | >1000 |
| S. aureus Russell | 100 | ≦0.2* | 0.5 |

TABLE 7

Activity of Cephaloridine alone and in Combination with Compound of Example 2 MIC (μg/ml)

| Organisms | Cephaloridine Alone | Cephaloridine + Compound of Example 2 | |
|---|---|---|---|
| | | (5.0 μg/ml) | (1.0 μg/ml) |
| E. coli 0111 | 5.0 | 2.5 | 2.5 |
| E. coli Jt410C+ | 100 | 10 | 50 |
| E. coli JT39R+ | 10 | 2.5 | 2.5 |
| E. coli JT20Rhd + | 25 | 2.5 | 2.5 |
| P. mirabilis 977 | 5.0 | 5.0 | 10 |
| P. mirabilis 889 | 100 | 5.0 | 10 |
| P. morganii 1580 | >1000 | 25 | 100 |
| P. rettgeri WM16 | >1000 | 10 | 100 |
| P. vulgaris WO91 | >1000 | 2.5 | 5.0 |
| K. aerogenes I112 | 5.0 | 2.5 | 5.0 |
| K. aerogenes Ba95R+ | 100 | 2.5 | 5.0 |
| E. cloacae N1 | 1000 | 2.5 | 10 |
| S. marcescens US20 | >1000 | 50 | 250 |
| C. freundii E8 | 500 | 25 | 100 |
| C. freundii B10R+ | >1000 | 500 | 1000 |
| P. aeruginosa A | >1000 | >1000 | >1000 |
| P. aeruginosa Dalgleish | >1000 | >1000 | >1000 |
| S. aureus Russell | <0.2 | <0.2 | <0.2 |

TABLE 8

Activity of Ticarcillin alone and in Combination with Compound of Example 2 MIC (μg/ml)

| Organism | Ticarcillin Alone | Ticarcillin + Compound of Example 2 | |
|---|---|---|---|
| | | (5.0 μg/ml) | (1.0 μg/ml) |
| E. coli 0111 | 5.0 | 5.0 | 5.0 |
| E. coli JT410C+ | 25 | 10 | 25 |
| E. coli JT39R+ | >1000 | 10 | 50 |
| E. coli JT20R+ | >1000 | 50 | 500 |
| P. mirabilis 977 | 1.0 | 1.0 | 1.0 |
| P. mirabilis 889 | >1000 | 250 | >1000 |
| P. morganii 1580 | 10 | 2.5 | 2.5 |
| P. rettgeri WM16 | 10 | 2.5 | 2.5 |
| P. vulgaris WO91 | 500 | 1.0 | 10 |
| K. aerogenes I112 | 250 | 5.0 | 25 |
| K. aerogenes Ba95R+ | >1000 | 250 | >1000 |
| E. cloacae N1 | 2.5 | 2.5 | 2.5 |
| S. marcescens US20 | 5.0 | 10 | 5.0 |
| C. freundii E8 | 5.0 | 10 | 5.0 |
| C. freundii B10R+ | >1000 | >1000 | >1000 |
| P. aeruginosa A | 25 | 25 | 25 |
| P. aeruginosa Dalgleish | >1000 | >1000 | >1000 |
| S. aureus Russell | 25 | <0.2* | 2.5 |

TABLE 9

Amoxycillin MIC Values (μg/ml) in combination with 6-Alkylidenepenems

| Organism | None | (40) 5 μg/ml | (49) 5 μg/ml | (59) 2.5 μg/ml | (76) 2 μg/ml | (99) 5 μg/ml | (101) 2.5 μg/ml | (103) 5 μg/ml |
|---|---|---|---|---|---|---|---|---|
| E. coli 0111 | 5 | 2.5 | 5 | 2.5 | 2.5 | 5 | 5 | 2.5 |
| E. coli JT 410 C+ | 500 | 100 | 500 | 100 | 250 | 500 | 250 | 500 |
| E. coli JT 39 R+ | >1000 | 5 | 10 | 1 | 50 | 50 | 50 | 500 |
| E. coli JT 20 R+ | >1000 | 25 | 100 | 10 | 1000 | 1000 | 500 | >1000 |
| P. mirabilis C 977 | 2.5 | 2.5 | 2.5 | 0.5 | 0.5 | 1 | 1 | 2.5 |
| P. mirabilis C 889 | >1000 | >1000 | 100 | 50 | >1000 | 250 | >1000 | >1000 |
| P. vulgaris WO 91 | 1000 | 5 | 1 | 0.5 | 0.5 | 1 | 5 | 100 |
| P. morganni I 580 | >1000 | 250 | 100 | 50 | 250 | 250 | 500 | 500 |
| P. rettgeri WM 16 | 1000 | 250 | 250 | 50 | 250 | 500 | 500 | 500 |
| K. aerogenes A | 250 | 1 | 1 | 0.5 | 1 | 1 | 2.5 | 5 |
| K. aerogenes I 112 | 500 | 2.5 | 5 | 0.5 | 10 | 25 | 25 | 25 |
| K. aerogenes Ba 95 R+ | >1000 | 50 | 100 | 10 | >1000 | 1000 | >1000 | >1000 |
| E. cloacae N I | 500 | 250 | 50 | 25 | 500 | 100 | 250 | 100 |
| S. marcescens US 20 | 1000 | 250 | 100 | 50 | 10 | 50 | 250 | 100 |
| C. freundii E 8 | 500 | 50 | 100 | 25 | 10 | 250 | 100 | 100 |
| C. freundii B 10 R+ | >1000 | 250 | >1000 | 1000 | >1000 | >1000 | >1000 | >1000 |
| P. aeruginosa A | >1000 | >1000 | >1000 | >1000 | >1000 | >1000 | >1000 | >1000 |
| P. aeruginosa Dalgleish | >1000 | >1000 | >1000 | >1000 | >1000 | >1000 | >1000 | >1000 |
| S. aureus Russell | 100 | ≦0.2 | ≦0.2 | ≦0.2 | 5 | ≦0.2 | ≦0.2 | 50 |

TABLE 9-continued

Amoxycillin MIC Values (μg/ml) in combination with 6-Alkylidenepenems

| Organism | None | (40) (5 μg/ml) | (49) (5 μg/ml) | (59) (2.5 μg/ml) | (76) (2 μg/ml) | (99) (5 μg/ml) | (101) (2.5 μg/ml) | (103) (5 μg/ml) |
|---|---|---|---|---|---|---|---|---|
| S. aureus MB 9 | 250 | 1 | — | ≦0.2 | 10 | ≦0.2 | ≦0.2 | 100 |

TABLE 10

Broth MIC values (μg/ml) for 6-Alkylidenepenems

| Organism | Compound (118) | Compound (129) |
|---|---|---|
| C. freundii E 8 | >100 | — |
| E. cloacae N 1 | >100 | — |
| E. coli 0111 | >100 | — |
| E. coli JT 39 R+ | >100 | — |
| E. coli ESS | >1.6 | 12.5 |
| K. aerogenes A | >100 | — |
| P. mirabilis 977 | >100 | — |
| P. morganii 580 | >100 | — |
| P. rettgeri WM 16 | >100 | — |
| P. vulgaris WO 91 | >100 | — |
| P. aeruginosa A | >100 | — |
| S. typhimurium CT 10 | >100 | — |
| S. marcescens US 20 | >100 | — |
| S. sonnei MB 11967 | >100 | — |
| B. subtilis A | 12.5 | 25 |
| S. aureus Oxford | 1.6 | 12.5 |
| S. aureus Russell | 3.1 | 12.5 |
| S. aureus 1517 | 100 | — |
| S. faecalis I | >100 | 50 |
| S. pneumoniae CN 33 | 1.6 | 1.6 |
| S. pyogenes CN 10 | 1.6 | 0.4 |

TABLE 11

Amoxycillin MIC Values (μg/ml) in combination with 6-Benzylidenepenem (118)

| Organism | Amoxycillin alone | Amoxycillin + Compound (118) | |
|---|---|---|---|
| | | (5.0 μg/ml) | (1.0 μg/ml) |
| E. coli 0111 | 5.0 | 2.5 | 5.0 |
| E. coli JT 410 C+ | 250 | 100 | 250 |
| E. coli JT 39 R+ | 1000 | 10 | 50 |
| E. coli JT 20 R+ | >1000 | 100 | 500 |
| P. mirabilis C 977 | 2.5 | 2.5 | 2.5 |
| P. mirabilis C 889 | >1000 | 100 | 250 |
| P. morganii I 580 | >1000 | 100 | 500 |
| P. rettgeri WM 16 | 500 | 100 | 500 |
| P. vulgaris WO 91 | >1000 | 5.0 | 25 |
| K. aerogenes A | 250 | 2.5 | 5.0 |
| K. aerogenes I 112 | 250 | 10 | 50 |
| K. aerogenes Ba 95 R+ | >1000 | 100 | 500 |
| E. cloacae N 1 | 500 | 100 | 250 |
| E. cloacae T 153 | 1000 | 500 | 1000 |
| S. marcescens US 20 | 100 | 25 | 25 |
| C. freundii E 8 | 250 | 25 | 50 |
| C. freundii B 10 R+ | >1000 | 1000 | >1000 |
| P. aruginosa A | >1000 | 500 | >1000 |
| P. aeruginosa Dalgleish | >1000 | >1000 | >1000 |
| S. aureus Russell | 100 | ≦0.2 | ≦0.2 |
| S. aureus MB 9 | 100 | ≦0.2 | ≦0.2 |

I claim:

1. A compound of formula (II):

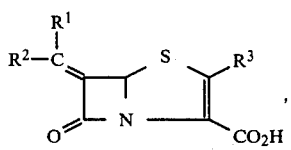

(II)

a pharmaceutically acceptable salt or pharmaceutically acceptable in-vivo hydrolysable ester thereof, wherein $R^1$ and $R^2$ are the same or different and each is hydrogen, alkyl of 1 to 6 carbon atoms, phenyl or a non-toxic heterocyclic group unsubstituted or substituted with a pharmaceutically acceptable functional group; and $R^3$ is hydrogen, $R^a$ or —$SR^a$ wherein $R^a$ is alkyl of 1 to 6 carbon atoms or phenyl unsubstituted or substituted by hydroxy, alkoxy of 1-6 carbon atoms, alkanoyloxy of 1-6 carbon atoms, halo, mercapto, alkylthio of 1-6 carbon atoms, amino, mono- or dialkylamino of 1-6 carbon atoms in the alkyl moiety, alkanoylamino of 1-6 carbon atoms, carboxy or alkoxycarbonyl of 1-6 carbon atoms; or $R^3$ is pyridylthio.

2. A compound according to claim 1 wherein $R^1$ and $R^2$ are each hydrogen or a hydrocarbon of 1-10 carbon atoms.

3. A compound according to claim 1 wherein $R^1$ and $R^2$ are each hydrogen or alkyl of 1-6 carbon atoms.

4. A compound according to claim 1 wherein $R^1$ and $R^2$ are hydrogen, methyl, ethyl or phenyl.

5. A compound according to claim 1 wherein $R^3$ is hydrogen, aminomethyl, aminomethyl, methylthio, ethylthio, 2-aminoethylthio, 2-hydroxyethylthio, methyl, ethyl, acetamidoethyl, pyridylthio or ethylsulphinyl.

6. A compound according to claim 1 in the form of a pharmaceutically acceptable in-vivo hydrolyzable ester wherein the ester moiety is of the formulae (a), (b) or (c):

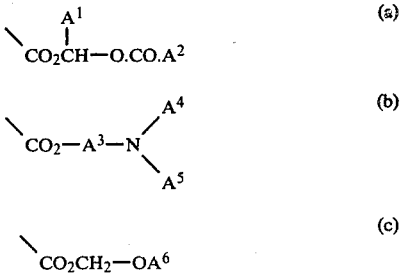

wherein $A^1$ is hydrogen, methyl or phenyl; $A^2$ is alkyl of 1-6 carbon atoms, alkoxy of 1-6 carbon atoms or phenyl; or $A^1$ and $A^2$ together form a 1,2-phenylene moiety unsubstituted or substituted by one or two methoxy groups; $A^3$ is alkyl of 1-6 carbon atoms unsubstituted or substituted by methyl or ethyl; $A^4$ and $A^5$ are alkyl of 1-6 carbon atoms; and $A^6$ is alkyl of 1-6 carbon atoms.

7. A compound according to claim 1 in the form of a pharmaceutically acceptable in-vivo hydrolyzable ester wherein the ester is acetoxymethyl, pivaloyloxymethyl, α-acetoxyethyl, α-acetoxybenzyl, α-pivaloyloxyethyl, ethoxycarbonyloxymethyl, α-ethoxycarbonyloxyethyl, dimethylaminomethyl, diethylaminomethyl, diethylaminoethyl, phthalidyl or dimethoxyphthalidyl.

8. A compound according to claim 1 in the form of a pharmaceutically acceptable salt wherein said salt is an alkali metal salt or an alkaline earth metal salt.

9. A compound according to claim 1 in the form of a pharmaceutically acceptable salt wherein the salt is the sodium, potassium, calcium, magnesium, ammonium or a substituted ammonium salt, wherein the substituent is lower alkyl, hydroxy-lower alkyl or cycloalkyl, procaine, dibenzylamine, N,N-dibenzylethylenediamine, 1-ephenamine, N-ethylpiperidine, N-benzyl-β-phenethylamine, dehydroabetiylamine, N,N'-bisdehydroabietylethylenediamine, pyridine, collidine or quinoline.

10. The compound according to claim 1 which is 6-(Z)-ethylidene-2-ethylthiopenem-3-carboxylic acid.

11. The compound according to claim 1 which is 6-(E)-ethylidene-2-ethylthiopenem-3-carboxylic acid.

12. The compound according to claim 1 which is 6-(Z)-ethylidenepenem-3-carboxylic acid.

13. The compound according to claim 1 which is 6-(Z)-ethylidene-2-n-propylpenem-3-carboxylic acid.

14. The compound according to claim 1 which is 2-(2-acetamidoethylthio)-6-ethylidenepenem-3-carboxylic acid.

15. The compound according to claim 1 which is 6-(Z)-ethylidene-2-methylpenem-3-carboxylic acid.

16. The compound according to claim 1 which is 6-ethylidene-2-(2-pyridylthio)penem-3-carboxylic acid.

17. The compound according to claim 1 which is 2-(2-aminoethylthio)-6-ethylidenepenem-3-carboxylic acid.

18. The compound according to claim 1 which is 6-ethylidene-2-ethylsulphinylpenem-3-carboxylic acid.

19. The compound according to claim 1 which is 6-(Z)-benzylidene-2-ethylthiopenem-3-carboxylic acid.

20. The compound according to claim 1 which is 2-ethylthio-6-isopropylidenepenem-3-carboxylic acid.

21. A pharmaceutical composition useful for treating bacterial infections in humans and animals which comprises an antibacterially effective amount or a β-lactamase inhibitory amount of a compound of the formula (II):

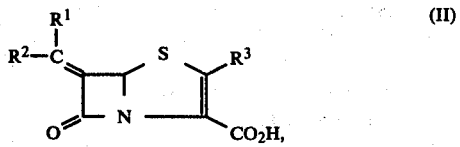

a pharmaceutically acceptable salt or pharmaceutically acceptable in-vivo hydrolysable ester thereof, wherein $R^1$ and $R^2$ are the same or different and each is hydrogen, alkyl of 1 to 6 carbon atoms, phenyl or a non-toxic heterocyclic group unsubstituted or substituted with a pharmaceutically acceptable functional group; and $R^3$ is hydrogen, $R^a$ or $-SR^a$ wherein $R^a$ is alkyl of 1 to 6 carbon atoms or phenyl unsubstituted or substituted by hydroxy, alkoxy of 1-6 carbon atoms, alkanoyloxy of 1-6 carbon atoms, halo, mercapto, alkylthio of 1-6 carbon atoms, amino, mono- or dialkylamino of 1-6 carbon atoms in the alkyl moiety, alkanoylamino of 1-6 carbon atoms, carboxy or alkoxycarbonyl of 1-6 carbon atoms; or $R^3$ is pyridylthio, in combination with a pharmaceutically acceptable carrier.

22. A composition according to claim 21 wherein $R^1$ and $R^2$ are each hydrogen or a hydrocarbon of 1-10 carbon atoms.

23. A composition according to claim 21 wherein $R^1$ and $R^2$ are each hydrogen or alkyl of 1-6 carbon atoms.

24. A composition according to claim 21 wherein $R^1$ and $R^2$ are hydrogen, methyl, ethyl or phenyl.

25. A composition according to claim 21 wherein $R^3$ is hydrogen, aminomethyl, aminoethyl, methylthio, ethylthio, 2-aminoethylthio, 2-hydroxyethylthio, methyl, ethyl, acetamidoethyl, pyridylthio or ethylsulphinyl.

26. A composition according to claim 21 wherein the compound is in the form of a pharmaceutically acceptable in-vivo hydrolyzable ester wherein the ester moiety is of the formulae (a), (b) or (c):

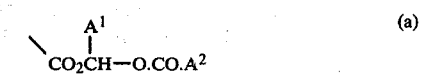

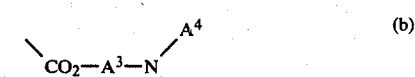

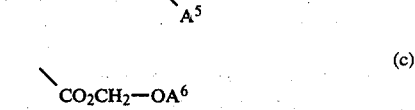

wherein $A^1$ is hydrogen, methyl or phenyl; $A^2$ is alkyl of 1-6 carbon atoms, alkoxy of 1-6 carbon atoms or phenyl; or $A^1$ and $A^2$ together form a 1,2-phenylene moiety unsubstituted or substituted by one or two methoxy groups; $A^3$ is alkyl of 1-6 carbon atoms unsubstituted or substituted by methyl or ethyl; $A^4$ and $A^5$ are alkyl of 1-6 carbon atoms; and $A^6$ is alkyl of 1-6 carbon atoms.

27. A composition according to claim 21 wherein the compound is in the form of a pharmaceutically in-vivo hydrolyzable ester wherein the ester is acetoxymethyl, pivaloyloxymethyl, α-acetoxyethyl, α-acetoxybenzyl, α-pivaloyloxyethyl, ethoxycarbonyloxymethyl, α-ethoxycarbonyloxyethyl, dimethylaminomethyl, diethylaminomethyl, diethylaminoethyl, phthalidyl or dimethoxyphthalidyl.

28. A composition according to claim 21 wherein the compound is in the form of a pharmaceutically acceptable salt wherein said salt is an alkali metal salt or an alkaline earth metal salt.

29. A composition according to claim 21 wherein the compound is in the form of a pharmaceutically acceptable salt wherein the salt is the sodium, potassium, calcium, magnesium, ammonium or a substituted ammonium salt, wherein the substituent is lower alkyl, hydroxy-lower alkyl or cycloalkyl, procaine, dibenzylamine, N,N-dibenzylethylenediamine, 1-ephenamine, N-ethylpiperidine, N-benzyl-β-phenethylamine, dehydroabetiylamine, N,N'-bisdehydroabietylethylenediamine, pyridine, collidine or quinoline.

30. A composition according to claim 21 wherein the compound is 6-(Z)-ethylidene-2-ethylthiopenem-3-carboxylic acid.

31. A composition according to claim 21 wherein the compound is 6-(E)-ethylidene-2-ethylthiopenem-3-carboxylic acid.

32. A composition according to claim 21 wherein the compound is 6-(Z)-ethylidenepenem-3-carboxylic acid.

33. A composition according to claim 21 wherein the compound is 6-(Z)-ethylidene-2-n-propylpenem-3-carboxylic acid.

34. A composition according to claim 21 wherein the compound is 2-(2-acetamidoethylthio)-6-ethylidenepenem-3-carboxylic acid.

35. A composition according to claim 21 wherein the compound is 6-(Z)-ethylidene-2-methylpenem-3-carboxylic acid.

36. A composition according to claim 21 wherein the compound is 6-ethylidene-2-(2-pyridylthio)penem-3-carboxylic acid.

37. A composition according to claim 21 wherein the compound is 2-(2-aminoethylthio)-6-ethylidenepenem-3-carboxylic acid.

38. A composition according to claim 21 wherein the compound is 6-ethylidene-2-ethylsulphinylpenem-3-carboxylic acid.

39. A composition according to claim 21 wherein the compound is 6-(Z)-benzylidene-2-ethylthiopenem-3-carboxylic acid.

40. A composition according to claim 21 wherein the compound is 2-ethylthio-6-isopropylidenepenem-3-carboxylic acid.

41. A composition according to claim 21 wherein the compound is in the form of a pharmaceutically acceptable alkali metal salt, a pharmaceutically acceptable alkaline earth metal salt or a salt with a pharmaceutically acceptable nitrogenous base.

42. A composition according to claim 21 in oral administration form.

43. A composition according to claim 21 in parenteral administration form.

44. A composition according to claim 21 in a form suitable for topical application.

45. A composition according to claim 21 for the treatment of infections of the respiratory tract, urinary tract or soft tissues in humans wherein the antibacterially effective amount is an amount sufficient to be effective against said infections.

46. A composition according to claim 21 for the treatment of mastitis in cattle wherein the antibacterially effective amount comprises an amount sufficient to be effective for the treatment of mastitis in cattle.

47. A method of treating bacterial infections in humans and animals which comprises administering to a human or animal in need thereof a therapeutically effective amount of a compound of the formula (II):

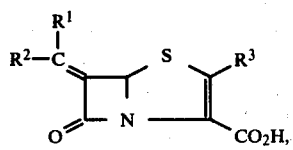

(II)

a pharmaceutically acceptable salt or pharmaceutically acceptable in-vivo hydrolysable ester thereof, wherein $R^1$ and $R^2$ are the same or different and each is hydrogen, alkyl of 1 to 6 carbon atoms, phenyl or a non-toxic heterocyclic group unsubstituted or substituted with a pharmaceutically acceptable functional group; and $R^3$ is hydrogen, $R^a$ or $-SR^a$ wherein $R^a$ is alkyl of 1 to 6 carbon atoms or phenyl unsubstituted or substituted by hydroxy, alkoxy of 1-6 carbon atoms, alkanoyloxy of 1-6 carbon atoms, halo, mercapto, alkylthio of 1-6 carbon atoms, amino, mono- or dialkylamino of 1-6 carbon atoms in the alkyl moiety, alkanoylamino of 1-6 carbon atoms, carboxy or alkoxycarbonyl of 1-6 carbon atoms; or $R^3$ is pyridylthio, in combination with a pharmaceutically acceptable carrier.

48. A method according to claim 47 wherein $R^1$ and $R^2$ are each hydrogen or a hydrocarbon of 1-10 carbon atoms.

49. A method according to claim 47 wherein $R^1$ and $R^2$ are each hydrogen or alkyl of 1-6 carbon atoms.

50. A method according to claim 47 wherein $R^1$ and $R^2$ are hydrogen, methyl, ethyl or phenyl.

51. A method according to claim 47 wherein $R^3$ is hydrogen, aminomethyl, aminoethyl, methylthio, ethylthio, 2-aminoethylthio, 2-hydroxyethylthio, methyl, ethyl, acetamidoethyl, pyridylthio or ethylsulphinyl.

52. A method according to claim 47 wherein the compound is in the form of a pharmaceutically acceptable in-vivo hydrolyzable ester wherein the ester moiety is of the formulae (a), (b) or (c):

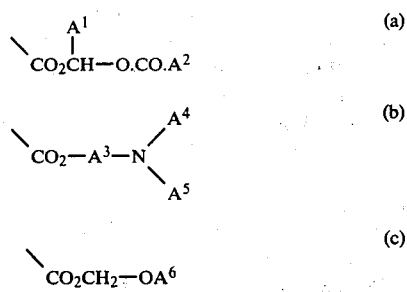

wherein $A^1$ is hydrogen, methyl or phenyl; $A^2$ is alkyl of 1-6 carbon atoms, alkoxy of 1-6 carbon atoms or phenyl; or $A^1$ and $A^2$ together form a 1,2-phenylene moiety unsubstituted or substituted by one or two methoxy groups; $A^3$ is alkyl of 1-6 carbon atoms unsubstituted or substituted by methyl or ethyl; $A^4$ and $A^5$ are alkyl of 1-6 carbon atoms; and $A^6$ is alkyl of 1-6 carbon atoms.

53. A method according to claim 47 wherein the compound is in the form of a pharmaceutically acceptable in-vivo hydrolyzable ester wherein the ester is acetoxymethyl, pivaloyloxymethyl, α-acetoxyethyl, α-acetoxybenzyl, α-pivaloyloxyethyl, ethoxycarbonyloxymethyl, α-ethoxycarbonyloxyethyl, dimethylaminomethyl, diethylaminomethyl, diethylaminoethyl, phthalidyl or dimethoxyphthalidyl.

54. A method according to claim 47 wherein the compound is in the form of a pharmaceutically acceptable salt wherein said salt is an alkali metal salt or an alkaline earth metal salt.

55. A method according to claim 47 wherein the compound is in the form of a pharmaceutically acceptable salt wherein the salt is the sodium, potassium, calcium, magnesium, ammonium or a substituted ammonium salt, wherein the substituent is lower alkyl, hydroxy-lower alkyl or cycloalkyl, procaine, dibenzylamine, N,N-dibenzylethylenediamine, 1-ephenamine, N-ethylpiperidine, N-benzyl-β-phenethylamine, dehydroabietylamine, N,N'-bisdehydroabietylethylenediamine, pyridine, collidine or quinoline.

56. A method according to claim 47 wherein the compound is 6-(Z)-ethylidene-2-ethylthiopenem-3-carboxylic acid.

57. A method according to claim 47 wherein the compound is 6-(E)-ethylidene-2-ethylthiopenem-3-carboxylic acid.

58. A method according to claim 47 wherein the compound is 6-(Z)-ethylidenepenem-3-carboxylic acid.

59. A method according to claim 47 wherein the compound is 6-(Z)-ethylidene-2-n-propylpenem-3-carboxylic acid.

60. A method according to claim 47 wherein the compound is 2-(2-acetamidoethylthio)-6-ethylidenepenem-3-carboxylic acid.

61. A method according to claim 47 wherein the compound is 6-(Z)-ethylidene-2-methylpenem-3-carboxylic acid.

62. A method according to claim 47 wherein the compound is 6-ethylidene-2-(2-pyridylthio)penem-3-carboxylic acid.

63. A method according to claim 47 wherein the compound is 2-(2-aminoethylthio)-6-ethylidenepenem-3-carboxylic acid.

64. A method according to claim 47 wherein the compound is 6-ethylidene-2-ethylsulphinylpenem-3-carboxylic acid.

65. A method according to claim 47 wherein the compound is 6-(Z)-benzylidene-2-ethylthiopenem-3-carboxylic acid.

66. A method according to claim 47 wherein the compound is 2-ethylthio-6-isopropylidenepenem-3-carboxylic acid.

67. A method according to claim 47 wherein the compound is in the form of a pharmaceutically acceptable alkali metal salt, a pharmaceutically acceptable lakaline earth metal salt or a salt with a pharmaceutically acceptable nitrogenous base.

68. A method according to claim 47 wherein the administration is oral.

69. A method according to claim 47 wherein the administration is parenteral.

70. A method according to claim 47 wherein the administration is by topical application.

71. A method according to claim 47 for the treatment of infections in the respiratory tract, urinary tract or soft tissues in humans.

72. A method according to claim 47 for the treatment of mastitis in cattle which comprises administering to cattle in need thereof an amount sufficient to be effective for the treatment of mastitis.

* * * * *